United States Patent [19]

Natarajan et al.

[11] Patent Number: 4,470,973
[45] Date of Patent: Sep. 11, 1984

[54] SUBSTITUTED PEPTIDE COMPOUNDS

[75] Inventors: Sesha I. Natarajan, Neshanic Station; Eric M. Gordon, Pennington, both of N.J.

[73] Assignee: E. R. Squibb & Sons, Inc., Princeton, N.J.

[21] Appl. No.: 500,581

[22] Filed: Jun. 2, 1983

Related U.S. Application Data

[63] Continuation-in-part of Ser. No. 399,650, Jul. 19, 1982, abandoned.

[51] Int. Cl.³ .............. A61K 37/00; A01N 43/50; A01N 43/36; C07D 231/00; C07D 211/60; C07D 217/00; C07D 103/52
[52] U.S. Cl. .............. 424/177; 424/273 R; 424/274; 546/245; 546/146; 548/180; 548/470; 548/356; 548/492; 260/112.5 R
[58] Field of Search .............. 260/112.5 R; 548/180, 548/470, 356, 492; 546/245, 146; 424/274, 273 R, 177

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,129,566 | 12/1978 | Ondetti et al. | 546/326 |
| 4,154,935 | 5/1979 | Ondetti et al. | 546/189 |
| 4,192,878 | 3/1980 | Ondetti | 424/270 |
| 4,199,512 | 4/1980 | Ondetti et al. | 260/326.12 R |
| 4,211,786 | 7/1980 | Rovnyak | 424/273 |
| 4,217,359 | 8/1980 | Krapcho | 424/274 |
| 4,234,489 | 11/1980 | Ondetti et al. | 260/326.42 |
| 4,254,267 | 3/1981 | Rovnyak | 548/379 |
| 4,256,751 | 3/1981 | Hayashi et al. | 424/258 |
| 4,256,761 | 3/1981 | Suh et al. | 424/282 |
| 4,266,065 | 5/1981 | Rovnyak | 548/379 |
| 4,296,033 | 10/1981 | Petrillo et al. | 260/326.2 |
| 4,296,113 | 10/1981 | Ondetti | 424/246 |
| 4,310,461 | 1/1982 | Krapcho | 260/326.2 |
| 4,311,687 | 1/1982 | Krapcho | 424/240 |
| 4,316,905 | 2/1982 | Krapcho | 424/274 |
| 4,316,906 | 2/1982 | Ondetti et al. | 424/274 |
| 4,329,473 | 5/1982 | Almquist et al. | 546/281 |
| 4,337,201 | 6/1982 | Petrillo | 548/413 |
| 4,374,829 | 2/1983 | Harris et al. | 424/177 |

FOREIGN PATENT DOCUMENTS

| | | | |
|---|---|---|---|
| 868532 | 7/1978 | Belgium . | |
| 12401 | 6/1980 | European Pat. Off. . | |
| 0038758 | 10/1981 | European Pat. Off. | 260/112.5 R |
| 45161 | 2/1982 | European Pat. Off. . | |
| 0050800 | 5/1982 | European Pat. Off. | 260/112.5 R |
| 0054862 | 6/1982 | European Pat. Off. | 260/112.5 R |
| 2027025 | 2/1980 | United Kingdom . | |
| 2048863 | 12/1980 | United Kingdom . | |

OTHER PUBLICATIONS

Almquist et al., "Synthesis and Biological Activity . . . Angiotensin converting Enzyme", J. med. Chem., 1980, 23, pp. 1392–1398.

Meyer et al., "Novel Synthesis of (S)-1-[5-(Benzoylamino)-1,4-dioxo-6-phenylhexyl]-L-proline", J., Med. Chem., 1981, 24, pp. 964–969.

Meyer et al., "Angiotensin converting Enzyme Inhibitors: Modifications of A tripeptide analogue, J. med. Chem., 1982, 25, pp. 996–999.

*Primary Examiner*—Delbert R. Phillips
*Attorney, Agent, or Firm*—Lawrence S. Levinson; Stephen B. Davis

[57] ABSTRACT

Substituted peptide compounds of the formula

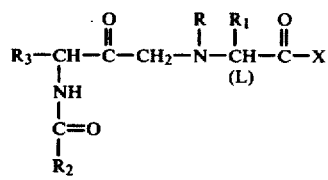

are disclosed. These compounds are useful as hypotensive agents due to their angiotensin converting enzyme inhibition activity and depending upon the definition of X may also be useful as analgesics due to their enkephalinase inhibition activity.

53 Claims, No Drawings

SUBSTITUTED PEPTIDE COMPOUNDS

RELATED APPLICATION

This application is a continuation-in-part of U.S. patent application Ser. No. 399,650, filed July 19, 1982, now abandoned.

BACKGROUND OF THE INVENTION

Almquist et al., "Synthesis and Biological Activity of a Ketomethylene Analogue of a Tripeptide Inhibitor of Angiotensin Converting Enzyme", J. Med. Chem., 1980, 23, 1392–1398, disclose the ketomethylene compound of the formula

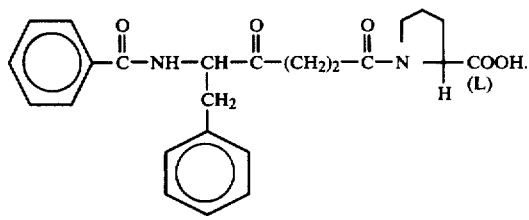

Meyer et al., "Novel Synthesis of (S)-1-[5-(Benzoylamino)-1,4-dioxo-6-phenylhexyl]-L-proline and Analogues:Potent Angiotensin Converting Enzyme Inhibitors", J. Med. Chem., 1981, 24, 964–969, disclose the synthesis and activity of compounds of the formula

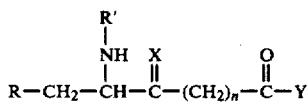

Meyer et al., "Angiotensin Converting Enzyme Inhibitors: Modifications Of A Tripeptide Analogue", J. Med. Chem., 1982, 25, 996–999, disclose the synthesis and activity of compounds of the formula

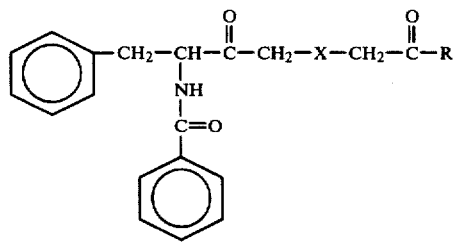

wherein X can be NH and R can be L-proline.

Almquist et al. in U.S. Pat. No. 4,329,473 disclose oxoalkanoic acid derivatives of L-proline as angiotensin converting enzyme inhibitors.

Gravestock et al. in European Patent Application No. 45161 disclose hypotensive compounds of the formula

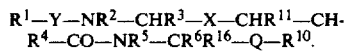

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.S. Pat. No. 4,311,697 discloses compounds wherein the proline ring has a diether, dithioether, ketal or thioketal substituent in the 4-position. Krapcho in U.S. Pat. No. 4,316,905 discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position. Krapcho, et al. in U.S. Pat. No. 4,310,461 disclose such compounds wherein the proline has an imido, amido, or amino substituent in the 4-position. Iwao, et al. in U.K. Patent Application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgium Pat. No. 868,532.

Mercaptoacyl derivatives of dihydroisoindole carboxylic acids and tetrahydroisoquinoline carboxylic acids are disclosed as being useful hypotensive agents by Ondetti et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

Various carboxyalkyl dipeptide angiotensin converting enzyme inhibitors are disclosed by Patchett et al. in European Patent Application No. 12,401 and by Harris et al. in U.S. Pat. No. 4,374,829.

SUMMARY OF THE INVENTION

This invention is directed to substituted peptide compounds of formula I and salts thereof

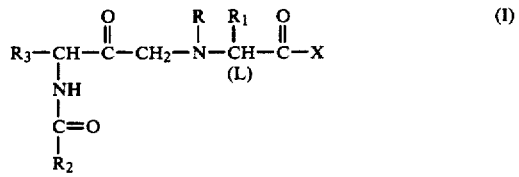

X is an amino or imino acid of the formula

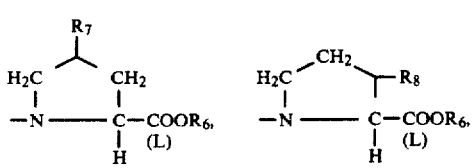

-continued
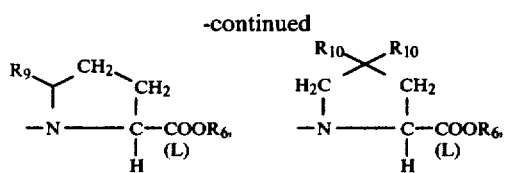
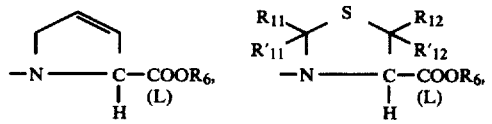
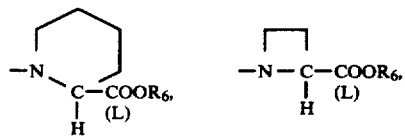
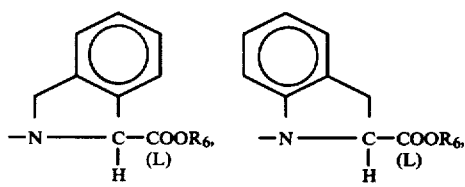
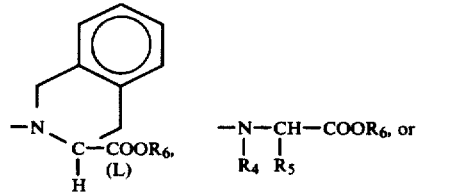
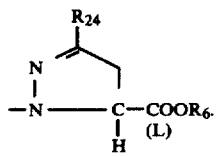
R<sub>7</sub> is hydrogen, lower alkyl, halogen, keto, hydroxy,
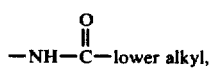
azido, amino,
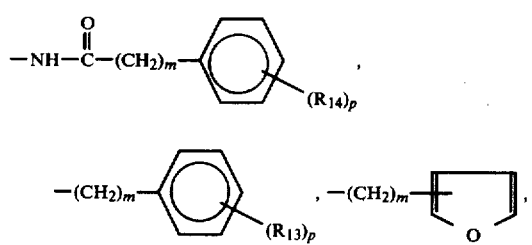
-continued
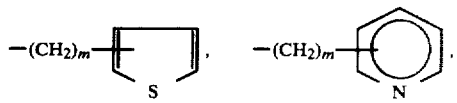
a 1- or 2-naphthyl of the formula
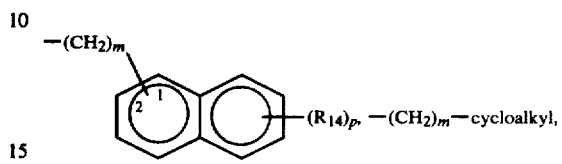
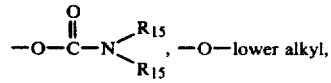
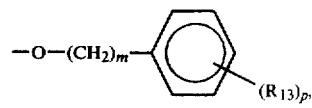
a 1- or 2-naphthyloxy of the formula
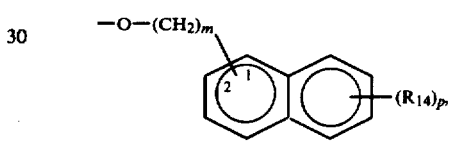
—S—lower alkyl,
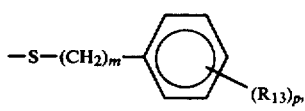
or a 1- or 2-naphthylthio of the formula
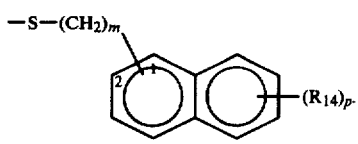
R<sub>8</sub> is keto, halogen,
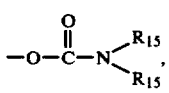
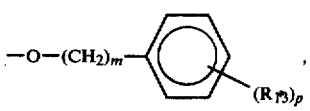
—O—lower alkyl, a 1- or 2-naphthyloxy of the formula

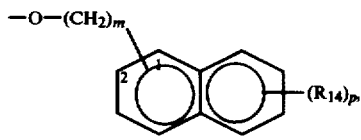

—S—lower alkyl,

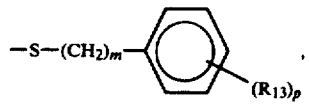

or a 1- or 2-naphthylthio of the formula

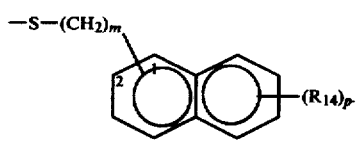

$R_9$ is keto or

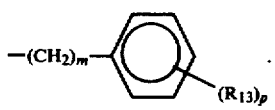

$R_{10}$ is halogen or —Y—$R_{16}$.
$R_{11}$, $R_{11}'$, $R_{12}$ and $R_{12}'$ are independently selected from hydrogen and lower alkyl or $R_{11}'$, $R_{12}$ and $R_{12}'$ are hydrogen and $R_{11}$ is

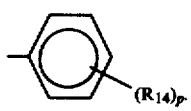

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.
m is zero, one, two, three, or four.
p is one, two or three provided that p is more than one only if $R_{13}$ or $R_{14}$ is hydrogen, methyl, methoxy, chloro, or fluoro.
$R_{15}$ is hydrogen or lower alkyl of 1 to 4 carbons.
Y is oxygen or sulfur.
$R_{16}$ is lower alkyl of 1 to 4 carbons,

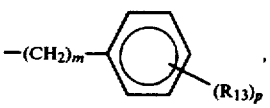

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.
$R_4$ is hydrogen, lower alkyl,

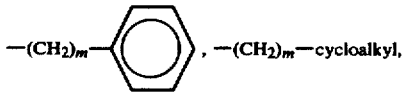

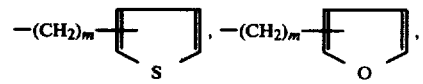

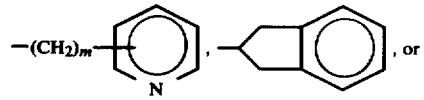

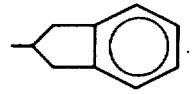

$R_5$ is hydrogen, lower alkyl,

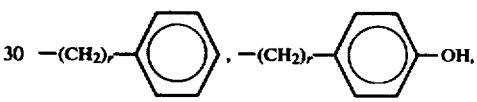

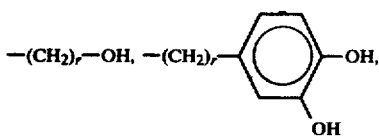

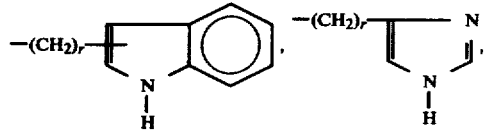

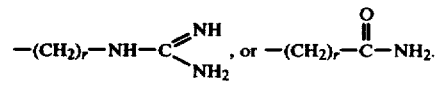

r is an integer from 1 to 4.
$R_{19}$ is lower alkyl, benzyl, or phenethyl.
$R_{20}$ is hydrogen, lower alkyl, benzyl or phenethyl.
R is hydrogen, lower alkyl, cycloalkyl,

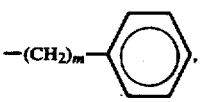

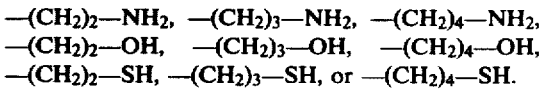

$R_1$ is hydrogen, lower alkyl, halo substituted lower alkyl,

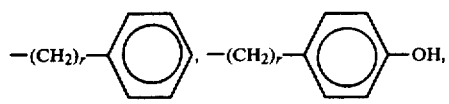, 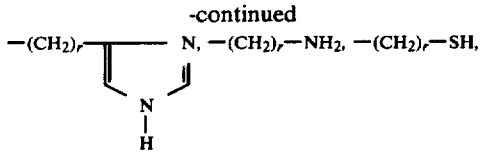

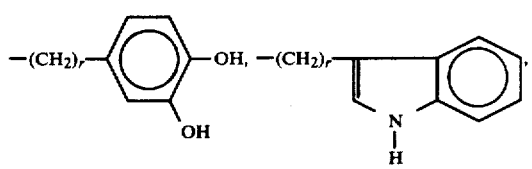

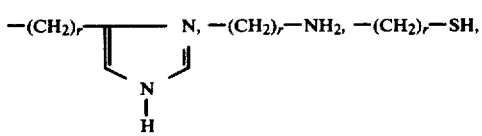

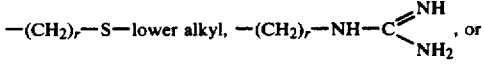

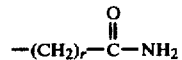

wherein m, $R_{14}$, p and r are as defined above.

$R_6$ is hydrogen, lower alkyl, benzyl, benzhydryl,

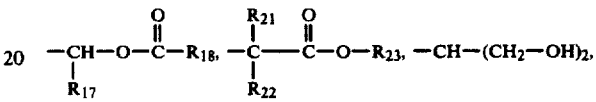

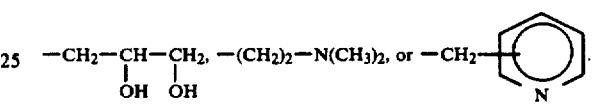

provided that $R_1$ is hydrogen only if R is other than hydrogen.

$R_2$ is

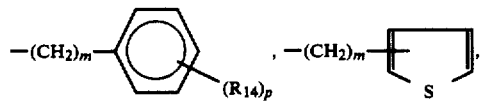

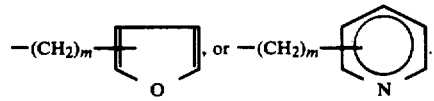

$R_3$ is hydrogen, lower alkyl,

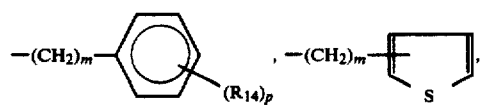

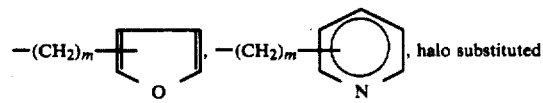 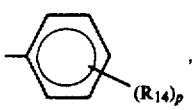

lower alkyl, $-(CH_2)_m-$cycloalkyl, 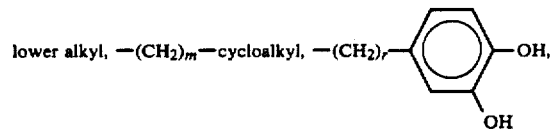

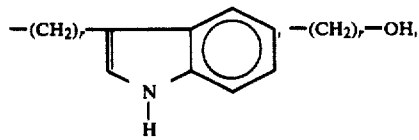

$R_{17}$ is hydrogen, lower alkyl, cycloalkyl, or phenyl.

$R_{18}$ is hydrogen, lower alkyl, lower alkoxy, or phenyl or $R_{17}$ and $R_{18}$ taken together are $-(CH_2)_2-$, $-(CH_2)_3-$, $-CH=CH-$, or

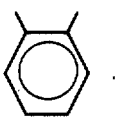

$R_{21}$ and $R_{22}$ are independently selected from hydrogen and lower alkyl.

$R_{23}$ is lower alkyl.

$R_{24}$ is hydrogen, lower alkyl,

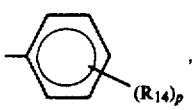

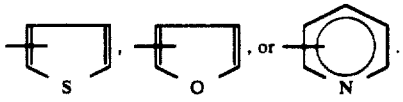

DETAILED DESCRIPTION OF THE INVENTION

This invention in its broadest aspects relates to the substituted peptide compounds of formula I above, to compositions and the method of using such compounds as pharmaceutical agents, and to intermediates useful in preparing these compounds.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

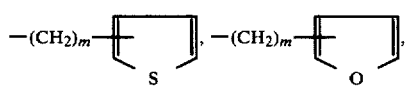

and

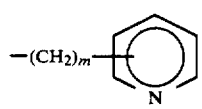

represent that the alkylene bridge is attached to an available carbon atom.

The compounds of formula I wherein R is hydrogen can be prepared by converting a carboxymethyl peptide ester of the formula

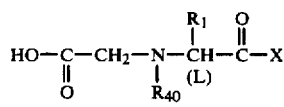
(II)

to its acid chloride and then reacting with an oxazolone of the formula

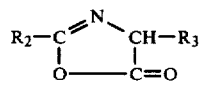
(III)

wherein $R_{40}$ and $R_6$ (in the definition of X) are protecting groups such as, for example, wherein $R_{40}$ is benzyloxycarbonyl and $R_6$ is benzyl. Removal of the $R_{40}$ and $R_6$ protecting group, for example, by hydrogenation yields the products of formula I wherein $R_6$ is hydrogen.

The carboxymethyl peptide ester of formula II is prepared by reacting the peptide ester of the formula

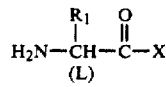
(IV)

with tert-butyl bromoacetate and then introducing the $R_{40}$ protecting group, for example, by treating with benzyl chloroformate.

The compounds of formula I can also be prepared by reacting a ketone of the formula

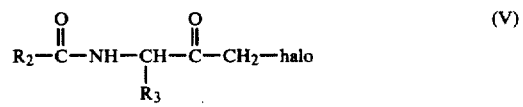
(V)

wherein halo is Cl or Br with the peptide ester of the formula

(VI)

in the presence of base such as sodium bicarbonate followed by removal of the $R_6$ ester group.

The ketone intermediate of formula V can be prepared by treating a ketone of the formula

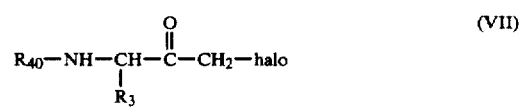
(VII)

wherein $R_{40}$ is a protecting group such as benzyloxycarbonyl with hydrogen bromide and acetic acid followed by reaction with the acid halide of the formula

(VIII)

in the presence of base such as sodium bicarbonate.

The compounds of formula I can also be prepared by reacting an aminoketone of the formula

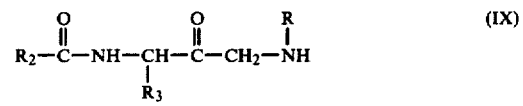
(IX)

particularly the hydrochloride salt thereof with the haloacetyl amino or imino acid ester of the formula

(X)

wherein $R_6$ in the definition of X is an easily removable ester protecting group and halo is Cl or Br.

The compounds of formula I can also be prepared by coupling an aminoketone carboxylic acid or its chemical equivalent of the formula

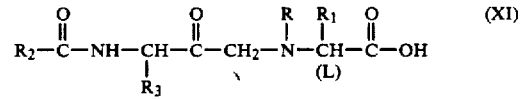
(XI)

with the amino or imino acid or ester of the formula

HX.  (XII)

This reaction can be performed in the presence of a coupling agent such as dicyclohexylcarbodiimide or the like, or by conversion of the acid of formula XI to its mixed anhydride, symmetrical anhydride, acid halide, active ester or by use of Woodward reagent K, N-ethoxycarbonyl-2-ethoxy-1,2-dihydroquinoline or the like. For a review of the methods of acylation see Methoden der Organischen Chemie (Houben-Weyl), Vol. XV, part II, page 1 et seq. (1974). Preferably, the N-succinimide active ester form of the compound of formula XI is reacted with the acid of formula XII.

In these reactions, if R is hydrogen then that N-atom is protected by an easily removable protecting group such as benzyloxycarbonyl.

The aminoketone of formula IX can be prepared by converting the carboxyalkylamine of the formula $$HO-\underset{\underset{O}{\|}}{C}-CH_2-\underset{\underset{}{|}}{N}-R_{40} \qquad (XIII)$$
$$\phantom{HO-\,}\overset{R}{|}$$

wherein $R_{40}$ is a protecting group such as benzyloxycarbonyl, to its acid chloride and then reacting with an oxazolone of formula III to yield $$R_2-\underset{\underset{}{\|}}{C}-NH-CH-\underset{\underset{}{\|}}{C}-CH_2-\underset{\underset{}{|}}{N}-R_{40}. \qquad (XIV)$$

Removal of the $R_{40}$ protecting group such as by hydrogenation yields the reactant of formula IX.

The aminoketone of formula IX wherein R is other than hydrogen can also be prepared by reacting the ketone of formula V with a substituted amine of the formula $$R-NH_2. \qquad (XV)$$

The aminoketone carboxylic acid of formula XI can be prepared by reacting the aminoketone of formula IX with a haloacetic acid ester of the formula $$halo-\underset{\underset{}{|}}{CH}-\underset{\underset{}{\|}}{C}-O-Prot \qquad (XVI)$$
$$\phantom{halo-}\overset{R_1}{|}\ \overset{O}{\|}$$
(L)

wherein Prot is an easily removable ester protecting group such as t-butyl to yield the ester $$R_2-\underset{}{C}-NH-CH-\underset{}{C}-CH_2-NH-CH-\underset{}{C}-O-Prot. \qquad (XVII)$$
(L)

Removal of the ester protecting group gives the reactant of formula XI.

In the above reactions if any or all of R, $R_1$, $R_3$ and $R_5$ are $-(CH_2)_r-\text{C}_6\text{H}_4-OH$, $-(CH_2)_r-\text{C}_6\text{H}_3(OH)-OH$, -continued $-(CH_2)_r-NH_2$, $-(CH_2)_r-\text{(imidazolyl)}$, $-(CH_2)_r-SH$, $-(CH_2)_r-OH$, or $-(CH_2)_r-NH-C(=NH)NH_2$ then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is lower alkyl, benzyl or benzhydryl can be chemically treated such as with sodium hydroxide in aqueous dioxane or with trimethylsilylbromide to yield the products of formula I wherein $R_6$ is hydrogen. The benzyl and benzhydryl esters can also be hydrogenated, for example, by treating with hydrogen in the presence of a palladium on carbon catalyst.

The ester products of formula I wherein $R_6$ is $$-CH-O-\underset{\underset{}{\|}}{C}-R_{18}$$
$$\overset{}{|}$$
$$R_{17}$$

may be obtained by employing the peptide of formula IV or VI or the haloacetyl amino or imino acid ester of formula X in the above reactions with such ester group already in place. Such ester reactants can be prepared by treating the peptide of formula IV or VI or the haloacetyl amino or imino acid ester of formula X wherein $R_6$ is hydrogen with an acid chloride such as $\text{C}_6\text{H}_5-CH_2-O-\overset{O}{\underset{\|}{C}}-Cl$ or $(H_3C)_3-C-O-\overset{O}{\underset{\|}{C}}-Cl$ so as to protect the N-atom. The protected compound is then reacted in the presence of a base with a compound of the formula $$L-CH-O-\underset{\underset{}{\|}}{C}-R_{18} \qquad (XVIII)$$
$$\overset{}{|}$$
$$R_{17}$$

wherein L is a leaving group such as chlorine, bromine, tolylsulfonyl, etc., followed by removal of the N-protecting group such as by treatment with acid or hydrogenation.

The ester products of formula I wherein $R_6$ is

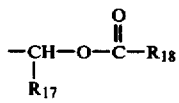

can also be obtained by treating the product of formula I wherein $R_6$ is hydrogen with a molar excess of the compound of formula XVIII.

The ester products of formula I wherein $R_6$ is

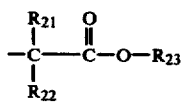

can be prepared by treating the product of formula I wherein $R_6$ is hydrogen with a molar excess of the compound of the formula

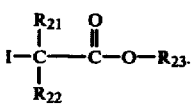

(XIX)

The ester products of formula I wherein $R_6$ is —CH—(CH$_2$—OH)$_2$ or

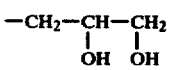

can be prepared by coupling the product of formula I wherein $R_6$ is hydrogen with a molar excess of the compound of the formula

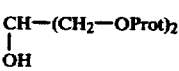

(XX)

or the formula

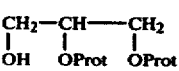

(XXI)

in the presence of a coupling agent such dicyclohexylcarbodiimide followed by removal of the hydroxyl protecting groups.

Similarly, the ester products of formula I wherein $R_6$ is —(CH$_2$)$_2$—N(CH$_3$)$_2$ or

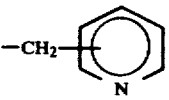

can can be prepared by coupling the product of formula I wherein $R_6$ is hydrogen with a molar excess of the compound of the formula

HO—CH$_2$—CH$_2$—N—(CH$_3$)$_2$  (XXII)

or the formula

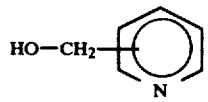

(XXIII)

in the presence of a coupling agent such as dicyclohexylcarbodiimide.

The esters of formula I wherein $R_6$ is lower alkyl can be obtained from the carboxylic acid compounds, i.e., wherein $R_6$ is hydrogen, by conventional esterification procedures, e.g., treatment with an alkyl halide of the formula $R_6$-halo or an alcohol of the formula $R_6$—OH.

The peptide esters of formulas IV and VI may be obtained by coupling the hydrochloride salt of the amino or imino acid ester of formula XII wherein $R_6$ is, for example, benzyl with the N-protected amino acid of the formula

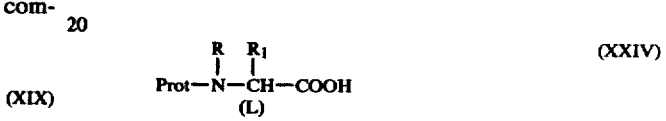

wherein Prot is a protecting group such as

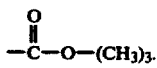

Preferably, this reaction is performed in the presence of a coupling agent such as dicyclohexylcarbodiimide. Removal of the N-protecting group, for example, by treatment with trifluoroacetic acid yields the peptide esters of formulas IV and VI.

The haloacetyl amino or imino acid ester of formula X can be prepared by reacting the amino or imino acid ester of formula XII with a haloacetylhalide of the formula

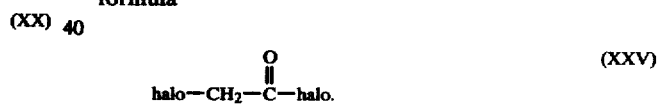

The products of formula I wherein $R_7$ is amino may be obtained by reducing the corresponding products of formula I wherein $R_7$ is azido.

Preferred compounds of this invention with respect to the peptide part of the structure of formula I are those wherein:

R is hydrogen, straight or branched chain lower alkyl of 1 to 4 carbons, or phenyl.

$R_1$ is hydrogen, straight or branched chain lower alkyl of 1 to 4 carbons, —CF$_3$, —(CH$_2$)$_r$—NH$_2$ wherein r is an integer from 1 to 4,

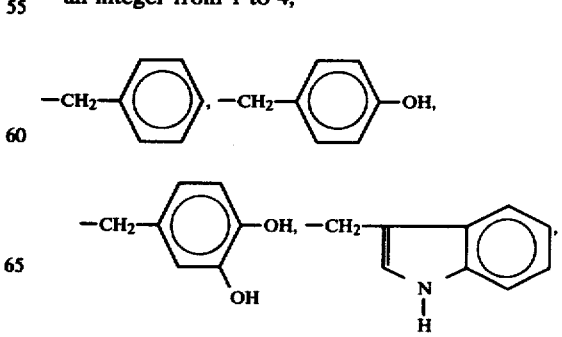

-continued $-CH_2-\underset{\underset{H}{|}}{\underset{N}{\diagdown}}\overset{N}{\diagup}$, $-CH_2-SH$, $-(CH_2)_2-S-CH_3$, $-(CH_2)_3NHC\underset{NH_2}{\overset{NH}{\diagdown}}$, $-CH_2-OH$, $-CH_2-\overset{O}{\overset{\|}{C}}-NH_2$, or $-(CH_2)_2-\overset{O}{\overset{\|}{C}}-NH_2$ provided that $R_1$ is hydrogen only if R is other than hydrogen.

$R_4$ is hydrogen, cyclohexyl or phenyl.

$R_5$ is hydrogen, straight or branched chain lower alkyl of 1 to 4 carbons, $-CH_2OH$, $-CH_2-\bigcirc$, $-CH_2-\bigcirc-OH$, $-CH_2-\bigcirc\underset{OH}{\overset{OH}{\phantom{.}}}$, $-CH_2-\underset{\underset{H}{|}}{\bigcirc\!\!\!\diagdown\!\!\!\!N}$, $-CH_2-\underset{\underset{H}{|}}{\underset{N}{\diagdown}}\overset{N}{\diagup}$, $-(CH_2)_4-NH_2$, $-CH_2-SH$, $-(CH_2)_2-S-CH_3$, $-(CH_2)_3NHC\underset{NH_2}{\overset{NH}{\diagdown}}$, $-CH_2-\overset{O}{\overset{\|}{C}}-NH_2$ or $-(CH_2)_2-\overset{O}{\overset{\|}{C}}-NH_2$.

$R_6$ is hydrogen, straight or branched chain lower alkyl of 1 to 4 carbons, alkali metal salt, $-\underset{R_{17}}{\overset{|}{C}H}-O-\overset{O}{\overset{\|}{C}}-R_{18}$, $-CH_2-\overset{O}{\overset{\|}{C}}-OR_{23}$, $-CH-(CH_2-OH)_2$, $-CH_2-\underset{OH}{\overset{|}{C}H}-\underset{OH}{\overset{|}{C}H_2}$, $-(CH_2)_2-N(CH_3)_2$, or $-CH_2-\bigcirc\!\!\!\diagdown\!\!\!N$.

$R_{23}$ is straight or branched chain lower alkyl of 1 to 4 carbons, especially $-C(CH_3)_3$.

$R_{17}$ is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is $-O-$lower alkyl wherein lower alkyl is straight or branched chain of 1 to 4 carbons.

$R_7$ is $-(CH_2)_m-\bigcirc-R_{13}$ wherein m is zero, one or two and $R_{13}$ is hydrogen, methyl, methoxy, methylthio, chloro, bromo, fluoro, or hydroxy.

$R_7$ is $-O-(CH_2)_m-\bigcirc-R_{13}$, 1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is $-S-$lower alkyl wherein lower alkyl is straight or branched chain of 1 to 4 carbons.

$R_7$ is $-S-(CH_2)_m-\bigcirc-R_{13}$, 1-naphthylthio, or 2-naphthylthio wherein m is zero, one, or two and $R_{13}$ is hydrogen, methyl, methoxy, methylthio, chloro, bromo, fluoro, or hydroxy.

$R_8$ is $-O-$lower alkyl wherein lower alkyl is straight or branched chain of 1 to 4 carbons.

$R_8$ is $-O-(CH_2)_m-\bigcirc-R_{13}$ wherein m is zero, one, or two and $R_{13}$ is hydrogen, methyl, methoxy, methylthio, chloro, bromo, fluoro, or hydroxy.

$R_8$ is $-S-$lower alkyl wherein lower alkyl is straight or branched chain of 1 to 4 carbons.

$R_8$ is $-S-(CH_2)_m-\bigcirc-R_{13}$ wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R_{11}'$, $R_{12}$ and $R_{12}'$ are all hydrogen, or $R_{11}$ is phenyl, 2-hydroxyphenyl, or 4-hydroxyphenyl and $R_{11}'$, $R_{12}$ and $R_{12}'$ are hydrogen.

$R_{24}$ is phenyl.

Most preferred compounds of this invention with respect to the peptide part of the structure of formula I are those wherein:

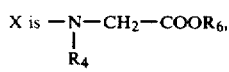

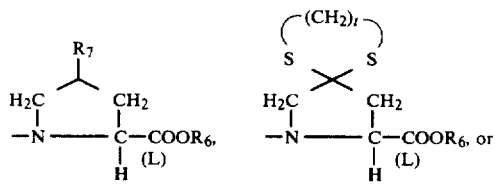

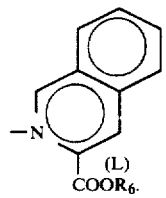

R is hydrogen or methyl.

$R_1$ is hydrogen, methyl, or —(CH$_2$)$_4$NH$_2$, especially methyl, provided that $R_1$ is hydrogen only if R is other than hydrogen.

$R_6$ is hydrogen, straight or branched chain lower alkyl of 1 to 4 carbons, or an alkali metal salt.

$R_4$ is cyclohexyl or phenyl.

$R_7$ is hydrogen, cyclohexyl, lower alkoxy of 1 to 4 carbons,

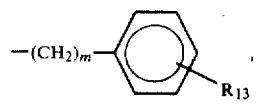

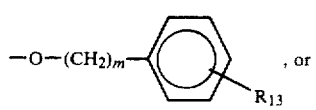

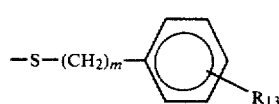

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to the keto portion of the structure of formula I are those wherein:

$R_2$ is

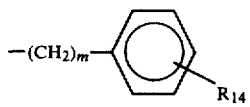

wherein m is zero, one, or two and $R_{14}$ is hydrogen, methyl, methoxy, methylthio, Cl, Br, F, or hydroxy, especially phenyl.

$R_3$ is straight or branched chain lower alkyl of 1 to 4 carbons, —(CH$_2$)$_r$—NH$_2$,

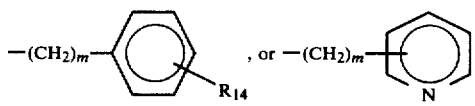

wherein m is zero, one, or two, $R_{14}$ is hydrogen, methyl, methoxy, methylthio, Cl, Br, F, or hydroxy, and r is an integer from 1 to 4, especially benzyl.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Similarly, the compounds of formula I, especially wherein $R_6$ is an ester group, form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

As shown above, the peptide portion of the molecule of the products of formula I represented by

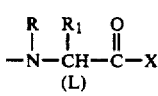

is in the L-configuration. An asymmetric center is also present in the keto portion of the molecule when $R_3$ is other than hydrogen. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula XII.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglubulin in blood, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

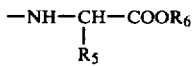

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade. LH-20 refers to a Sephadex chromatography gel commercially available from Pharmacia Fine Chemicals.

EXAMPLE 1

1-[N-[3-(Benzoylamino)-2-oxo-4-phenylbutyl]-L-alanyl]-L-proline, monohydrochloride (a) L-Alanyl-L-proline, phenylmethyl ester, p-toluenesulfonic acid salt N-[(1,1-Dimethylethoxy)carbonyl]-L-alanine (310.7 g.), L-proline, phenylmethyl ester, hydrochloride (396.2 g.), dicyclohexylcarbodiimide (338.6 g.), hydroxybenzotriazole hydrate (251.5 g.), diisopropylethylamine (285.7 ml.), and tetrahydrofuran (5 liters) are combined at 0° (dicyclohexylcarbodiimide is added last) and stirred at room temperature overnight. The reaction mixture is filtered and concentrated. The residue is dissolved in 4 l. of ethyl acetate and washed with 5% sodium bicarbonate (2×2 l.), 5% potassium bisulfate (2×2 l.) and water. The ethyl acetate layer is dried (MgSO$_4$) and concentrated. The residue is dissolved in 3 l. of diethyl ether and left at 0° overnight. The mixture is filtered and the filtrate concentrated to yield 620 g. of crude N-[(1,1-dimethylethoxy)carbonyl]-L-alanyl-L-proline, phenylmethyl ester.

N-[(1,1-Dimethylethoxy)carbonyl]-L-alanyl-L-proline, phenylmethyl ester (275 g.) is chilled in an ice bath and treated with 500 ml. of cold trifluoroacetic acid (freshly distilled) under argon and stirred at room temperature for one hour. The mixture is concentrated in vacuo and azeotroped twice with toluene. The crude trifluoroacetic acid salt, an oil, is dissolved in 500 ml. of ether and treated slowly with stirring with a solution of p-toluenesulfonic acid hydrate (1 equivalent) dissolved in 6 l. of ether. The resultant precipitate is collected by filtration. The solid is dissolved in 1 l. of methanol and treated with 4 l. of ether and chilled. The resultant precipitate is collected and dried to give 300 g. of L-alanyl-L-proline, phenylmethyl ester, p-toluenesulfonic acid salt; m.p. 156°–158°.

(b) 1-[N-[2-(1,1-Dimethylethoxy)-2-oxoethyl]-N-[(phenylmethoxy)carbonyl]-L-alanyl]-L-proline, phenylmethyl ester A mixture of L-alanyl-L-proline, phenylmethyl ester, p-toluenesulfonic acid salt (32.16 g., 72 mmole), tert-butyl bromoacetate (14.2 g., 72 mmole), triethylamine (20.1 ml., 144 mmole), and tetrahydrofuran (290 ml.) are stirred at room temperature for 72 hours. Benzyl chloroformate (12.4 ml., 87.8 mmole) and triethylamine (12.5 ml., 87.8 mmole) are added and the mixture stirred overnight. The reaction product is evaporated, and partitioned between water and ethyl acetate. The ethyl acetate solubles are washed with dilute hydrochloric acid and then water. The ethyl acetate solution is then evaporated and chromatographed over silica gel (mesh 230–400) using the solvent system ethyl acetate/hexane (1:1) (10 psi pressure) to give 19.5 g. of 1-[N-[2-(1,1- dimethylethylethoxy)-2-oxoethyl]-N-[(phenylmethoxy)carbonyl]-L-alanyl]-L-proline, phenylmethyl ester.

(c) 1-[N-(Carboxymethyl)-N-[(phenylmethoxy)carbonyl]-L-alanyl]-L-proline, phenylmethyl ester 1-[N-[2-(1,1-Dimethylethoxy)-2-oxoethyl]-N-[(phenylmethoxy)carbonyl]-L-alanyl]-L-proline, phenylmethyl ester (18 g., 34.3 mmole) is dissolved in trifluoroacetic acid (50 ml.) and let stand at room temperature for 1.5 hours. The mixture is evaporated and filtered through a small column of silica gel (200 g.) using the solvent mixture chloroform/methanol/acetic acid (9.6:0.2:0.2) to give 11.4 g. of 1-[N-(carboxymethyl)-N-[(phenylmethoxy)carbonyl]-L-alanyl]-L-proline, phenylmethyl ester.

(d) 1-[N-[3-(Benzoylamino)-2-oxo-4-phenylbutyl]-N-[(phenylmethoxy)carbonyl]-L-alanyl]-L-proline, phenylmethyl ester 1-[N-(carboxymethyl)-N-[(phenylmethoxy)carbonyl]-L-alanyl]-L-proline, phenylmethyl ester (7.0 g., 15.0 mmole) is dissolved in dry tetrahydrofuran (50 ml.) and cooled in an ice bath, oxalyl chloride (1.57 ml., 18 mmole) is added followed by 4 drops of dimethylformamide. After 15 minutes, the reaction mixture is stirred at room temperature for an additional period of one hour. The mixture is evaporated, redissolved in tetrahydrofuran (30 ml.) and the solution is cooled in an ice bath. The solution is added dropwise over a period of 5 minutes to an ice-cold solution of 2-phenyl-4-(phenylmethyl)-5(4H)-oxazolone (3.96 g., 15.75 mmole) in tetrahydrofuran (24 ml.). Triethylamine (2.5 ml., 17.1 mmole) is added and the reaction mixture is stirred at room temperature overnight. The mixture is filtered to remove triethylamine hydrochloride salt and the filtered tetrahydrofuran solution is evaporated and redissolved in pyridine (16 ml.). 4-Dimethylamino pyridine (50 mg.) is added and the solution is stirred at room temperature for 3 hours. Glacial acetic acid (16 ml.) is added and the reaction mixture is heated at 100° for 45 minutes. The reaction mixture is then cooled, evaporated under vacuum, dissolved in ethyl acetate and extracted with aqueous medium bicarbonate and dilute hydrochloric acid. The ethyl acetate extract after evaporation is chromatographed over silica gel (230–400 mesh) using the solvent system ethyl acetate/benzene (4:6) to obtain 4.9 g. of 1-[N-[3-(benzoylamino)-2-oxo-4-phenylbutyl]-N-[(phenylmethoxy)carbonyl]-L-alanyl]-L-proline, phenylmethyl ester.

Anal. calc'd. for $C_{40}H_{41}N_3O_7.0.42H_2O$: C, 70.31; N, 6.15; H, 6.17. Found: C, 70.31; N, 6.13; H, 6.08.

(e) 1-[N-[3-(Benzoylamino)-2-oxo-4-phenylbutyl]-L-alanyl]-L-proline, monohydrochloride 1-[N-[3-(Benzoylamino)-2-oxo-4-phenylbutyl]-N-[(phenylmethoxy)carbonyl]-L-alanyl]-L-proline, phneylmethyl ester (1.0 g.) is dissolved in absolute ethanol (30 ml.) and 1N hydrochloric acid (2.25 ml.). Palladium-carbon catalyst (10%, 200 mg.) is added and the solution is stirred under an atmosphere of hydrogen overnight. The catalyst is filtered off and the solution is evaporated. The crude product (700 mg.) is combined with 300 mg. of crude product from a previous small scale reaction and passed through a column of LH-20 (1 inch×15 inch) in methanol. The fractions containing the desired product are pooled, evaporated, dissolved in water and filtered. The clear aqueous solution is lyophilized to give 800 mg. of 1-[N-[3-(benzoylamino)-2-oxo-4-phenylbutyl]-L-alanyl]-L-proline, monohydrochloride; $[\alpha]_D^{25} = -59.6$ (c=1.4, methanol); m.p. 98°–130° (dec.). Tlc (silica gel, n-butanol/acetic acid/water, 4:1:1) $R_f = 0.44$.

Anal. calc'd. for $C_{25}H_{30}N_3O_5Cl.0.75H_2O$: C, 59.88; H, 6.33; N, 8.38; Cl, 7.07. Found: C, 59.82; H, 6.30; N, 8.42; Cl, 6.85.

EXAMPLE 2

1-[N-[7-Amino-3-(benzoylamino)-2-oxoheptyl]-L-alanyl]-L-proline, dihydrochloride (a) $N^2$-Benzoyl-$N^6$-[(phenylmethoxy)carbonyl]-L-lysine To an ice-cold solution of $N^6$-[(phenylmethoxy)carbonyl]-L-lysine (10.09 g., 36 mmole) in aqueous sodium hydroxide (1N, 26 ml.) is added benzoyl chloride (5 ml., 43.2 mmole) and aqueous sodium hydroxide (4N, 10.8 ml.) simultaneously in 5 portions over a period of 30 minutes. The ice bath is removed and stirring is continued for an additional 1.5 hours at room temperature. The reaction mixture is then extracted with ethyl acetate (discarded), the aqueous mother liquor is acidified with dilute hydrochloric acid and extracted with ethyl acetate. The ethyl acetate extract is concentrated and the residue crystallized from ethyl acetate-hexane to give 12.9 g. of $N^2$-benzoyl-$N^6$-[(phenylmethoxy)carbonyl]-L-lysine; m.p. 110°–112° (109°).

(b) 2-Phenyl-4-[4-[[(phenylmethoxy)carbonyl]amino]butyl]-5(4H)-oxazolone $N^2$-Benzoyl-$N^6$-[(phenylmethoxy)carbonyl]-L-lysine (11.53 g., 30 mmole) is dissolved in tetrahyrofuran (55 ml.) and stirred in an ice-bath. To this reaction mixture a solution of dicyclohexylcarbodiimide (6.8 g., 33 mole) in tetrahydrofuran is added dropwise over a period of 15 minutes. The ice-bath is removed after an hour and stirring is continued at room temperature for an additional 18 hours. Dicyclohexylurea is filtered off and the tetrahydrofuran is concentrated in vacuo. The residue is crystallized from ethyl acetate-hexane to give 9.4 g. of 2-phenyl-4-[4-[[(phenylmethoxy)carbonyl]amino]butyl]-5(4H)-oxazolone; m.p. 72°–73° (68°).

(c) 1-[N-[3-(Benzoylamino)-7-[[(phenylmethoxy)carbonyl]amino]-2-oxoheptyl]-N-[(phenylmethoxy)carbonyl]-L-alanyl]-L-proline, phenylmethyl ester 1-[N-(Carboxymethyl)-N-[(phenylmethoxy)carbonyl]-L-alanyl]-L-proline, phenylmethyl ester (2.82 g., 6 mmole), from Example 1(c), is dissolved in tetrahydrofuran (20 ml.) and the solution is stirred in an ice-bath. Oxalyl chloride (0.63 ml., 7.2 mmole) is added followed by four drops of dimethylformamide. After stirring this reaction mixture in an ice-bath for 20 minutes, it is then stirred at ambient temperature for an additional hour. The solvents are removed in vacuo and the residue is redissolved in tetrahydrofuran (10 ml.) and cooled in an ice-bath. To this cold stirring solution is added a cold solution 2-phenyl-4-[4-[[(phenylmethoxy)carbonyl]amino]butyl]-5(4H)-oxazolone (2.2 g., 6 mmole) in tetrahydrofuran (14 ml.), followed by triethylamine (0.85 ml., 6 mmole). The ice-bath is removed and the reaction mixture is stirred at ambient temperature overnight. The precipitated triethylamine-hydrochloride is removed by filtration and the mother liquor is concentrated in vacuo. It is then redissolved in pyridine (6 ml.), 4-dimethylamino pyridine (30 mg.) is added, and the solution is stirred at room temperature for 3 hours. Acetic acid (6 ml.) is added and the reaction mixture is heated at 105° for 45 minutes. It is then evaporated, taken up into ethyl acetate, and washed with water, dilute hydrochloric acid, and aqueous sodium bicarbonate. After evaporation of the solvent, the crude product (3.8 g.) is chromatographed (silica gel, 230 g.) using ethyl acetate-hexane (4:3) followed by ethyl acetate-hexane (2:1) for elution to give 1.8 g. of 1-[N-[3-(benzoylamino)-7-[[(phenylmethoxy)carbonyl]amino]-2-oxoheptyl]-N-[(phenylmethoxy)carbonyl]-L-alanyl]-L-proline, phenylmethyl ester.

(d) 1-[N-[7-Amino-3-(benzoylamino)-2-oxoheptyl]-L-alanyl]-L-proline, dihydrochloride 1-[N-[3-(Benzoylamino)-7-[[(phenylmethoxy)carbonyl]amino]-2-oxoheptyl]-N-[(phenylmethoxy)carbonyl]-L-alanyl]-L-proline, phenylmethyl ester (1.3 g., 1.6 mmole) is dissolved in ethanol (75 ml.) and aqueous hydrochloric acid (1N, 5 ml.). Palladium on carbon catalyst (10%, 450 mg.) is added and the mixture is hydrogenated at atmospheric pressure overnight. The catalyst is filtered off and the solution is evaporated in vacuo. The residue is dissolved in water and lyophilized. The lyophilate is triturated with ether to give 0.6 g. of 1-[N-[7-amino-3-(benzoylamino)-2-oxoheptyl]-L-alanyl]-L-proline, hydrochloride; m.p. 80°-155°; $[\alpha]_D^{22} = -50°$ (c=1.1, methanol). R$_f$ 0.09 (silica gel, n-butanol/acetic acid/water, 4:1:1).

Anal. calc'd. for $C_{22}H_{32}N_4O_5.2HCl.1.5H_2O$: C, 49.63; H, 7.00; N, 10.52; Cl, 13.55. Found: C, 49.63; H, 6.82; N, 10.48; Cl, 13.36.

EXAMPLE 3

1-[N-[3-(Benzoylamino)-2-oxoheptyl]-L-alanyl]-L-proline, monohydrochloride (a) N-Benzoyl-D,L-norleucine D,L-Norleucine (39.3 g., 300 mmole) is taken up into sodium hydroxide (2N, 150 ml.) and while stirring in an ice-bath sodium hydroxide (2N, 150 ml.) and benzoyl chloride (330 mmole, 38.3 ml.) are added over a 30 minute period. The bath is removed and after 1.5 hours the reaction mixture is extracted with ether. The aqueous portion is acidified with 2N hydrochloric acid and the crystals filtered to give 68.9 g. of N-benzoyl-D,L-norleucine; m.p. 131°-133° (125°).

(b) 4-Butyl-2-phenyl-5(4H)-oxazolone

N-Benzoyl-D,L-norleucine (40 g., 170 mmole) is taken up into tetrahydrofuran (300 ml.) with stirring in an ice-bath. To this reaction mixture a solution of dicyclohexylcarbodiimide (38.52 g., 187 mmole) in tetrahydrofuran (195 ml.) is added dropwise over a period of 15 minutes. The ice-bath is removed and stirring is continued at room temperature for an additional 18 hours. Dicyclohexylurea is filtered off and the tetrahydrofuran is concentrated in vacuo. The residue (31.7 g.) is purified on silica in hexane:ether (2:1) to yield 32.1 g. of 4-butyl-2-phenyl-5(4H)-oxazolone.

(c) 1-[N-[3-(Benzoylamino)-2-oxoheptyl]-N-[(phenylmethoxy)carbonyl]-L-alanyl]-L-proline, phenylmethyl ester A solution of 1-[N-(carboxymethyl)-N-[-(phenylmethoxy)carbonyl]-L-alanyl]-L-proline, phenylmethyl ester (1.41 g., 3 mmole), from Example 1(c), in tetrahydrofuran (10 ml.) is cooled in an ice-bath. While stirring, oxalyl chloride (0.32 ml., 3.7 mmole) is added followed by 4 drops of dimethylformamide. The reaction mixture is stirred in the ice-bath for 20 minutes and then at room temperature for one hour. It is evaporated in vacuo, redissolved in tetrahydrofuran (5 ml.) and cooled in an ice-bath. A cold solution of 4-butyl-2-phenyl-5(4H)-oxazolone (0.65 g., 3 mmole) in tetrahydrofuran (5 ml.) is added dropwise followed by triethylamine (0.43 ml., 3.1 mmole). The reaction mixture is stirred at ambient temperature overnight. After filtering off triethylamine hydrochloride, the tetrahydrofuran solution is concentrated in vacuo. The residue is redissolved in pyridine (3 ml.), 4-dimethylamino pyridine (15 mg.) is added, and the reaction mixture is stirred at room temperature for 3 hours. Acetic acid (3 ml.) is added and the reaction mixture is heated at 100° for 40 minutes. It is then evaporated, redissolved in ethyl acetate and washed with water, saturated sodium bicarbonate, dilute hydrochloric acid, and water. After evaporation, the residue is chromatographed over silica gel using the solvent system ethyl acetate:benzene (4:6) to give 0.8 g. of 1-[N-[3-(benzoylamino)-2-oxoheptyl]-N-[(phenylmethoxy)carbonyl]-L-alanyl]-L-proline, phenylmethyl ester.

(d) 1-[N-[3-(Benzoylamino)-2-oxoheptyl]-L-alanyl]-L-proline, monohydrochloride

1-[N-[3-(Benzoylamino)-2-oxoheptyl]-N-[(phenylmethoxy)carbonyl]-L-alanyl]-L-proline, phenylmethyl ester (0.96 g., 1.5 mmole) is dissolved in ethanol (75 ml.). Hydrochloric acid (1N,2 ml.) is added followed by palladium on carbon catalyst (10%, 200 mg.). The solution is stirred under an atmosphere of hydrogen overnight. The catalyst is filtered off, the ethanolic solution is evaporated, and the residue is dissolved in water and lyophilized to give 0.62 g. of 1-[N-[3-(benzoylamino)-2-oxoheptyl]-L-alanyl]-L-proline, monohydrochloride; m.p. 86°-123°; $[\alpha]_D^{23} = -62.9°$ (c=1.05, methanol). R$_f$ 0.57 (silica gel, n-butanol/acetic acid/water; 4:1:1).

Anal. calc'd. for $C_{22}H_{31}N_3O_5.HCl.2H_2O$: C, 53.85; H, 7.40; N, 8.57; Cl, 7.23. Found: C, 53.85; H, 7.20; N, 8.73; Cl, 7.29.

EXAMPLE 4

1-[N-[3-(Benzoylamino)-2-oxo-4-(3-pyridinyl)butyl]-L-alanyl]-L-proline, dihydrochloride (a) 2-(Benzoylamino)-3-(3-pyridinyl)-2-propenoic acid 2-Phenyl-4-(3-pyridinylmethylene)-5(4H)-oxazolone (3 g., 12 mmole) (see Griffith et al., J. Org. Chem., Vol. 29, p. 2659) is dissolved in acetic acid (24 ml.) and aqueous hydrochloric acid (0.5N, 150 ml.). The reaction mixture is stirred overnight at room temperature. It is evaporated and reevaporated from absolute ethanol. It is triturated with tetrahydrofuran, filtered, and the filtered solid is retriturated with absolute ethanol to yield 2.8 g. of 2-(benzoylamino)-3-(3-pyridinyl)-2-propenoic acid; m.p. 215°-216° (203°).

(b) 2-(Benzoylamino)-3-(3-pyridinyl)propanoic acid 2-(Benzoylamino)-3-(3-pyridinyl)-2-propenoic acid (14 g., 46 mmole) is dissolved in water (500 ml.) and hydrogenated using palladium on carbon catalyst (10%, 1.8 g.) overnight. The catalyst is filtered off, and the reaction mixture is evaporated to a small volume (100 ml.) and lyophilized to give 13.1 g. of product. The lyophilate is triturated with absolute ethanol-ether mixture and filtered to give 12 g. of 2-(benzoylamino)-3-(3-pyridinyl)propanoic acid; m.p. 99°-115°.

(c) 1-[N-[3-(Benzoylamino)-2-oxo-4-(3-pyridinyl)butyl]-N-[(phenylmethoxy)carbonyl]-L-alanyl]-L-proline, phenylmethyl ester 1-[N-(Carboxymethyl)-N-[(phenylmethoxy)carbonyl]-L-alanyl]-L-proline, phenylmethyl ester (6.2 g., 13.1 mmole), from Example 1(c), is dissolved in tetrahydrofuran (20 ml.) and the solution is stirred in an ice-bath. Oxalyl chloride is added followed by four drops of dimethylformamide. After stirring this reaction mixture in an ice bath for 20 minutes, it is then stirred at ambient temperature for an additional hour. The solvents are removed in vacuo and this residue is redissolved in tetrahydrofuran (20 ml.).

2-(Benzoylamino)-3-(3-pyridinyl)propanoic acid (4 g., 13 mmole) is suspended in tetrahydrofuran (45 ml.), and while stirring in an ice-bath, triethylamine (1.96 ml., 14 mmole) and dicyclohexylcarbodiimide (2.96 g., 14 mmole) are added. The reaction mixture is stirred at room temperature overnight. It is then filtered, and the filtrate evaporated to dryness. This residue is dissolved in tetrahydrofuran (30 ml.) and stirred in an ice bath. To this solution is added the above solution of 1-[N-(carboxymethyl)-N-[(phenylmethoxy)carbonyl]-L-alanyl]-L-proline, phenylmethyl ester, acid chloride in tetrahydrofuran (20 ml.). Triethylamine (1.9 ml., 13.6 mmole) is added, and the reaction mixture is stirred at room temperature overnight. It is filtered to remove triethylamine hydrochloride. The filtrate is evaporated in vacuo, redissolved in pyridine (15 ml.), 4-dimethylamino pyridine (65 mg.) is added, and the reaction mixture is stirred at room temperature for 3 hours. Acetic acid (16 ml.) is added and the reaction mixture is heated at 100° for 45 minutes. It is then evaporated, redissolved in ethyl acetate, and washed with aqueous sodium bicarbonate and water. After evaporation, the ethyl acetate extract is chromatographed over silica gel using ethyl acetate for elution to give 3.3 g. of 1-[N-[3-(benzoylamino)-2-oxo-4-(3-pyridinyl)butyl]-N-[(phenylmethoxy)carbonyl]-L-alanyl]-L-proline, phenylmethyl ester.

(d) 1-[N-[3-(Benzoylamino)-2-oxo-4-(3-pyridinyl)butyl]-L-alanyl]-L-proline, dihydrochloride The phenylmethyl ester product from part (c) (2.6 g., 3.84 mmole) is dissolved in ethanol (75 ml.) and aqueous hydrochloric acid (1N, 8 ml.) is added followed by palladium on carbon catalyst (10%, 0.6 g.). After hydrogenation for 16 hours, an additional 0.5 g. of catalyst is added and hydrogenation is continued for 6 more hours. The mixture is filtered, evaporated and combined with a similar reaction product obtained by hydrogenation of 0.8 g. of the ester product of part (c). The hydrogenated material is then chromatographed over LH-20 in water to obtain the homogeneous product. An aqueous solution of this material is treated with aqueous (hydrochloric acid (1N, 3 ml.) and the solution is lyophilized to give 1.0 g. of 1-[N-[3-(benzoylamino)-2-oxo-4-(3-pyridinyl)butyl]-L-alanyl]-L-proline, dihydrochloride; m.p. 120°–135°; $[\alpha]_D^{22} = -55.5°$ (c=1.1, methanol). $R_f$ 0.11 (silica gel; n-butanol/acetic acid/water; 4:1:1).

Anal. calc'd. for $C_{24}H_{28}N_4O_5 \cdot 2HCL \cdot 2H_2O$: C, 51.35; H, 5.75; N, 9.98; Cl, 12.63. Found: C, 51.35; H, 5.84; N, 9.96; Cl, 12.84.

EXAMPLE 5

1-[N-[3-(Benzoylamino)-4-(4-hydroxyphenyl)-2-oxobutyl]-L-alanyl]-L-proline, monohydrochloride (a) 2-Phenyl-4-[[4-(phenylmethoxy)phenyl]methyl]-5(4H)-oxazolone O-Benzyl-L-tyrosine (11.0 g., 40.5 mmole) is taken into 0.5N sodium hydroxide (81 ml.) and water (81 ml.) with vigorous stirring in an ice-bath. To this in five equal portions is added a total of 52 ml. of benzoyl chloride, 45 ml. of 1N sodium hydroxide and an additional 400 ml. of water over a 25 minute period. The bath is removed and the reaction is run for 2 hours at room temperature. The mixture is extracted twice with ethyl acetate. The aqueous portion is filtered, acidified with 1N hydrochloric acid and the crystals filtered to give 12.9 g. of N-benzoyl-O-benzyl-L-tyrosine; m.p. 166°–168° (162°).

This N-benzoyl-O-benzyl-L-tyrosine (12.76 g., 35 mmole) is taken into dry tetrahydrofuran (50 ml.) with stirring in an ice-bath. To this dicyclohexylcarbodiimide (7.7 g., 37.4 mmole) in tetrahydrofuran (18 ml.) is added dropwise. After 20 minutes, the ice-bath is removed and the reaction proceeds overnight at room temperature. The dicyclohexylurea is filtered off and the filtrate is concentrated to dryness. The crude product is crystallized from ether/hexane to give 10.26 g. of 2-phenyl-4-[[4-(phenylmethoxy)phenyl]methyl]-5(4H)-oxazolone; m.p. 85°–87° (83°).

(b) 1-[N-[3-(Benzoylamino)-2-oxo-4-[4-(phenylmethoxy)phenyl]butyl]-N-[(phenylmethoxy)carbonyl]-L-alanyl]-L-proline, phenylmethyl ester 1-[N-(Carboxymethyl)-N-[(phenylmethoxy)carbonyl]-L-alanyl]-L-proline, phenylmethyl ester (2.82 g., 6 mmole), from Example 1(c), is dissolved in tetrahydrofuran (20 ml.) and the solution is stirred in an ice-bath. Oxalyl chloride (0.63 ml., 7.2 mmole) is added followed by four drops of dimethylformamide. After stirring this reaction mixture in an ice-bath for 20 minutes, it is then stirred at ambient temperature for an additional hour. The solvents are removed in vacuo and the residue is redissolved in tetrahydrofuran (10 ml.) and cooled in an ice-bath. To this cold stirring solution is added a cold solution 2-phenyl-4-[[4-(phenylmethoxy)phenyl]methyl]-5(4H)-oxazolone (2.14 g., 6 mmole) in tetrahydrofuran (40 ml.). Triethylamine (0.84 ml., 6 mmole) is added and a basic atmosphere is maintained throughout the reaction by adding additional necessary amounts of triethylamine. The reaction mixture is stirred at ambient temperature overnight. It is then filtered and the filtrate is evaporated and redissolved in pyridine (7 ml.). 4-Dimethylamino pyridine (30 mg.) is added and the reaction mixture is stirred for 3 hours at room temperature. Acetic acid (7 ml.) is added and the reaction mixture is heated at 100° for 45 minutes. It is then evaporated, the residue is redissolved in ethyl acetate and washed with saturated sodium bicarbonate and dilute hydrochloric acid. The neutral ethyl acetate extract is evaporated and chromatographed over silica gel (300 g.) using the solvent system ethyl acetate:benzene (6.5:3.5) to give 2.7 g. of 1-[N-[3-(benzoylamino)-2-oxo-4-[4-(phenylmethoxy)phenyl]butyl]-N-[(phenylmethoxy)carbonyl]-L-alanyl]-L-proline, phenylmethyl ester.

(c) 1-[N-[3-(Benzoylamino)-4-(4-hydroxyphenyl)-2-oxobutyl]-L-alanyl]-L-proline, monohyrochloride The ester product from part (b) (1.8 g., 2.26 mmole) is dissolved in ethanol (150 ml.) containing aqueous hydrochloric acid (1N, 3.5 ml.). Palladium on carbon catalyst (10%, 500 mg.) is added and the solution is stirred under an atmosphere of hydrogen overnight. It is evaporated, dissolved in water, and lyophilized to give 1-[N-[3-(benzoylamino)-4-(4-hydroxyphenyl-2-oxobutyl]-L-alanyl]-L-proline, monohydrochloride; m.p. 118°–152°; $[\alpha]_D^{22} = -63.1°$ (c=1.07, methanol). $R_f$ 0.47 (silica gel, n-butanol/acetic acid/water; 4:1:1).

Anal. calc'd. for $C_{25}H_{29}N_3O_6 \cdot HCl \cdot H_2O$: C, 57.42; H, 6.16; N, 8.04; CL, 6.78. Found: C, 57.42; H, 6.03; N, 8.04; Cl, 7.11.

EXAMPLES 6–62

Following the procedure of Examples 1–3 and 5, the peptide ester shown in Col. I is treated to give the carboxymethyl peptide ester shown in Col. II. Conversion to its acid chloride and further reaction with the oxazolone of Col. III yields the N-protected ester product of Col. IV. Removal of the N-protecting group and the ester group yields the final product of Col. V wherein $R_6$ is hydrogen.
Col. I
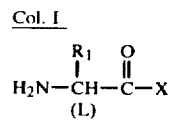
Col. II
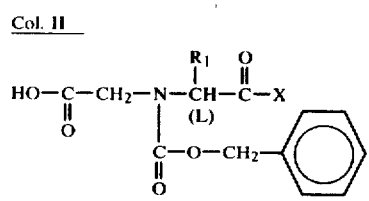
Col. III
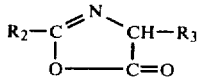
Col. IV
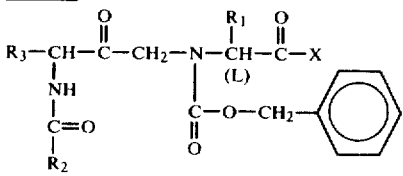
Col. V
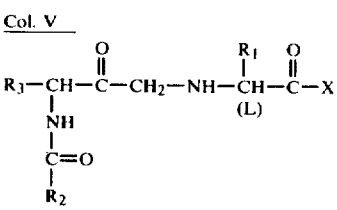

| Example | R₁ | R₂ | R₃ | X |
|---|---|---|---|---|
| 6 | H₅C₂— | 3-Cl-C₆H₄-CH₂— | C₆H₅-CH₂— | -N(CH₂-CH(OH)-CH₂-)CH(COOCH₂C₆H₅)(H) (L) |
| 7 | H₃C— | C₆H₅-CH₂— | H— | -N(CH₂-CH(OC(CH₃)₃)-CH₂-)CH(COOCH₂C₆H₅)(H) (L) |
| 8 | F₃C— | cyclohexyl-(CH₂)₂— | C₆H₅-CH₂— | -N(CH₂-CH(CH₂-C₆H₄-4-F)-CH₂-)CH(COOCH₂C₆H₅)(H) (L) |
| 9 | Cl₃CH₂C— | C₆H₅-CH₂— | C₆H₅— | -N(CH₂-CH(S-CH₂-C₆H₅)-CH₂-)CH(COOC(CH₃)₃)(H) (L) |
| 10 | C₆H₅-CH₂— | C₆H₅-CH₂— | C₆H₅-(CH₂)₂— | -N(CH₂-CH(N₃)-CH₂-)CH(COOCH₂C₆H₅)(H) (L) |

-continued

| Example | R₁ | R₂ | R₃ | X |
|---|---|---|---|---|
| 11 | H₃C— | phenyl | —CH₂—phenyl | —N(H)—CH(CH₂-phenyl)(CH₂-phenyl)-COOCH₂-phenyl (L) |
| 12 | H₃C—(CH₂)₃— | phenyl | —CH₂—phenyl | —N(H)—CH(CH₂-phenyl)(CH₂-phenyl)-COOCH₂-phenyl (L) |
| 13 | H₅C₂— | 2-thienyl | —CH₂—phenyl | —N(H)—CH(CH₂-CF₃)-COOCH₂-phenyl (L) |
| 14 | H₃C— | 2-furyl-CH₂— | —(CH₂)₂—phenyl | —N(H)—CH(CH₂—C(CH₃)(OCH₃)₂)-COOCH₂-phenyl (L) |
| 15 | H₃C—(CH₂)₂— | 2-piperidyl | —CH₂—phenyl | —N(H)—CH(CH₂—C(CH₃)(O-O cyclic))-COOCH₂-phenyl (L) |

-continued

| Example | R₁ | R₂ | R₃ | X |
|---|---|---|---|---|
| 16 | H₃C— | phenyl | benzyl (–CH₂–C₆H₅) | dithiolane-CH₂–C(COOCH₂Ph)(H)–N– (L) |
| 17 | F₃C— | 4-methoxyphenyl | 4-fluorobenzyl | dithiolane-CH₂–C(COOCH₂Ph)(H)–N– (L) |
| 18 | H₃C— | phenyl | 2-thienyl | –NH–C(=O)–C₂H₅ substituted CH₂–C(COOCH₂Ph)(H)–N– (L) |
| 19 | H₃C— | phenyl | furyl–(CH₂)₂– | ketone-substituted CH₂–C(COOCH₂Ph)(H)–N– (L) |
| 20 | C₆H₅–CH₂–OCH₂– | phenyl | 4-pyridylmethyl | 4-biphenyloxy-CH₂–C(COOCH₂Ph)(H)–N– (L) |

-continued

| Example | R₁ | R₂ | R₃ | X |
|---|---|---|---|---|
| 21 | C₆H₅CH₂— | H₃C— | H₃C— | —NH—CH(CH₂CH(CH₃)₂)—COOCH₂—C₆H₅ (L) |
| 22 | H₅C₂— | 2-thienyl | H₃C— | naphthyloxy-CH₂-CH(CH₂-N<)-COOCH₂-C₆H₅ (L), H |
| 23 | H₃C— | furfuryl (2-furyl-CH₂—) | H₅C₂— | (CH₃)₂N-C(=O)-O-CH(CH₂-N<)-COOCH₂-C₆H₅ (L), H |
| 24 | H₃C— | C₆H₅— | H₃C—(H₂C)₃— | 2-thienyl-CH₂-CH(CH₂-N<)-COOCH₂-C₆H₅ (L), H |
| 25 | H₃C— | C₆H₅— | F₃C— | C₆H₅-CH₂-O-CH(CH₂-N<)-COOCH₂-C₆H₅ (L), H |

-continued

| Example | R₁ | R₂ | R₃ | X |
|---|---|---|---|---|
| 26 | F₃C— | phenyl | phenyl-(CH₂)₃— | —N-(CH₂)₃-CH(SPh)-CH(H)-COOC(CH₃)₃ (L) |
| 27 | H₃C— | pyridyl | phenyl-CH₂— | —N-CO-CH₂-CH(H)-COOCH₂Ph (L) |
| 28 | H₅C₂— | phenyl-(CH₂)₃— | phenyl | —N-CH₂-CH(Ph)-CH₂-CH(H)-COOCH₂Ph (L) |
| 29 | H₃C— | phenyl | phenyl-(CH₂)₄— | —N-CH₂-CH₂-S-CH(H)-COOCH₂Ph (L) |
| 30 | H₃C— | phenyl | phenyl-(CH₂)₃— | —N-CH₂-CH=CH-CH(H)-COOCH₂Ph (L) |
| 31 | H₃C— | phenyl | 4-(H₃CS)-phenyl-CH₂— | —N-(pyridyl)-CH(H)-COOCH₂Ph (L) |
| 32 | H₅C₂— | thienyl | phenyl-CH₂— | —N-CH₂-CH₂-CH(H)-COOCH₂Ph (L) |

| Example | R₁ | R₂ | R₃ | X |
|---|---|---|---|---|
| 33 | H₃C— | phenyl | benzyl | β-carboline-3-carboxylic acid benzyl ester (L) |
| 34 | H₅C₂— | benzyl | 4-pyridylmethyl | 1,2,3,4-tetrahydroisoquinoline-3-COOCH₂Ph (L) |
| 35 | H₃C— | benzyl | 2-pyridylmethyl | 1,2,3,4-tetrahydroisoquinoline-3-COOCH₂Ph (L) |
| 36 | O₂N—NH—C(=NH)—HN—(H₂C)₃— | phenyl | benzyl | pipecolic acid benzyl ester (L) |
| 37 | PhCH₂OCOHN(H₂C)₄— | phenyl | benzyl | 1,3-dithiolane-2-spiro-proline benzyl ester (L) |

-continued

| Example | R₁ | R₂ | R₃ | X |
|---|---|---|---|---|
| 38 | 4-benzyloxybenzyl | phenyl | benzyl | N-[1-(benzyloxycarbonyl)-3-phenylpropyl]amino (L,H) |
| 39 | 3-benzyloxy-4-benzyloxybenzyl | thienyl (2-) | phenethyl | N-[1-(benzyloxycarbonyl)butyl]amino (L,H) |
| 40 | indol-3-ylmethyl | piperidin-2-yl | benzyl | N-[1-(benzyloxycarbonyl)butyl]amino (L,H) |
| 41 | 1-benzyl-imidazol-4-ylmethyl | benzyl | thienyl-2-methyl | N-[1-(benzyloxycarbonyl)-naphth-2-yl-methyl]amino (L,H) |
| 42 | $CH_3-S-(CH_2)_2-$ | phenyl | 3-phenylpropyl | N-[1-(benzyloxycarbonyl)butyl]amino (L,H) |

| Example | R₁ | R₂ | R₃ | X |
|---|---|---|---|---|
| 43 | H₃C— | phenyl | O₂N—HN—C(=NH)—HN—(H₂C)₃— | -N(pyrrolidine)-CH(COOCH₂-phenyl)(L)-H |
| 44 | H₃C— | phenyl | 4-H₂CO-phenyl-CH₂— with 2-(phenyl-H₂CO)- substituent | -N(pyrrolidine)-CH(COOCH₂-phenyl)(L)-H |
| 45 | H₃C— | phenyl | indol-3-yl-CH₂— | -N(thiazolidine)-CH(COOCH₂-phenyl)(L)-H |
| 46 | H₃C— | phenyl | phenyl-CH₂— | —NH—CH₂—COOCH₂-phenyl |
| 47 | F₃C— | pyridyl | phenyl-(CH₂)₄— | —NH—CH(CH₃)(L)—COOCH₂-phenyl |
| 48 | phenyl-H₂C— | phenyl | H— | —NH—CH(CH₂CH(CH₃)₂)(L)—COOCH₂-phenyl |

-continued

| Example | $R_1$ | $R_2$ | $R_3$ | X |
|---|---|---|---|---|
| 49 | $H_5C_2-$ | phenyl | furfuryl ($CH_2$-furan) | $-NH-CH(CH_2^{(L)})-COOCH_2-C_6H_5$ with side chain $-CH_2-C_6H_4-OCH_2-C_6H_5$ (para) |
| 50 | $H_3C-$ | phenyl | benzyl | $-NH-CH(CH_2^{(L)})-COOCH_2-C_6H_5$ with side chain $-CH_2-C_6H_3(OCH_2-C_6H_5)_2$ (3,4-di) |
| 51 | $H_3C-$ | phenyl | benzyl | $-NH-CH(CH_2^{(L)})-COOCH_2-C_6H_5$ with side chain $-CH_2$-indol-3-yl (NH) |

-continued

| Example | R₁ | R₂ | R₃ | X |
|---|---|---|---|---|
| 52 | PhCH₂— | Ph | 2-pyridyl-CH₂— | —NH—CH(CH₂(L))—COOCH₂Ph, with CH₂ group as N=/N— diazole attached to CH₂Ph |
| 53 | H₃C— | Ph | H₃C—(H₂C)₅— | —NH—CH((CH₂)₄—NHCOCH₂Ph)—COOCH₂Ph |
| 54 | H₃C— | Ph | 2-thienyl | —NH—CH(CH₂(L)—S—CH₂Ph)—COOCH₂Ph |
| 55 | H₃C₂— | PhCH₂— | PhCH₂— | —NH—CH((CH₂)₃NHC(=NH)NHNO₂ (L))—COOCH₂Ph |
| 56 | H₃C— | Ph | PhCH₂— | —NH—CH((CH₂)₂—C(=O)NH₂ (L))—COOCH₂Ph |

-continued

| Example | R₁ | R₂ | R₃ | X |
|---|---|---|---|---|
| 57 | H₃C— | phenyl | benzyl (–CH₂–C₆H₅) | lysine derivative, α-NH attached to main chain C(=O)– (L), side chain ε-N– linked to –C(=O)–CH(cyclohexyl)–O–C(=O)–O–C₂H₅ |
| 58 | H₃C— | phenyl | benzyl (–CH₂–C₆H₅) | (1,3-dithiolan-2-yl)methyl amino acid (L), ε-N– linked to –C(=O)–CH(CH(CH₃)₂)–O–C(=O)–O–C₂H₅ |
| 59 | H₃C— | 2-pyridyl | 3-phenylpropyl (–(CH₂)₃–C₆H₅) | α-amino acid with –CH₂–CH(S–C₆H₅)– side chain (L), ε-N– linked to –C(=O)–CH(CH₃)–O–C(=O)–O–C₂H₅ |
| 60 | F₃C— | phenyl | 2-(thien-2-yl)ethyl (–(CH₂)₂–thiophene) | lysine (L), ε-N– linked to –C(=O)–CH₂–O–C(=O)–O–C(CH₃)₃ |
| 61 | H₃C— | phenyl | 4-chlorobenzyl (–CH₂–C₆H₄–Cl) | lysine (L), ε-N– linked to –C(=O)–CH₂–O–C(=O)–C₆H₅ |
| 62 | H₃C—(H₂C)₃— | phenyl | benzyl (–CH₂–C₆H₅) | lysine (L), ε-N– linked to o-(benzoyloxy)benzoyl (phthalide-type) ester |

The R₁ protecting groups in Examples 20, 36 to 39 and 41, the R₃ protecting groups in Examples 43 and 44, and the R₅ protecting groups in Examples 49, 50, and 52 to 55 are removed as the last step in the synthesis. The R₆ ester groups shown in Examples 57 to 62 are not removed.

EXAMPLE 63

1-[N-[(S)-3-(Benzoylamino)-2-oxo-4-phenylbutyl]-L-alanyl]-L-proline, monohydrochloride (a) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperature for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°–179°.

(b) (S)-N-[3-Chloro-2-oxo-1-(phenylmethyl)propyl]benzamide (S)-3-Amino-1-chloro-4-phenyl-2-butanone, hydrogen bromide (36.3 g., 130.3 mmole) is suspended in 520 ml. of dry tetrahyrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]benzamide; m.p. (160°) 170°–172° (dec.); $[\alpha]_D^{23} = -129$ (c 1.7, dimethylformamide).

(c) 1-[N-[(S)-3-(Benzoylamino)-2-oxo-4-phenylbutyl]-L-alanyl]-L-proline, 1,1-dimethylethyl ester L-Alanyl-L-proline, 1,1-dimethylethyl ester (2.42 g., 10 mmole), sodium bicarbonate (840 mg.) and (S)-N-[3-chloro-2-oxo-1-(phenylmethyl)propyl]benzamide (3.01 g.) are combined in 50 ml. of dimethylformamide under an argon atmosphere at room temperature with stirring overnight. The reaction mixture is then concentrated in vacuo to about half its original volume and the residue is taken up in ethyl acetate and washed with saturated sodium bicarbonate to give 2.25 g. of crude product. This material is taken up in ethyl acetate:methanol (95:5) and applied to a silica gel column (135 g.) and eluted with ethyl acetate:methanol (95:5) to give 860 mg. of 1-[N-[(S)-3-(benzoylamino)-2-oxo-4-phenylbutyl]-L-alanyl]-L-proline, 1,1-dimethylethyl ester.

(d) 1-[N-[(S)-3-(Benzoylamino)-2-oxo-4-phenylbutyl]-L-alanyl]-L-proline, monohydrochloride 1-[N-[(S)-3-(Benzoylamino)-2-oxo-4-phenylbutyl]-L-alanyl]-L-proline, 1,1-dimethylethyl ester (740 mg., 1.46 mmole) is dissolved in a solution of hydrogen chloride in acetic acid (1.5N, 10 ml.) and kept at room temperature for 30 minutes. It is then concentrated, taken into water, filtered and lyophilized to obtain 600 mg. of 1-[N-(S)-3-(benzoylamino)-2-oxo-4-phenylbutyl]-L-alanyl]-L-proline, monohydrochloride; m.p. 83°–163°; $[\alpha]_D^{25} = -109°$ (c=1.04, methanol). R$_f$ 0.6 (silica gel; butanol/acetic acid/water, 4:1:1).

Anal. calc'd. for $C_{25}H_{29}N_3O_5 \cdot HCl \cdot 1.65H_2O$: C, 57.99; H, 6.48; N, 8.12; Cl, 6.85. Found: C, 57.99; H, 6.39; N, 8.09; Cl, 6.95.

EXAMPLE 64

(S)-1-[N²-[3-(Benzoylamino)-2-oxo-4-phenylbutyl]-L-lysyl]-L-proline, dihydrochloride (a) 1-[N⁶-[(1,1-Dimethylethoxy)carbonyl]-N²-[(phenylmethoxy)carbonyl]-L-lysyl]-L-proline, 1,1-dimethylethyl ester N⁶-[(1,1-Dimethylethoxy)carbonyl]-N²-[(phenylmethoxy)carbonyl]-L-lysine (9.51 g.) and hydroxybenzotriazole (3.825 g.) are taken into 25 ml. of dimethylformamide with stirring in an ice-bath under an argon atmosphere. To this is added L-proline, 1,1-dimethylethyl ester (4.49 g.) followed by N,N'-diisopropylethylamine (2.2 ml.) and dicyclohexylcarbodiimide (5.15 g.). After 15 minutes the bath is removed and the reaction is allowed to proceed for 6.5 hour at room temperature. The dimethylformamide is removed in vacuo. The residue is taken into ethyl acetate and the dicyclohexylurea is filtered off. The filtrate is washed neutral with 10% potassium bisulfate and saturated sodium bicarbonate. The crude product (13.26 g.) is purified on silica gel column eluting with ethyl acetate:hexane (2:1) to give 13.0 g. of 1-[N⁶-[(1,1-dimethylethoxy)carbonyl]-N²-[(phenylmethoxy)carbonyl]-L-lysyl]-L-proline, 1,1-dimethylethyl ester.

(b) (S)-1-[N²-[3-(Benzoylamino)-2-oxo-4-phenylbutyl]-N⁶-[(1,1-dimethylethoxy)carbonyl]-L-lysyl]-L-proline, 1,1-dimethylethyl ester The ester product from part (a) is reduced in ethanol with palladium on carbon catalyst (10%) to yield 3.99 g. of 1-[N⁶-[1,1-dimethylethoxy)carbonyl]-L-lysyl]-L-proline, 1,1-dimethylethyl ester. This material is taken into 40 ml. of dimethylformamide and treated with (S)-N-[3-chloro-2-oxo-1-(phenylmethyl)propyl]benzamide (3.01 g.), from Example 63(b), and sodium bicarbonate (840 mg.). After stirring for 18 hours at room temperature, the reaction mixture is concentrated in vacuo, taken into ethyl acetate and washed with saturated sodium bicarbonate. The crude product (7.0 g.) is purified on a silica gel column eluting with ethyl acetate:1% methanol to give 1.7 g. of (S)-1-[N²-[3-(benzoylamino)-2-oxo-4-phenylbutyl]-N⁶-[(1,1-dimethylethoxy)carbonyl]-L-lysyl]-L-proline, 1,1-dimethylethyl ester.

(c) (S)-1-[N²-[3-(Benzoylamino)-2-oxo-4-phenylbutyl]-L-lysyl]-L-proline, dihydrochloride The ester product from part (b) (1.6 g.) is treated for 30 minutes at room temperature with 20 ml. of 1.5N hydrochloric acid:acetic acid, concentrated to dryness, and triturated to a solid with ether to give 1.37 g. of crude product. This material is taken into water, millipore filtered, and lyophilized to give 1.28 g. of product. Further purification is performed on an LH20 column in water to give 740 mg. of (S)-1-[N²-[3-(benzoylamino)-2-oxo-4-phenylbutyl]-L-lysyl]-L-proline, dihydrochloride; m.p. 120°–180°; $[\alpha]_D^{25} = -84.8°$ (c=1.05, methanol). R$_f$ 0.61 (trace at 0.9) (silica gel, chloroform/methanol/acetic acid, 60, 40, 38% 20).

Anal. calc'd. for $C_{28}H_{36}N_4O_5 \cdot 2HCl \cdot 3H_2O$: C, 52.98; H, 6.98; N, 8.83; Cl, 11.17. Found: C, 52.98; H, 6.93; N, 8.66; Cl, 11.31.

EXAMPLE 65

N-[N-[[(S)-3-(Benzoylamino)-2-oxo-4-phenylbutyl]-L-alanyl]-N-cyclohexylglycine, monohydrochloride (a) N-Cyclohexylglycine, 1,1-dimethylethyl ester Cyclohexylamine (70.35 ml.) and sodium bicarbonate (12.9 g.) are suspended with stirring in 200 ml. of absolute ethanol while stirring in an ice-bath. To this is added bromoacetic acid, 1,1-dimethylethyl ester (20.78 ml.) dropwise. The ice-bath is removed. After 24 hours at room temperature, the reaction mixture is concentrated to dryness, taken into chloroform and washed with water. The crude product (42 g.) is chromatographed on silica gel eluting with ethyl acetate:hexane (2:1) to give 27.4 g. of N-cyclohexylglycine, 1,1-dimethylethyl ester.

(b) N-Cyclohexyl-N-[N-[(phenylmethoxy)carbonyl]-L-alanyl]glycine, 1,1-dimethylethyl ester N-[(Phenylmethoxy)carbonyl]-L-alanine (4.46 g.), N-cyclohexylglycine, 1,1-dimethylethyl ester (4.26 g.), hydroxybenzotriazole (3.06 g.), dicyclohexylcarbodiimide (4.12 g.) and triethylamine (2.8 ml.) are stirred in 40 ml. of dimethylformamide at room temperature for 20 hours. The reaction mixture is then concentrated in vacuo, taken into ethyl acetate, the dicyclohexylurea is filtered off, and the filtrate is washed neutral with 10% potassium bisulfate and saturated sodium bicarbonate to give 5.9 g. of crude product. Crystallization from ether:hexane yields 3.97 g. of N-cyclohexyl-N-[N-[(phenylmethoxy)carbonyl]-L-alanyl]glycine, 1,1-dimethylethyl ester; m.p. 104°–105°.

(c) N-(L-Alanyl)-N-cyclohexylglycine, 1,1-dimethylethyl ester

The ester product from part (b) (3.9 g.) is taken into methanol with palladium on carbon catalyst (10%, 700 mg.) and stirred under hydrogen atmosphere for 4 hours. The reaction mixture is filtered and concentrated to dryness to give 2.65 g. of crude N-(L-alanyl)-N-cyclohexylglycine, 1,1-dimethylethyl ester.

(d) N-[N-[[(S)-3-(Benzoylamino)-2-oxo-4-phenylbutyl]-L-alanyl]-N-cyclohexylglycine, 1,1-dimethylethyl ester The crude ester product from part(c) (2.6 g.), sodium bicarbonate (764 mg.), and (S)-N-[3-chloro-2-oxo-1-(phenylmethyl)propyl]benzamide (2.75 g.), from Example 63(b), are stirred for 20 hours in 25 ml. of dimethylformamide. The reaction mixture is concentrated to dryness, taken into ethyl acetate, and washed with saturated sodium carbonate to give 4.7 g. of crude product. Purification on a silica gel column eluting with ethyl acetate:methanol (99:1) yields 1.5 g. of N-[N-[[(S)-3-(benzoylamino)-2-oxo-4-phenylbutyl]-L-alanyl]-N-cyclohexylglycine, 1,1-dimethylethyl ester.

(e) N-[N-[[(S)-3-(Benzoylamino)-2-oxo-4-phenylbutyl]-L-alanyl]-N-cyclohexylglycine, monohydrochloride The ester product from part(d) (500 mg.) is treated for 30 minutes with 5 ml. of 1.5N hydrochloric acid:acetic acid and then concentrated to dryness at room temperature. The crude product is taken into methanol and purified on an LH20 column to yield 413 mg. of product. This is made semi-crystalline in acetonitrile:ether to give N-[N-[[(S)-3-(benzoylamino)-2-oxo-4-phenylbutyl]-L-alanyl]-N-cyclohexylglycine, monohydrochloride; m.p. 154°–157° (132°); $[\alpha]_D^{23} = -67.4°$ (c=1.35, methanol). $R_f$ 0.60 (minor impurity at 0.92) (silica gel, chloroform:methanol:conc. ammonia, 30:10:2).

Anal. calc'd. for $C_{28}H_{35}N_3O_5 \cdot HCl \cdot H_2O$ C, 61.35; H, 6.99; N, 7.67; Cl, 6.47. Found: C, 61.08; H, 6.79; N, 7.65; Cl, 6.46.

EXAMPLE 66

N-[N-[[(S)-3-(Benzoylamino)-2-oxo-4-phenylbutyl]-L-alanyl]-N-phenylglycine, monohydrochloride (a) N-Phenylglycine, 1,1-dimethylethyl ester A solution of triethylamine (11.25 g., 0.11 mole) and aniline (9.3 g., 0.10 mole) in ether (100 ml.) under an argon atmosphere is cooled to 0° in an ice-bath. To this is added bromoacetic acid, 1,1-dimethylethyl ester (18 g., 0.093 mole) over a period of 30 minutes. The resulting mixture is stirred at 0° for one hour, then warmed to room temperature, and stirred overnight. The solution is filtered and rinsed with ether and the filtrate concentrated to yield 6.9 g. of a yellow oil. $R_f$ 0.6, 0.7 (silica gel, ethyl acetate). Chromatography on LPS-1 using hexane:ethyl acetate (7:3) as eluant gives 2.3 g. of N-phenylglycine, 1,1-dimethylethyl ester as a pale yellow liquid. $R_f$ 0.7 (silica gel, ethyl acetate).

(b) N-Phenyl-N-[N-[(phenylmethoxy)carbonyl]-L-alanyl]glycine, 1,1-dimethylethyl ester A solution of N-[(phenylmethoxy)carbonyl]-L-alanine (2.8, 12.7 mmole) in dry tetrahydrofuran (50 ml.) under argon is cooled in a dry ice-ethanol bath. To this is added N-methylmorpholine (1.28 g., 12.7 mmole) and isobutylchloroformate (1.73 g., 12.7 mmole). After 20 minutes N-phenylglycine, 1,1-dimethylethyl ester (3.7 g., 12.7 mmole) is added. The resulting mixture is stirred at −20° for one hour, then at room temperature overnight. The mixture is partitioned between ethyl acetate and 1N hydrochloric acid. The organic layer is washed successively with 1N hydrochloric acid and 10% sodium bicarbonate, dried (MgSO$_4$), and concentrated. Chromatography on LPS-1 eluting with a gradient of ethyl acetate:hexane (3:1→1:1) gives 4.0 g. of N-phenyl-N-[N-[(phenylmethoxy)carbonyl]-L-alanyl]glycine, 1,1-dimethylethyl ester as a clear oil. R$_f$ 0.4 (silica gel, ethyl acetate).

(c) N-(L-Alanyl)-N-phenylglycine, 1,1-dimethylethyl ester

A solution of the ester product from part (b) (4.0 g., 9.7 mmole) in ethanol (125 ml.) and 10% palladium on carbon catalyst is stirred under a follow of hydrogen for 18 hours. The solution is filtered, concentrated, dissolved in ethyl acetate and extracted with 1N hydrochloric acid. The aqueous layer is treated with sodium bicarbonate until basic and extracted with ethyl acetate. The combined ethyl acetate extracts are dried (MgSO$_4$) and concentrated to give 1.3 g. of N-(L-alanyl)-N-phenylglycine, 1,1-dimethylethyl ester as a white solid. R$_f$ 0.52, minor spot at 0.64 (silica gel, ethyl acetate:methanol; 1:1).

(d) N-[N-[[(S)-3-(Benzoylamino)-2-oxo-4-phenylbutyl]-L-alanyl]-N-phenylglycine, 1,1-dimethylethyl ester To a stirring solution of (S)-N-[3-chloro-2-oxo-1-(phenylmethyl)propyl]benzamide (1.4 g., 4.7 mmole), from Example 63(b), and N-(L-alanyl)-N-phenylglycine, 1,1-dimethylethyl ester (1.3 g., 4.7 mmole) in dry dimethylformamide is added sodium bicarbonate (0.38 g., 4.7 mmole) and sodium iodide (0.7 g., 4.7 mmole). After stirring overnight at room temperature, the mixture is concentrated, dissolved in ethyl acetate and filtered. The filtrate is washed with 10% sodium bicarbonate, dried (MgSO$_4$), and concentrated to a yellow oil. Chromatography on LPS-1 eluting with a gradient of ethyl acetate:hexane (1:1) to ethyl acetate gives 1.8 g. of N-[N-[[(S)-3-(benzoylamino)-2-oxo-4-phenylbutyl]-L-alanyl]-N-phenylglycine, 1,1-dimethylethyl ester. $R_f$ 0.34 (silica gel, ethyl acetate).

(e) N-[N-[[(S)-3-(Benzoylamino)-2-oxo-4-phenylbutyl]-L-alanyl]-N-phenylglycine, monohydrochloride A solution of the ester product from part (d) (1.6 g., 2.9 mmole) in hydrochloric acid/acetic acid (1.77N, 17.0 ml.) is stirred at room temperature for 30 minutes. The solution is concentrated and the residue is triturated with ether to give a pale yellow solid. Recrystallization from methanol/ether gives 0.84 g. of N-[N-[[(S)-3-(benzoylamino)-2-oxo-4-phenylbutyl]-L-alanyl]-N-phenylglycine, monohydrochloride as a white, crystalline solid, m.p. 147°–159° (dec.). $R_f$ 0.8 (silica gel, butanol:acetic acid:water; 1:1:1). $[\alpha]_D = -12.7°$ (c=1.5, methanol).

Anal. calc'd. for $C_{28}H_{29}N_3O_5 \cdot HCl \cdot 0.65H_2O$: C, 62.77; H, 5.89; N, 7.84; Cl, 6.62. Found: C, 62.77; H, 5.70; N, 7.84; Cl, 6.12.

EXAMPLE 67

(S)-1-[N-[[3-(Benzoylamino)-2-oxo-4-phenylbutyl]-N-methyl-L-alanyl]-L-proline, monohydrochloride (a) N-[(Phenylmethoxy)carbonyl]-L-alanine L-Alanine (89.1 g., 1 mole) is dissolved in 2N sodium hydroxide (500 ml.) and chilled to 0°. To this is added simultaneously dropwise over a one hour period benzylchloroformate (204.5 g., 1.2 mole) and 4N sodium hydroxide (250 ml.). The reaction mixture is stirred overnight (0° to room temperature), and washed with ethyl acetate (2×500 ml.). The aqueous portion is acidified to pH 2.0 with 6N hydrochloric acid and extracted with ethyl acetate (3×600 ml.). The combined ethyl acetate extracts are dried (Na₂SO₄), concentrated on a rotary evaporator, and the solid residue is triturated with petroleum ether to give 194.0 g. of N-[(phenylmethoxy)carbonyl]-L-alanine as a white solid.

(b) N-Methyl-N-[(phenylmethoxy)carbonyl]-L-alanine

To a cold (0°) solution of N-[(phenylmethoxy)carbonyl]-L-alanine (22.3 g., 0.1 mole) and methyl iodide (50 ml., 0.8 mole) in tetrahydrofuran (250 ml.) is added sodium hydride dispersion (14.25 g., 0.3 mole) cautiously with gentle stirring. The suspension is stirred overnight under a nitrogen atmosphere (0°→room temperature), slowly poured into saturated sodium bicarbonate (200 ml.), diluted with ethyl acetate (300 ml.) and the layers separated. The organic layer is extracted once more with saturated sodium bicarbonate. The combined aqueous layers are acidified to pH 2.0 with 10% potassium bisulfate and extracted with ethyl acetate. The combined ethyl acetate extracts are dried (Na₂SO₄) and concentrated in vacuo into a dark oily residue (23.0 g.).

This crude acid is treated with dicyclohexylamine (20 ml.) in ether (150 ml.). The resulting crude dicyclohexylamine salt is collected (37.0 g.), recrystallized from chloroform/ether (35.0 g.), and converted back to the acid by partitioning between 1N hydrochloric acid/ethyl acetate, yielding a pale yellow oil, which crystallizes on standing (17.4 g.).

Recrystallization (11.2 g.) from ethyl acetate/petroleum ether gives 4.0 g. of N-methyl-N-[(phenylmethoxy)carbonyl]-L-alanine as a white crystalline product; m.p. 65°–66.5°; $[\alpha]_D^{25} = -31.1°$ (c=2, acetic acid).

(c) 1-[N-Methyl-N-[(phenylmethoxy)carbonyl]-L-alanyl]-L-proline, 1,1-dimethylethyl ester To a solution of N-methyl-N-[(phenylmethoxy)carbonyl]-L-alanine (4.74 g., 20 mmole) in distilled tetrahydrofuran (50 ml.) is added L-proline, 1,1-dimethylethyl ester (3.42 g., 20 mmole), hydroxybenzotriazole hydrate (3.06 g., 20 mmole) and dicyclohexylcarbodiimide (4.12 g., 20 mmole). The reaction mixture is stirred overnight, the precipitated dicyclohexylurea is filtered off, and the filtrate is concentrated. The residue is dissolved in ethyl acetate (50 ml.) and washed with saturated sodium bicarbonate (twice), 10% potassium bisulfate (twice), and water (twice), dried (Na₂SO₄), and concentrated to give 6.4 g. of 1-[N-methyl-N-[(phenylmethoxy)carbonyl]-L-alanyl]-L-proline,1,1-dimethylethyl esters as an oily residue.

(d) 1-(N-Methyl-L-alanyl)-L-proline, 1,1-dimethylethyl ester

A mixture of the ester product from part (c) (6.4 g., 16.4 mmole) and 0.8 g. of 10% palladium on carbon catalyst in ethanol (95%, 150 ml.) is hydrogenated at atmospheric pressure overnight. The catalyst is removed by filtration and the filtrate is evaporated. The resulting oily residue solidfies upon drying in high vacuum into an oily solid residue (3.8 g.). Trituration with ether affords 1.5 g., of 1-(N-methyl-L-alanyl)-L-proline, 1,1-dimethylethyl ester, monohydrochloride as a white solid; $R_f$ 0.44 (silica gel, 20% methanol/chloroform). $[\alpha]_D^{25} = -102.1°$ (c=2, acetic acid).

The ether filtrate affords 2.3 g. of 1-(N-methyl-L-alanyl)-L-proline, 1,1-dimethylether ester as an oil; $R_f$ 0.44 (silica gel, 20% methanol/chloroform). $[\alpha]_D^{25} = -101.6°$ (c=2, acetic acid)

(e) (S)-1-[N-[[3-(Benzoylamino)-2-oxo-4-phenylbutyl]-N-methyl-L-alanyl]-L-proline, 1,1-dimethylethyl ester A reaction mixture of 1-(N-methyl-L-alanyl)-L-proline, 1,1-dimethylethyl ester (2.1 g., 8.19 mmole), (S)-N-[3-chloro-2-oxo-1-(phenylmethyl)propyl]benzamide (2.46 g., 8.19 mmole), from Example 63(b), excess sodium bicarbonate, and sodium iodide (1.22 g., 8.10 mmole) in dimethylformamide (15 ml.) is stirred at room temperature overnight under a nitrogen atmosphere. The reaction mixture is concentrated, the residue is partitioned between water/ethyl acetate, the layers are separated, and the aqueous layer is extracted once more with ethyl acetate. The combined organic extracts are washed with saturated sodium bicarbonate and water, dried (Na₂SO₄), and concentrated into an oily residue (3.5 g.). Flash chromatography (200 g. silica gel, 1% methanol/ethyl acetate) affords 2.8 g. of (S)-1-[N-[[3-(benzoylamino)-2-oxo-4-phenylbutyl]-N-methyl-L-alanyl]-L-proline, 1,1-dimethylethyl ester as a yellow oil.

(f) (S)-1-[N-[[3-(Benzoylamino)-2-oxo-4-phenylbutyl]-N-methyl-L-alanyl]-L-proline, monohydrochloride The ester product form part (e) (1.4 g., 2.7 mmole) is treated with 2N hydrochloric acid/acetic acid (20 ml.). After stirring for 2 hours at room temperature, the reaction mixture is concentrated under reduced pressure and the resulting oily residue is triturated with ether (four times) to give 1.05 g. of (S)-1-[N-[[3-(benzoylamino)-2-oxo-4-phenylbutyl]-N-methyl-L-alanyl]-L-proline, monohydrochloride as an off-white solid; m.p. 125°–135°; $R_f$ 0.24 (silica gel, n-butanol/acetic acid/water; 4:1:1). $[\alpha]_D^{25} = -87°$ (c=1, methanol).

Anal. calc'd. for $C_{26}H_{31}N_3O_5 \cdot HCl \cdot 0.7H_2O$: C, 60.68; H, 6.41; N, 8.16; Cl, 6.88. Found: C, 60.68; H, 6.36; N, 7.95; Cl, 6.48.

EXAMPLE 68

(S)-1-[N-[3-(Benzoylamino)-2-oxo-4-phenylbutyl]-4-phenylglycyl]-L-proline, hydrochloride (20:3)

(a) 1-(Bromoacetyl)-L-proline, 1,1-dimethylethyl ester

To a chilled (−10°) solution of L-proline, 1,1-dimethylethyl ester (34.2 g., 0.2 mole) in methylene chloride (250 ml.) is added diisopropylethylamine (38.3 ml., 0.22 mole) and bromoacetyl chloride (16.5 ml., 0.2 mole) dropwise over a 20 minute period while keeping the temperature between −10° to −5°. The dark reaction mixture is stirred overnight (−10° to room temperature) and concentrated under reduced pressure. The oily residue is redissolved in ethyl acetate, washed with saturated sodium bicarbonate (twice), 10% potassium bisulfate (twice), and water (twice), dried ($Na_2SO_4$), and concentrated into a dark oily residue (28.0 g.). Flash chromatography (LPS-1 silica gel, 10% ethyl acetate/methylene chloride) affords 11.0 g. of 1-(bromoacetyl)-L-proline, 1,1-dimethylethyl ester as a pale yellow oil.

(b) 1-(N-Phenylglycyl)-L-proline, 1,1-dimethylethyl ester

To a solution of 1-(bromoacetyl)-L-proline, 1,1-dimethylethyl ester (2.1 g., 7.5 mmole) in distilled tetrahydrofuran (40 ml.) is added aniline (1.5 g., 15 mmole) and the reaction mixture is stirred overnight under nitrogen. The reaction mixture is diluted with ethyl acetate (200 ml.), washed with saturated sodium bicarbonate (2×50 ml.) and water (twice), dried ($Na_2SO_4$), and concentrated in vacuo into a dark oily residue (4.0 g.). Flash chromatography (LPS-1 silica gel, 10% ethyl acetate/methylene chloride) affords 2.2 g. of 1-(N-phenylglycyl)-L-proline, 1,1-dimethylethyl ester as a dark oil which solidifies upon drying in high vacuum.

(c) (S)-1-[N-[3-(Benzoylamino)-2-oxo-4-phenylbutyl]-N-phenylglycyl]-L-proline, 1,1-dimethylethyl ester A reaction mixture of 1-(N-phenylglycyl)-L-proline, 1,1-dimethylethyl ester (1.06 g., 3.5 mmole), (S)-N-[3-chloro-2-oxo-1-(phenylmethyl)propyl]benzamide (1.06 g., 3.5 mmole), from Example 63(b), excess sodium bicarbonate, and sodium iodide (0.52 g., 3.5 mmole) in dimethylformamide (10 ml.) is stirred at room temperature under a nitrogen atmosphere overnight. The reaction mixture is poured into water (50 ml.) and extracted with ethyl acetate (3×50 ml.). The combined ethyl acetate extracts are washed with saturated sodium bicarbonate (twice) and water (three times), dried ($Na_2SO_4$), and concentrated under reduced pressure to give a dark oily residue (2.0 g.). Flash chromatography (LPS-1 silica gel, 5% ethyl acetate/methylene chloride to 15% ethyl acetate/methylene chloride) affords 0.3 g., of (S)-1-[N-[3-(benzoylamino)-2-oxo-4-phenylbutyl]-N-phenylglycyl]-L-proline, 1,1-dimethylethyl ester as a pale yellow foam.

(d) (S)-1-[N-[3-(Benzoylamino)-2-oxo-4-phenylbutyl]-N-phenylglycyl]-L-proline, hydrochloride (20:3)

The ester product from part (c) (0.28 g., 0.49 mmole) is treated with 2N hydrochloric acid/acetic acid. After stirring for one hour at room temperature, the reaction mixture is concentrated under reduced pressure and the resulting oily residue is triturated with ether (4×) to give 0.14 g. of (S)-1-[N-[3-(benzoylamino)-2-oxo-4-phenylbutyl]-N-phenylglycyl]-L-proline, hydrochloride (20:3) as an off-white solid; m.p. 110°-140°; $R_f$ 0.76 (minor spot at 0.53) (silica gel, n-butanol/acetic acid/water; 3:1:1).

Anal. calc'd. for $C_{30}H_{31}N_3O_5.0.15HCl.0.5H_2O$: C, 68.22; H, 6.13; N, 7.95; Cl, 1.00. Found: C, 68.22; H, 6.00; N, 8.25; Cl, 0.99.

EXAMPLES 69-90

Following the procedure of Examples 63 to 68 but employing the ketone shown in Col. I, the acid chloride shown in Col. II, and the peptide ester shown in Col. III, one obtains the ester product shown in Col. IV. Removal of the $R_6$ ester group and any other protecting groups give the corresponding final product in acid form.

Col. I

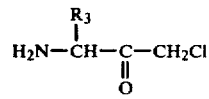

Col. II

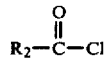

Col. III

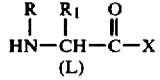

Col. IV

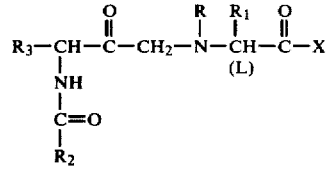

| Example | R₃ | R₂ | R₁ | X | R |
|---|---|---|---|---|---|
| 69 | -CH₂-C₆H₅ | -C₆H₅ | H- | dithiolane-CH₂-CH(COOC(CH₃)₃)(L)-NH- | cyclohexyl |
| 70 | -CH₂-C₆H₅ | -CH₂-C₆H₄-F (para) | H- | cyclohexyl-CH(CH₂-)-CH(COOC(CH₃)₃)(L)-NH- | -CH₂-C₆H₅ |
| 71 | -(CH₂)₄-C₆H₅ | -C₆H₄-CH₃ (para) | H- | C₆H₅-CH₂-CH(CH₂-)-CH(COOC(CH₃)₃)(L)-NH- | H₃C- |
| 72 | -CH₂-(thiophene) | -(CH₂)₂-C₆H₅ | H₃C- | (2-CH₂-C₆H₄)-CH(COOC(CH₃)₃)(L)-NH- (tetrahydroisoquinoline) | H₃C- |
| 73 | -CH₂-cyclopentyl | -C₆H₅ | F₃C- | (2-CH₂-C₆H₄)-CH(COOC(CH₃)₃)(L)-NH- | H- |

-continued

| Example | R₃ | R₂ | R₁ | X | R |
|---|---|---|---|---|---|
| 74 | H— | -CH₂- attached to thiophene (2-thienyl-CH₂-) | -CH₂- -N= -CH₂- with phenyl (benzyl-imidazoline type) | cyclic thiazolidine with -N- bearing -CH(COOC(CH₃)₃)(H) (L) | H— |
| 75 | H₃C—(H₂C)₃— | 2-pyridyl-CH₂- | H₃C— | —N—CH₂—COOC(CH₃)₃ attached to phenyl | H— |
| 76 | 2-pyridyl-(CH₂)₂- | phenyl-CH₂- | H₂COCHN(H₂C)₄— attached to phenyl (=O) | cyclic -N- with -CH(COOC(CH₃)₃)(H) (L) | H— |
| 77 | phenyl | phenyl-CH₂- | HN=C(NH-NO₂)-HN-(H₂C)₃- | -S-C(-S-)(-CH₂-N-)-CH(COOC(CH₃)₃)(H) (L) (spiro dithiolane) | H— |
| 78 | HN=C(NH-NO₂)-HN-(H₂C)₃- | phenyl-CH₂- | H₃C— | -S-CH(phenyl)-CH₂-N- with CH(COOC(CH₃)₃)(H) (L) | H— |
| 79 | indol-3-yl-CH₂- (H₂C- attached to indole NH) | 4-pyridyl-CH₂- | H₃C— | -O(phenyl)-CH-(H₂C)-N- with CH(COOC(CH₃)₃)(H) (L) | H— |

-continued

| Example | R₃ | R₂ | R₁ | X | R |
|---|---|---|---|---|---|
| 80 | 3-(H₂C–)-4-(H₂CO–)-phenyl with 2-OCH₂-phenyl substituent | –CH₂–C₆H₅ | H₃C–(CH₂)₂– | proline-type: N-pyrrolidine-COOC(CH₃)₃ (L) | H– |
| 81 | –C₆H₅ | –CH₂–C₆H₅ | H– | –NH–CH(CH₂OCH₂C₆H₅)–COOC(CH₃)₃ (L) | H₃C– |
| 82 | –C₆H₅ | –CH₂–(2-pyridyl) | –CH₂–C₆H₅ | –NH–CH(CH₂C₆H₅)–COOC(CH₃)₃ (L) | H– |
| 83 | 2-(H₂C–)-thiophene | –CH₂–C₆H₅ | H– | –NH–CH(CH₂–C₆H₄–OC₆H₅)–COOC(CH₃)₃ (L) | H₅C₂– |

-continued

| Example | R₃ | R₂ | R₁ | X | R |
|---|---|---|---|---|---|
| 84 | furan-2-yl-CH₂— | phenyl | H₃C— | —NH—CH(CH₂-N=CH-N(CH₂Ph))—COOC(CH₃)₃ (L) | H— |
| 85 | cyclohexyl-CH₂— | phenyl | H₃C— | —NH—CH((CH₂)₄-NHCOCH₂Ph)—COOC(CH₃)₃ (L) | H— |
| 86 | phenyl-(CH₂)₄— | phenyl | F₃C— | —NH—CH—COOC(CH₃)₃ (L) | H— |
| 87 | phenyl-CH₂— | phenyl | H₃C— | —NH—CH((CH₂)₂-C(=O)NH₂)—COOC(CH₃)₃ (L) | H— |
| 88 | phenyl-CH₂— | phenyl | H₃C— | dithiolane-Pro-O-CH(cyclohexyl)-O-C(=O)-OC₂H₅ (L) | H— |
| 89 | pyridin-2-yl-(CH₂)₄— | phenyl | H₃C— | Pro-O-CH(CH(CH₃)₂)-O-C(=O)-OC₂H₅ (L), Pro-O-CH₂-O-C(=O)-OC(CH₃)₃ (L) | H— |

-continued
| Example | R₃ | R₂ | R₁ | X | R |
|---|---|---|---|---|---|
| 90 | 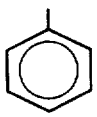 |  | H₃C— | 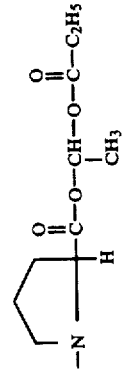 | H— |

The R₁ protecting groups in Examples 74, 76 and 77, the R₃ protecting groups in Examples 78 and 80, and the R₅ protecting groups in Examples 81 and 83 to 85 are removed as the last step in the synthesis. The R₆ ester groups shown in Examples 87 to 90 are not removed.

EXAMPLE 91

(±)-1-[N-[3-(Benzoylamino)-2-oxo-4-phenylbutyl]-N-methylglycyl]-L-proline, monohydrochloride (a) [3-(Benzoylamino)-2-oxo-4-phenylbutyl]methylcarbamic acid, phenylmethyl ester N-methyl-N-[(phenylmethoxy)carbonyl]glycine (2.23 g., 10 mmole) is dissolved in 30 ml. of tetrahydrofuran and cooled in an ice-bath. Oxalyl chloride (1 ml., 11.5 mmole) is added followed by 2 drops of dimethylformamide. After stirring for 30 minutes in the ice-bath, the mixture is then stirred at room temperature for an hour. To this 0.25 ml. of oxalyl chloride is added. The mixture is evaporated, redissolved in 15 ml. of tetrahydrofuran, and stirred in an ice bath. A solution of 2-phenyl-4-(phenylmethyl)-5(4H)-oxazolone (3.1 g., 12.4 mmole) dissolved in 15 ml. of tetrahydrofuran is added to the above solution stirring in the ice-bath. Triethylamine (1.4 ml., 10 mmole) is added and the solution is stirred at room temperature overnight. The precipitated triethylamine hydrochloride salt is filtered off. Tetrahydrofuran is removed from the residue and it is then redissolved in pyridine (5 ml.) and p-dimethylamino pyridine (20 mg.) is added. After stirring at room temperature for 3 hours, acetic acid (5 ml.) is added and the reaction mixture is kept at 105° for 30 minutes. The reaction mixture is then evaporated, the residue is dissolved in ethyl acetate, and washed with aqueous sodium bicarbonate and water. After trituration with ethyl acetate/hexane, 2.2 g. of homogeneous [3-(benzoylamino)-2-oxo-4-phenylbutyl]methylcarbamic acid, phenylmethyl ester is obtained; m.p. 140°-141°.

(b) (±)-N-[3-(Methylamino)-2-oxo-1-(phenylmethyl)-propyl]benzamide, hydrochloride

[3-(Benzoylamino)-2-oxo-4-phenylbutyl]methylcarbamic acid, phenylmethyl ester (0.5 g.) is dissolved in ethanol (50 ml.) containing 1N hydrochloric acid (2 ml.). Palladium carbon catalyst (10%, 100 mg.) is added and hydrogenation is continued overnight. The reaction mixture is then filtered, evaporated, dissolved in water, and lyophilized to 300 mg. of (±)-N-[3-(methylamino)-2-oxo-1-(phenylmethyl)propyl]benzamide, hydrochloride as a homogeneous white powder.

(c) (±)-1-[N-[3-(Benzoylamino)-2-oxo-4-phenylbutyl]-N-methylglycyl]-L-proline, 1,1-dimethylethyl ester A reaction mixture of (±)-N-[3-(methylamino)-2-oxo-1-(phenylmethyl)propyl]benzamide, hydrochloride (1.65 g., 5 mmole), 1-(bromoacetyl)-L-proline, 1,1-dimethylethyl ester (2.9 g., 10 mmole), from Example 68(a), and diisopropylethylamine (1.74 ml., 10 mmole) in dimethylformamide (20 ml.), is stirred at room temperature under nitrogen overnight. The reaction mixture is partitioned between water/ethyl acetate and the aqueous layer is extracted once more with ethyl acetate. The ethyl acetate extracts are dried (Na₂SO₄) and concentrated to a yellow oily residue (4.0 g.). Flash chromatography (150 g. of Merck silica gel 60) affords 0.7 g. of (±)-1-[N-[3-(benzoylamino)-2-oxo-4-phenylbutyl]-N-methylglycyl]-L-proline, 1,1-dimethylethyl ester as a yellow foam.

(d) (±)-1-[N-[3-(Benzoylamino)-2-oxo-4-phenylbutyl]-N-methylglycyl]-L-proline, monohydrochloride The ester product from part (c) (0.04 g., 0.79 mmole) is treated with 2N hydrochloric acid/acetic acid (5 ml.). After stirring for 45 minutes at room temperature, the reaction mixture is concentrated under reduced pressure and the resulting oily residue is triturated with ether (3×) to give 0.28 g. of (±)-1-[N-[3-(benzoylamino)-2-oxo-4-phenylbutyl]-N-methylglycyl]-L-proline, monohydrochloride as a white solid; m.p. 125°-130°. R_f 0.73 (silica gel, n-butanol/acetic acid/water; 3:1:1).

Anal. calc'd. for C₂₅H₂₉N₃O₅.HCl.0.23H₂O: C, 61.01; H, 6.24; N, 8.54. Found: C, 61.01; H, 6.10; N, 8.36.

EXAMPLE 92

(S)-7-[[[3-(Benzoylamino)-2-oxo-4-phenylbutyl]methylamino]acetyl]-1,4-dithia-7-azaspiro[4.4]nonane-8-carboxylic acid, trifluoroacetate salt (1:1)

(a) (S)-7-(Bromoacetyl)-1,4-dithia-7-azaspiro-[4.4]nonane-8-carboxylic acid (S)-1,4-Dithia-7-azaspiro[4.4]nonane-8-carboxylic acid, hydrochloride (2.1 g., 8.7 mmole) is dissolved in 1N sodium hydroxide (25 ml.), chilled to 0° and bromoacetyl bromide (2.1 g., 0.91 ml., 10.4 mmole) is added dropwise over a 10 minute period. The reaction mixture is stirred for 2 hours (0° to room temperature), washed with ethyl acetate (twice), and the aqueous layer is acidified to pH 2 and extracted with ethyl acetate (3×). The combined organic extracts are dried (Na₂SO₄) and concentrated to give 2.25 g. of (S)-7-(bromoacetyl)-1,4-dithia-7-azaspiro[4.4]nonane-8-carboxylic acid.

(b) (S)-7-(Bromoacetyl)-1,4-dithia-7-azaspiro[4.4]nonane-8-carboxylic acid, diphenylmethyl ester (S)-7-(Bromoacetyl)-1,4-dithia-7-azaspiro[4.4]nonane-8-carboxylic acid (2.25 g., 6.9 mmole) is dissolved in ethyl acetate (150 ml.). Diphenyldiazomethane (1.3 g., 6.9 mmole) is added and the reaction mixture is stirred overnight at room temperatuure. The decolorized reaction mixture is washed with saturated sodium bicarbonate (twice), 10% potassium bisulfite (twice) and water, dried (Na₂SO₄), and concentrated to give 2.5 g. of (S)-7-(bromoacetyl)-1,4-dithia-7-azaspiro[4.4]nonane-8-carboxylic acid, diphenylmethyl ester as a white solid residue.

(c) (S)-7-[[[3-(Benzoylamino)-2-oxo-4-phenybutyl]-methylamino]acetyl]-1,4-dithia-7-azaspiro[4.4]nonane-8-carboxylic acid, diphenylmethyl ester A mixture of the ester product from part (b) (2.4 g., 4.87 mmole), (±)-N-[3-(methylamino)-2-oxo-1-(phenylmethyl)propyl]benzamide (0.81 g., 2.43 mmole), prepared as set forth in Example 91(b), and diisopropylethylamine (0.85 ml., 4.87 mmole) in dimethylformamide (20 ml.) is stirred at room temperature overnight. The reaction mixture is poured into water (50 ml.), and extracted with ethyl acetate (3×100 ml.). The combined organic extracts are washed with saturated sodium bicarbonate, 10% potassium bisulfite, and water, dried (Na₂SO₄), and concentrated into a dark oily residue (2.8 g.). Flash chromatography (200 g. Merck silica gel, 10% ethyl acetate/methylene chloride, 20% methanol/ethyl acetate) affords 1.1 g. of (S)-7-[[[3-(benzoylamino-2-oxo-4-phenylbutyl]methylamino]acetyl]-1,4-dithia-7-azaspiro[4.4]nonane-8-carboxylic acid, diphenylmethyl ester as a yellow oil.

(d) (S)-7-[[[3-(Benzoylamino)-2-oxo-4-phenylbutyl]methylamino]acetyl]-1,4-dithia-7-azaspiro[4.4]nonane-8carboxylic acid, trifluoroacetate salt (1:1)

The ester product from part (c) (10.5 g., 0.72 mmole) is added to chilled (0°) trifluoroacetic acid (2 ml.) containing anisole (0.1 ml.). After stirring for one hour, the volatiles are removed in vacuo and the residue is chased with toluene (twice). The oily residue is triturated with ether (4×) affording 0.36 g. of (S)-7-[[[3-(benzoylamino)-2-oxo-4-phenylbutyl]methylamino]acetyl]-1,4-dithia-7-azaspiro[4.4]nonane-8-carboxylic acid, trifluoroacetate salt (1:1); m.p. 120°–125°. $R_f$ 0.45 (trailing) (silica gel, n-butanol/acetic acid/water; 4:1:1).

Anal. calc'd. for $C_{27}H_{31}N_3O_5S_2 \cdot C_2HF_3O_2$: C, 53.11; H, 4.92; N, 6.40; S, 9.78. Found: C, 52.68; H, 5.03; N, 6.53; S, 9.97.

EXAMPLE 93

(S)-2-[[[3-(Benzoylamino)-2-oxo-4-phenylbutyl]methylamino]acetyl]-1,2,3,4-tetrahydro-3-isoquinolinecarboxylic acid, monohydrochloride (a) 2-(Bromoacetyl)-1,2,3,4-tetrahydro-3-isoquinolinecarboxylic acid, 1,1-dimethylethyl ester To a chilled solution of 1,2,3,4-tetrahydro-3-isoquinolinecarboxylic acid, 1,1-dimethylethyl ester (7.7 g., 33 mmole) in methylene chloride (100 ml.) is added diisopropylethylamine (6.23 ml., 36.3 mmole) and finally over a 15 minute period bromoacetyl bromide (6.6 g., 2.87 ml., 33 mmole) while keeping the temperature at 5°. The reaction mixture is stirred overnight (−5° to room temperature), Concentrated to about 33⅓% of its volume, diluted with ethyl acetate (100 ml.), washed with saturated sodium bicarbonate (twice), 10% potassium bisulfate (twice), and water (twice), dried ($Na_2SO_4$), and concentrated into a dark yellow semi-solid residue (11.0 g.). Recrystallization from ethyl acetate/hexane affords 4.2 g. of 2-(bromoacetyl)-1,2,3,4-tetrahydro-3-isoquinolinecarboxylic acid, 1,1-dimethylethyl ester as a cream colored solid; m.p. 92°–95° (85°).

(b) (S)-2-[[[3-(Benzoylamino)-2-oxo-4-phenylbutyl]methylamino]acetyl]-1,2,3,4-tetrahydro-3-isoquinolinecarboxylic acid, 1,1-dimethylethyl ester To a solution of 2-(bromoacetyl)-1,2,3,4-tetrahydro-3-isoquinolinecarboxylic acid, 1,1-dimethylethyl ester (2.12 g., 6 mmole) in dimethylformamide (20 ml.) is added (±)-N-[3-(methylamino)-2-oxo-1-(phenylmethyl)propyl]benzamide (2.0 g., 6 mmole), prepared as set forth in Example 91(b), and diisopropylethylamine (0.77 g., 1.04 ml., 6 mmole). The reaction mixture is stirred overnight, poured into water (50 ml.) and extracted with ethyl acetate (3×50 ml.). The combined ethyl acetate extracts are washed with saturated sodium bicarbonate (twice) and water (twice), dried ($Na_2SO_4$), and concentrated into a yellow oily residue (2.9 g.). Flash chromatography (200 g. Merck silica, 2% methanol/chloroform) gives 0.68 g. (S)-2-[[[3-(benzoylamino)-2-oxo-4-phenylbutyl]methylamino]acetyl]-1,2,3,4-tetrahydro-3-isoquinolinecarboxylic acid, 1,1-dimethylethyl ester as a yellow dried up foam.

(c) (S)-2-[[[3-(Benzoylamino)-2-oxo-4-phenylbutyl]methylamino]acetyl]-1,2,3,4-tetrahydro-3-isoquinolinecarboxylic acid, monohydrochloride The ester product from part (b) (1.67 g., 1.17 mmole) is treated with 2N hydrochloric acid/acetic acid (5 ml.). After stirring for one hour at room temperature, the reaction mixture is concentrated under reduced pressure and the resulting oily residue is triturated with ether (4×) to give 0.55 g. of (S)-2-[[[3-(benzoylamino)-2-oxo-4-phenylbutyl]methylamino]acetyl]-1,2,3,4-tetrahydro-3-isoquinolinecarboxylic acid, monohydrochloride as an off white solid; m.p. 123°–126°. $R_f$ 0.47 (silica gel, n-butanol/acetic acid/water; 4:1:1).

Anal. Calc'd. for $C_{30}H_{31}N_3O_5 \cdot HCl \cdot 0.32H_2O$: C, 64.82; H, 5.92; N, 7.56; Cl, 6.38. Found: C, 64.82; H, 6.22; N, 7.55; Cl, 6.13.

EXAMPLE 94

[1(±),4S]-1-[N-[3-(Benzoylamino)-2-oxo-4-phenylbutyl]-N-methylglycyl]-4-(phenylthio)-L-proline, monohydrochloride (a) (4S)-1-(Bromoacetyl)-4-(phenylthio)-L-proline To a suspension of (4S)-4-(phenylthio)-L-proline (2.2 g., 10 mmole) in methylene chloride (50 ml., freshly distilled) is added bis(trimethylsilyl) acetamide (7.35 ml., 30 mmole). The reaction mixture is stirred at room temperature for 2 hours until it becomes almost clear. The reaction mixture is then cooled to −5° and bromoacetyl chloride (1.9 g., 1.0 ml., 12 mmole) is added dropwise keeping the temperature at −5°. After stirring overnight (−5° to room temperature), the reaction mixture is concentrated to about 50% of its volume, partitioned between saturated sodium bicarbonate/ethyl acetate and the layers are separated. The organic layer is extracted once more with saturated sodium bicarbonate. The combined aqueous layers are acidified to pH 2.0 with 10% potassium bisulfate and extracted with ethyl acetate (3×). The ethyl acetate fractions are combined, dried ($Na_2SO_4$) and concentrated to give 3.5 g. of (4S)-1-(bromoacetyl)-4-(phenylthio)-L-proline as a viscous oil.

(b) (4S)-1-(Bromoacetyl)-4-(phenylthio)-L-proline, diphenylmethyl ester

A solution of diphenyldiazomethane (2.0 g., 10.2 mmole) in ethyl acetate (50 ml.) is added dropwise to a solution of (4S)-1-(bromoacetyl)-4-(phenylthio)-L-proline (3.5 g., 10.2 mmole) in ethyl acetate (50 ml.). The purple solution is stirred at room temperature overnight. The decolorized reaction mixture is washed with saturated sodium carbonate (twice) and water (twice), dried ($Na_2SO_4$), and concentrated to give 4.78 g. of (4S)-1-(bromoacetyl)-4-(phenylthio)-L-proline, diphenylmethyl ester as a yellow viscous oil.

(c) [1(±),4S]-1-[N-[3-(Benzoylamino)-2-oxo-4-phenylbutyl]-N-methylglycyl]-4-(phenylthio)-L-proline, diphenylmethyl ester To a solution of (4S)-1-(bromoacetyl)-4-(phenylthio)-L-proline, diphenylmethyl ester (4.78 g., 9.4 mmole) in dimethylformamide (20 ml.) is added (±)-N-[3-(methylamino)-2-oxo-1-phenylmethyl)propyl]benzamide (2.42 g., 7.2 mmole), prepared as set forth in Example 91(b), and diisopropylethylamine (0.93 g., 1.25 ml., 7.2 mmole). After stirring overnight at room temperature, the reaction mixture is poured into water (50 ml.) and extracted with ethyl acetate (3×). The combined ethyl acetate extracts are washed with saturated sodium bicarbonate (twice) and water (twice), dried ($Na_2SO_4$), and concentrated into a yellow oil (6.2 g.). Flash chromatography (Merck silica gel, 2% methanol/methylene chloride) gives 3.2 g. of [1(±),4S]-1-[N-[3-(benzoylamino)-2-oxo-4-phenylbutyl]-N-methylglycyl]-4-(phenylthio)-L-proline, diphenylmethyl ester as a pale yellow foam.

(d) [1(±),4S]-1-[N-[3-(Benzoylamino)-2-oxo-4-phenylbutyl]-N-methylglycyl]-4-(phenylthio)-L-proline, monohydrochloride The ester product from part (c) (1.6 g., 2.2 mmole) is treated with 2N hydrochloric acid/acetic acid (20 ml.).

After stirring for 2 hours at room temperature, the reaction mixture is concentrated under reduced pressure and the oily residue is triturated with ether overnight to yield 1.2 g. of [1(±),4S]-1-[N-[3-(benzoylamino)-2-oxo-4-phenylbutyl]-N-methylglycyl]-4-(phenylthio)-L-proline, monohydrochloride as an off-white solid; m.p. 131°–133° R$_f$0.38 (silica gel, n-butanol/acetic acid/water; 4:1:1).

Anal. cald'd. for C$_{31}$H$_{33}$N$_3$O$_5$S.HCl.0.9H$_2$O: C, 60.82; H, 5.90; N, 6.87; S, 5.24; Cl, 5.79. Found: C, 60.82; H, 5.74; N, 6.94; S, 5.25; Cl, 5.75.

EXAMPLE 95

(4S)-1-[N-[3-(Benzoylamino)-2-oxo-4-phenylbutyl]-N-methylglycyl]-4-(4-fluorophenoxy)-L-proline, monohydrochloride (a) (4S)-1-(Bromoacetyl)-4-(fluorophenoxy)-L-proline, 1,1-dimethylethyl ester To a solution of (S)-4-(fluorophenoxy)-L-proline, 1,1-dimethylethyl ester (2.1 g., 7.5 mmole) in distilled tetrahydrofuran (50 ml.) is added bromoacetic acid (1.04 g., 7.5 mmole), hydroxybenzotriazole hydrate (1.14 g., 7.5 mmole) and dicyclohexylcarbodiimide (1.54 g., 7.5 mmole). The reaction mixture is stirred overnight, the precipitated dicyclohexylurea is filtered off, and the filtrate is concentrated. The residue is dissolved in ethyl acetate (50 ml.) and washed with saturated sodium bicarbonate (twice), 10% potassium bisulfate (twice) and water (twice), dried (Na$_2$SO$_4$) and concentrated to give 3.1 g. of (4S)-1-(bromoacetyl)-4-(fluorophenoxy)-L-proline, 1,1-dimethylethyl ester as an oily residue.

(b) (4S)-1-[N-[3-(Benzoylamino)-2-oxo-4-phenylbutyl]-N-methylglycyl]-4-(4-fluorophenoxy)-L-proline, 1,1-dimethylethyl ester To a solution of (4S)-1-(bromoacetyl)-4-(fluorophenoxy)-L-proline, 1,1-dimethylethyl ester (3.4 g., 8.5 mmole) in dimethylformamide (20 ml.) is added (±)-N-[3-(methylamino)-2-oxo-1-(phenylmethyl)-propyl]benzamide (2.83 g., 8.5 mmole), prepared as set forth in Example 91(b), and diisopropylethylamine (1.43 g., 1.92 ml., 11.0 mmole). After stirring overnight at room temperature, the reaction mixture is poured into water (100 ml.) and extracted with ethyl acetate (3×). The combined ethyl acetate extracts are washed with saturated sodium bicarbonate (twice), 10% potassium bisulfate (twice), and water (twice), dried (Na$_2$SO$_4$), and concentrated into a dark residue (5.5 g.). Flash chromatography (LPS-1 silica gel, 50% ethyl acetate/methylene chloride) gives 1.2 g. of (4S)-1-[N-[3-(benzoylamino)-2-oxo-4-phenylbutyl]-N-methylglycyl] 4-(4-fluorophenoxy)-L-proline, 1,1-dimethylethyl ester as a pale yellow foam.

(c) (4S)-1-[N-[3-(Benzoylamino)-2-oxo-4-phenylbutyl]-N-methylglycyl]-4-(4-fluorophenoxy)-L-proline, monohydrochloride The ester product from part (b) (1.2 g., 1.95 mmole) is treated with 2N hydrochloric acid/acetic acid (20 ml.). After stirring for 2 hours at room temperature, the reaction mixture is concentrated under reduced pressure and the oily residue is triturated with ether overnight to yield 0.92 g. of (4S)-1-[N-[3-(benzoylamino)-2-oxo-4-phenylbutyl]-N-methylglycyl]-4-(4-fluorophenoxy)-L-proline, monohydrochloride as an off-white solid; m.p. 131°–140°. R$_f$0.54 (silica gel, n-butanol/acetic acid/water; 3:1:1).

Anal. calc'd. for C$_{31}$H$_{32}$N$_3$FO$_6$.HCl.0.55H$_2$O: C, 61.24; H, 5.65; N, 6.91; Cl, 5.83. Found: C, 61.24; H, 5.66; N, 7.09; Cl, 5.70.

In a similar manner, the procedure of Examples 91 to 95 can be employed to prepare the compounds of Examples 1 to 90.

EXAMPLE 96

N-[N-[3-(Benzoylamino)-2-oxo-4-phenylbutyl]-N-methylglycyl]-N-cyclohexylglycine, monohydrochloride (a) (±)-N-[3-(Benzoylamino)-2-oxo-4-phenylbutyl]-N-methylglycine,1,1-dimethylethyl ester To a solution of (±)-N-[3-(methylamino)-2-oxo-1-(phenylmethyl)propyl]benzamide (5.0 g., 15 mmole), prepared as set forth in Example 91(b), in dimethylformamide (20 ml.) is added bromoacetic acid, 1,1-dimethylethyl ester (13.8 g., 3.15 ml., 19.5 mmole) and diisopropylethylamine (2.5 g., 3.4 ml., 19.5 mmole). After stirring overnight at room temperature, the reaction mixture is poured into water (100 ml.) and extracted with ethyl acetate (3×). The combined ethyl acetate extracts are washed with saturated sodium bicarbonate (twice), 10% potassium bisulfate (twice), and water (twice), dried (Na$_2$SO$_4$), and concentrated into a yellow oil, which becomes a dried up foam upon drying in high vacuum, to give 5.4 g. of (±)-N-[3-(benzoylamino)-2-oxo-4-phenylbutyl]-N-methylglycine, 1,1-dimethylethyl ester.

(b) (±)-N-[3-(Benzoylamino)-2-oxo-4-phenylbutyl]-N-methylglycine, monohydrochloride The ester product from part (a) (4.51 g., 11 mmole) is treated with 2N hydrochloric acid/acetic acid (20 ml.). After stirring for 2.5 hours at room temperature, the reaction mixture is concentrated under reduced pressure and the oily residue is triturated with ether to give 3.3 g. of (±)-N-[3-(benzoylamino)-2-oxo-4-phenylbutyl]-N-methylglycine, monohydrochloride as an off-white solid.

(c) N-[N-[3-(Benzoylamino)-2-oxo-4-phenylbutyl]-N-methylglycyl]-N-cyclohexylglycine, 1,1-dimethylethyl ester To a solution of (±)-N-[3-(benzoylamino)-2-oxo-4-phenylbutyl]-N-methylglycine, hydrochloride (1.0 g., 2.6 mmole) in distilled tetrahydrofuran (50 ml.) is added N-cyclohexylglycine, 1,1-dimethylethyl ester (0.55 g., 2.6 mmole), prepared as set forth in Example 65(a), hydroxybenzotriazole hydrate (0.39 g., 2.6 mmole), and dicyclohexylcarbodiimide (0.55 g., 2.6 mmole). The reaction mixture is stirred overnight, the precipitated dicyclohexylurea is filtered off, and the filtrate is concentrated. The residue is dissolved in ethyl acetate (50 ml.) and washed with saturated sodium bicarbonate (twice), 10% potassium bisulfate (twice), and water (twice), dried (Na$_2$SO$_4$) and concentrated into an oily residue (1.5 g.). Flash chromatography (100 g., Merck silica gel 60) gives 0.49 g. of N-[N-[3-(benzoylamino)-2-oxo-4-phenylbutyl]-N-methylglycyl]-N-cyclohexylglycine, 1,1-dimethylethyl ester as a foam.

(d) N-[N-[3-(Benzoylamino)-2-oxo-4-phenylbutyl]-N-methylglycyl]-N-cyclohexylglycine, monohydrochloride The ester product from part (c) (0.48 g., 0.87 mmole) is treated with 2N hydrochloric acid/acetic acid (10 ml.). After stirring for 2 hours at room temperature, the reaction mixture is concentrated under reduced pressure and the oily residue is triturated with ether overnight to give 0.32 g. of N-[N-[3-(benzoylamino)-2-oxo-4-phenylbutyl]-N-methyglycyl]-N-cyclohexylglycine, monohydrochloride as an off-white solid; m.p. 131°–145°. $R_f$ 0.36 (silica gel, n-butanol/acetic acid/water; 4:1:1).

Anal. calc'd. for $C_{28}H_{35}N_3O_5 \cdot HCl \cdot 0.7H_2O$: C, 61.95; H, 6.95; N, 7.74; Cl, 6.53. Found: C, 61.95; H, 6.74; N, 7.71; Cl, 6.23.

EXAMPLE 97

(S)-7-[[[(±)-3-(Benzoylamino)-2-oxo-4-phenylbutyl]-methylamino]acetyl]-1,4-dithia-7-azaspiro[4.4]nonane-8-carboxylic acid, methyl ester To a solution of (±)-N-[3-(benzoylamino)-2-oxo-4-phenylbutyl]-N-methylglycine, monohydrochloride (1.0 g., 2.5 mmole), prepared as set forth in Example 96(b), in distilled tetrahydrofuran (50 ml.) is added (S)-1,4-dithia-7-azaspiro[4.4]nonane-8-carboxylic acid, methyl ester, monohydrochloride (0.66 g., 2.5 mmole), dicyclohexylcarbodiimide (0.54 g., 2.5 mmole), hydroxybenzotriazole hydrate (0.39 g., 2.5 mmole) and diisopropylethylamine (0.9 ml., 5 mmole). The reaction mixture is stirred overnight, the precipitated dicyclohexylurea is filtered off, and the filtrate is concentrated. The residue is dissolved in ethyl acetate (100 ml.) and washed with saturated sodium bicarbonate (twice) and water (twice), dried ($Na_2SO_4$), and concentrated into a yellow oily residue (1.3 g.). Flash chromatography (Merck silica gel, 25% ethyl acetate/methylene chloride, 1% methanol/methylene chloride) affords 0.53 g. of (S)-7-[[[(±)-3-(benzoylamino)-2-oxo-4-phenylbutyl]-methylamino]acetyl]-1,4-dithia-7-azaspiro[4.4]nonane-8-carboxylic acid, methyl ester as a white foam; m.p. 60°–62°. $R_f$ 0.52 (silica gel, 5% methanol/methylene chloride).

Anal. calc'd. for $C_{28}H_{33}N_3O_5S_2 \cdot 0.33H_2O$: C, 59.87; H, 6.04; N, 7.48; S, 11.42. Found: C, 59.87; H, 5.94; N, 7.56; S, 11.36.

EXAMPLE 98

(S)-7-[[[(±)-3-(Benzoylamino)-2-oxo-4-phenylbutyl]-methylamino]acetyl]-1,4-dithia-7-azaspiro[4.4]nonane-8-carboxylic acid, methyl ester, monohydrochloride The methyl ester product from Example 97 (0.26 g., 0.46 mmole) is treated with 2N hydrochloric acid/acetic acid until homogeneous (2 minutes), concentrated under reduced pressure, and the oily residue is triturated with ether (twice) to give 0.26 g. of (S)-7-[[[(±)-3-(benzoylamino)-2-oxo-4-phenylbutyl]methylamino]acetyl]-1,4-dithia-7-azaspiro[4.4]nonane-8-carboxylic acid, methyl ester, monohydrochloride as a white solid; m.p. 79°–85°. $R_f$ 0.53 (silica gel, 5% methanol/methylene chloride).

Anal. calc'd. for $C_{28}H_{33}N_3O_5S_2 \cdot HCl \cdot 0.56H_2O$: C, 55.84; H, 5.88; N, 6.98; S, 10.64; Cl, 5.88. Found: C, 55.84; H, 5.95; N, 6.78; S, 10.43; Cl, 5.66.

EXAMPLE 99

(4S)-1-[N-[3-(Benzoylamino)-2-oxo-4-phenylbutyl]-N-methylglycyl]-4-(4-fluorophenoxy)-L-proline, methyl ester, monohydrochloride (a) (4S)-4-(Fluorophenoxy)-L-proline, methyl ester, monohydrochloride To a suspension of (4S)-4-(fluorophenoxy)-L-proline (2.5 g., 11 mmole) in methanol at −30° under an argon atmosphere is added thionyl chloride (8.09 ml., 11 mmole). The reaction mixture is stirred at −20° for 2 hours, then at room temperature for 16 hours. Solvent is removed at reduced pressure and the residue is redissolved in methylene chloride (150 ml.) and washed with 1N sodium carbonate (twice) and water (twice). After drying (MgSO4), excess hydrochloric acid/methanol is added and solvent is removed at reduced pressure. Addition of ether gives a light brown solid (2.6 g.). Recrystallization from methanol/ether gives 1.49 g. of (4S)-4-(fluorophenoxy)-L-proline, methyl ester, monohydrochloride as a light brown solid; m.p. 147°–148°; $[\alpha]_D^{20} = +6.96°$ (c = 1.55, methanol).

(b) (4S)-1-[N-[3-(Benzoylamino)-2-oxo-4-phenylbutyl]-N-methylglycyl]-4-(4-fluorophenoxy)-L-proline, methyl ester To a solution of (±)-N-[3-(benzoylamino)-2-oxo-4-phenylbutyl]-N-methylglycine, monohydrochloride (1.17 g., 3 mmole), prepared as set forth in Example 96(b), in distilled tetrahydrofuran (20 ml.) is added (4S)-4-(fluorophenoxy)-L-proline, methyl ester, monohydrochloride (0.82 g., 3 mmole), hydroxybenzotriazole hydrate (0.46 g., 3 mmole) and dicyclohexylcarbodiimide (0.62 g., 3 mmole). The reaction mixture is stirred overnight, the precipitated dicyclohexylurea is filtered off, and the filtrate is concentrated. The residue is dissolved in ethyl acetate (50 ml.) and washed with saturated sodium bicarbonate (twice) and water (twice), dried ($Na_2SO_4$), and concentrated into an oily residue (1.1 g.). Flash chromatography (200 g., Merck silica gel 60; 3% methanol/chloroform) gives 0.15 g. of (4S)-1-[N-[3-(benzoylamino)-2-oxo-4-phenylbutyl]-N-methylglycyl]-4-(4-fluorophenoxy)-L-proline, methyl ester as a foam.

(c) (4S)-1-[N-[3-(Benzoylamino)-2-oxo-4-phenylbutyl]-N-methylglycyl]-4-(4-fluorophenoxy)-2-proline, methyl ester, monohydrochloride The methyl ester product from part (b) (0.15 g., 0.26 mmole) is treated with 2N hydrochloric acid/acetic acid until homogeneous (2 minutes), concentrated under reduced pressure, and the oily residue is triturated with ether (twice) to afford 0.14 g. of (4S)-1-[N-[3-(benzoylamino)-2-oxo-4-phenylbutyl]-N-methylglycyl]-4-(4-fluorophenoxy)-L-proline, methyl ester, monohydrochloride as an off-white solid; m.p. 105°–125°. $R_f$ 0.27 (silica gel, 5% methanol/chloroform).

Anal. calc'd. for $C_{32}H_{34}FO_6 \cdot HCl$ C, 62.79; H, 5.76; N, 6.86; F, 3.10; Cl, 5.79. Found: C, 62.78; H, 5.73; N, 6.87; F, 2.83; Cl, 5.33.

EXAMPLE 100

(4S)-1-[N-[(S)-3-(Benzoylamino)-2-oxo-4-phenylbutyl]-L-alanyl]-4-(4-fluorophenoxy)-L-proline, monohydrochloride (a) (S)-N-[3-(Benzoylamino)-2-oxo-4-phenylbutyl]-L-alanine, 1,1-dimethylethyl ester To a stirring solution of (S)-N-[3-chloro-2-oxo-1-(phenylmethyl)propyl]benzamide (10.0 g., 33.1 mmole) in dimethylformamide (80ml.) is added L-alanine, 1,1-dimethylethyl ester, hydrochloride (6.0 g., 33.1 mmole), sodium bicarbonate (6.1 g., 72 mmole) and sodium iodide (4.9 g., 33.1 mmole). The resulting solution is stirred overnight at room temperature, poured into ether and washed with water (twice) and 10% sodium bicarbonate. The ether solution is extracted with 1N hydrochloric acid (3×), the combined extracts are made basic by the addition of solid sodium bicarbonate and extracted with ethyl acetate (4×). The organic extracts are combined, dried (MgSO4) and concentrated to give 8.9 g. of pale yellow solid. A portion of this material is recrystallized from ethyl acetate to give (S)-N-[3-(benzoylamino)-2-oxo-4-phenylbutyl]-L-alanine, 1,1-dimethylethyl ester as a white solid; m.p. 106.5°–110°.

(b) (S)-N-[3-(Benzoylamino)-2-oxo-4-phenylbutyl]-L-alanine, monohydrochloride

A solution of the ester product from part (a) (2.95 g., 5.4 mmole) in 1.4N hydrochloric acid in acetic acid (39 ml.) is stirred at room temperature for 2 hours. The resulting white precipitate is collected, rinsed with ether and dried to give 2.27 g. of (S)-N-[3-(benzoylamino)-2-oxo-4-phenylbutyl]-L-alanine, monohydrochloride; m.p. 208°–209° (dec.); $[\alpha]_D = -71°$ (c=0.38% in methanol). $R_f$ 0.51 (silica gel; chloroform/methanol/acetic acid; 4:1:1).

Anal. calc'd. for $C_{20}H_{22}N_2O_4 \cdot HCl$: C, 61.64; H, 5.93; N, 7.17; Cl, 9.07. Found: C, 61.33; H, 5.97; N, 7.17; Cl, 8.79.

(c) (S)-N-[N-(Benzoylamino)-2-oxo-4-phenylbutyl]-N-[(phenylmethoxy)carbonyl]-L-alanine Triethylamine (2.1 ml., 15 mmole) is added to a mixture of (S)-N-[3-(benzoylamino)-2-oxo-4-phenylbutyl]-L-alanine, monohydrochloride (2.0 g., 5.1 mmole), benzyl chloroformate (730 μl., 5.1 mmole), water (7 ml.) and dioxane (7 ml.) at 25°. The resulting mixture is stirred at 25° for 3 hours, after which it is poured into 5% aqueous sodium bicarbonate solution and washed with ether. The aqueous layer is acidified (HCl) and extracted into ethyl acetate (3×). The extract is dried (MgSO4) and concentrated to give a colorless oil. Trituration with ether produces a white granular solid (150 mg.) which is collected and discarded. The mother liquor is concentrated in vacuo to give 1.75 g. of (S)-N-[N-(benzoylamino)-2-oxo-4-phenylbutyl]-N-[(phenylmethoxy)carbonyl]-L-alanine as a white glass.

(d) (4S)-1-[N-[(S)-3-(Benzoylamino)-2-oxo-4-phenylbutyl]-N-[(phenylmethoxy)carbonyl]-L-alanyl]-4-(4-fluorophenoxy)-L-proline, phenylmethyl ester A mixture of (S)-N-[N-(benzoylamino)-2-oxo-4-phenylbutyl]-N-[(phenylmethoxy)carbonyl]-L-alanine (300 mg., 0.62 mmole), (4S)-4-(4-fluorophenoxy)-L-proline, phenylmethyl ester, p-toluenesulfonic acid salt (300 mg., 0.62 mmole), triethylamine (90 μl., 0.62 mmole), dicyclohexylcarbodiimide (130 mg., 0.62 mmole), and hydroxybenzotriazole hydrate (90 mg., 0.62 mmole) in tetrahydrofuran (7 ml. ) is stirred at 25° for 20 hours. The mixture is then filtered and diluted with ethyl acetate. The resulting solution is washed sequentially with 1N hydrochloric acid and 10% aqueous sodium bicarbonate solution, dried (MgSO4), filtered, and concentrated to give 500 mg. of (4S)-1-[N-[(S)-3-(benzoylamino)-2-oxo-4-phenylbutyl]-N-[(phenylmethoxy)carbonyl]-L-alanyl]-4-(4-fluorophenoxy)-L-proline, phenylmethyl ester as a pale yellow oil.

(e) (4S)-1-[N-[(S)-3-(Benzoylamino)-2-oxo-4-phenylbutyl]-L-alanyl]-4-(4-fluorophenoxy)-L-proline, monohydrochloride A mixture of the ester product from part (d) (500 mg., 0.6 mmole), palladium on carbon catalyst (10%, 100 mg.), absolute ethanol (15 ml.), and 1.0N aqueous hydrochloric acid (800 μl., 0.8 mmole) is hydrogenated at 1 atmosphere and 25° for 17 hours, after which it is filtered and concentrated. The residue is chromatographed on HP-20 a linear gradient from [9:1, 0.01N aqueous hydrochloric acid:methanol] to [1:1, 0.01N aqueous hydrochloric acid:methanol]. Fractions containing the desired product (TLC) are combined and concentrated. The residue is dissolved in a minimum amount of methanol. Ether is added, resulting in a white precipitate which is collected and dried in vacuo to give 200 mg. of (4S)-1-[N-[(S)-3-(benzoylamino)-2-oxo-4-phenylbutyl]-L-alanyl]-4-(4-fluorophenoxy)-L-proline, monohydrochloride; m.p. 152°–153° (dec.); $[\alpha]_D^{25} = -50°$ (c=0.5, methanol). $R_f$ 0.75 (silica gel, chloroform/methanol/acetic acid, 4:1:1).

Anal. calc'd. for $C_{31}H_{32}FN_3O_6 \cdot HCl \cdot 1.5H_2O$: C, 59.57; H, 5.80; N, 6.72; Cl, 5.67. Found: C, 59.68; H, 5.56; N, 6.67; Cl, 5.99.

EXAMPLE 101

[1(S),4R]-1-[N-[3-(Benzoylamino)-2-oxo-4-phenylbutyl]-L-alanyl]-4-phenyl-L-proline, monohydrochloride (a) (S)-N-[N-(Benzoylamino)-2-oxo-4-phenylbutyl]-N-[(phenylmethoxy)carbonyl]-L-alanine, succinimido ester A mixture of (S)-N-[N-(benzoylamino)-2-oxo-4-phenylbutyl[-N-[(phenylmethoxy)carbonyl]-L-alanine (800 mg., 1.6 mmole), prepared as set forth in Example 100 (c), dicyclohexylcarbodiimide (340 mg., 1.6 mmole), and N-hydroxysuccinimide (190 mg., 1.6 mmole) in tetrahydrofuran (5 ml.) is stirred at 25° for 18 hours. After this time it is filtered and concentrated to give 950 mg. of (S)-N-[N-(benzoylamino)-2-oxo-4-phenylbutyl]-N-[(phenylmethoxy)carbonyl]-L-alanine, succinimido ester.

(b) [1(S),4R]-1-[N-[3-(Benzoylamino)-2-oxo-4-phenylbutyl]-N-[(phenylmethoxy)carbonyl]-L-alanyl]-4-phenyl-L-proline To a solution of (S)-N-[N-(benzoylamino)-2-oxo-4-phenylbutyl]-N-[(phenylmethoxy)carbonyl]-L-alanine, succinimido ester (950 mg., 1.6 mmole) in dimethylformamide (5 ml.) is added (4R)-4-phenyl-L-proline, hydrochloride (375 mg., 1.7 mmole) and triethylamine (40 μl., 3.2 mmole). The resulting mixture is stirred at 25° for 24 hours, after which it is poured into excess 1N hydrochloric acid and extracted with ethyl acetate (3×). The extracts are combined, dried (MgSO4), filtered, and concentrated to give 1.1 g. of [1(S),4R]-1-[N-[3-(benzoylamino)-2-oxo-4-phenylbutyl]-N-8 (phenylmethoxy)carbonyl]-L-alanyl]-4-phenyl-L-proline.

(c) [1(S),4R]-1-[N-[3-(Benzoylamino)-2-oxo-4-phenylbutyl]-L-alanyl]-4-phenyl-L-proline, monohydrochloride The product from part (b) (1.0 g., 1.5 mmole), ethanol (20 ml.), water (5 ml.), 1.0N hydrochloric acid (1.5 ml., 1.5 mmole), and palladium on carbon catalyst (10%, 100 mg.) is hydrogenated at one atmosphere and 25° for 18 hours, after which it is filtered and concentrated. The residue is chromatographed on HP-20 using a linear gradient [0.01N aqueous hydrochloric acid:methanol, 40:60 to 10:90]. Fractions containing the desired product (TLC) are combined and concentrated. The residue is dissolved in a minimum amount of methanol. Ether is added and the resulting white precipitate is collected and dried to give 300 mg. of [1(S),4R]-1-[N-[3-(benzoylamino)-2-oxo-4-phenylbutyl]-L-alanyl]-4-phenyl-L-proline, monohydrochloride; m.p. 160°–162° (dec.); $[\alpha]_D^{25} = -57°$ (c=1.5, methanol). $R_f$ 0.8 (silica gel; chloroform/methanol/acetic acid; 4:1:1).

Anal. calc'd. for C$_{31}$H$_{33}$N$_3$O$_5$.HCl.1.35H$_2$O: C, 53.27; H, 6.29; N, 7.14; Cl, 6.02. Found: C, 63.27; H, 5.17; N, 7.19; Cl, 5.97.

EXAMPLE 102

[1-(S),4S]-1-[N-[3-(Benzoylamino)-2-oxo-4-phenyl-butyl]-L-alanyl]-4-phenyl-L-proline, monohydrochloride Following the procedure of Example 101 but employing (4S)-4-phenyl-L-proline, hydrochloride in part (b), one obtains [1-(S),4S]-1-[N-[3-(benzoylamino)-2-oxo-4-phenylbutyl]-L-alanyl-4-phenyl-L-proline, nonohydrochloride; m.p. 138°–143°; [α]$_D$ = −61° (c = 0.3% in methanol). R$_f$0.84 (silica gel, chloroform/methanol/acetic acid, 4:1:1).

Anal. calc'd. for C$_{31}$H$_{33}$N$_3$O$_5$.HCl.2.13H$_2$O: C, 51.80; H, 6.35; N, 6.98; Cl, 5.88. Found: C, 61.80; H, 5.06; N, 7.05; Cl, 5.65.

EXAMPLE 103

[1(S),4R]-1-[N-[3-(Benzoylamino)-2-oxo-4-phenyl-butyl]-L-alanyl]-4-cyclohexyl-L-proline, monohydrochloride Following the procedure of Example 101 but employing (4R)-4-cyclohexyl-L-proline, hydrochloride in part (b), one obtains [1(S),4R]-1-[N-[3-(benzoylamino)-2-oxo-4-phenylbutyl]-L-alanyl]-4-cyclohexyl-L-proline, monohydrochloride; m.p. 140°–154° (dec.); [α]$_D$ = −83° (c = 0.36% in methanol). R$_f$0.84 (silica gel; chloroform/methanol/acetic acid; 4:1:1).

Anal. calc'd. for C$_{31}$H$_{39}$N$_3$O$_5$.HCl.0.79H$_2$O: C, 63.71; H, 7.17; N, 7.19; Cl, 6.06. Found: C, 63.71; H, 7.21; N, 7.05; Cl, 5.82.

EXAMPLE 104

[1(S),4S]-1-[N-[3-(Benzoylamino)-2-oxo-4-phenyl-butyl]-L-alanyl]-4-cyclohexyl-L-proline, monohydrochloride Following the procedure of Example 101 but employing (4S)-4-cyclohexyl-L-proline, hydrochloride in part (b), one obtains [1(S),4S]-1-[N-[3-(benzoylamino)-2-oxo-4-phenylbutyl]-L-alanyl]-4-cyclohexyl-L-proline, monohydrochloride; m.p. 139°–141° (dec.); [α]$_D$ = −80° (c = 0.2% in methanol). R$_f$0.83 (silica gel; chloroform/methanol/acetic acid; 4:1:1).

Anal. calc'd. for C$_{31}$H$_{39}$N$_3$O$_5$.HCl.1.54H$_2$O: C, 52.28; H, 7.26; N, 7.03; Cl, 5.93 Found: C, 62.28; H, 7.01; N, 7.02; Cl, 6.16.

EXAMPLE 105

(S)-7-[(S)-2-[[3-(Benzoylamino)-2-oxo-4-phenylbutyl]amino]-1-oxopropyl]-1,4-dithia-7-azaspiro[4.4]nonane-8-carboxylic acid, monohydrochloride Following the procedure of Example 101 but employing (S)-1,4-dithia-7-azaspiro[4.4]nonane-8-carboxylic acid, hydrochloride in part (b) for the L-proline reactant, one obtains (S)-7-[(S)-2-[[3-(benzoylamino)-2-oxo-4-phenylbutyl]amino]-1-oxopropyl]-1,4-dithia-7-azaspiro[4.4]nonane-8-carboxylic acid, monohydrochloride; m.p. 170°–172°; [α]$_D^{25}$ = −26° (c = 1.4% in methanol). R$_f$0.78 (silica gel; chloroform/methanol/acetic acid; 6:1:1).

Anal. calc'd. for C$_{27}$H$_{31}$N$_3$O$_5$S$_2$.HCl.0.77H$_2$O: C, 54.77; H, 5.71; N, 7.10; S, 10.83; Cl, 5.99. Found: C, 54.77; H, 5.70; N, 6.94; S, 10.82; Cl, 6.07.

EXAMPLE 106

[1(S),5S]-1-[N-[3-(Benzoylamino)-2oxo-4-phenylbutyl]-L-alanyl]-4,5-dihydro-3-phenyl-1H-pyrazole-5-carboxylic acid, monohydrochloride Following the procedure of Example 101 but employing (S)-4,5-dihydro-3-phenyl-1H-pyrazole-5-carboxylic acid for the L-proline reactant in part (b), one obtains the above named compound.

EXAMPLE 107

(S)-2-[N-[(S)-3-(Benzoylamino)-2-oxo-4-phenylbutyl]-L-alanyl]-1,2,3,4-tetrahydro-3-isoquinolinecarboxylic acid, monohydrochloride Following the procedure of Example 101 but employing (S)-1,2,3,4-tetrahydro-3-isoquinolinecarboxylic acid, hydrochloride in part (b) in place of the proline reactant, one obtains (S)-2-[N-[(S)-3-(benzoylamino)-2-oxo-4-phenylbutyl]-L-alanyl]-1,2,3,4-tetrahydro-3-isoquinolinecarboxylic acid, monohydrochloride.

EXAMPLE 108

1-[N-[(S)-3-(Benzoylamino)-2-oxo-4-phenylbutyl]-L-alanyl]-2-(2-hydroxyphenyl)-4(R)-thiazolidinecarboxylic acid, monohydrochloride Following the procedure of Example 101 but employing 2-[(2-phenylmethoxy)phenyl]-4(R)-thiazolidinecarboxylic acid, hydrochloride in part (b) in place of the proline reactant, one obtains after removal of the hydroxy protecting group 1-[N-[(S)-3-(benzoylamino)-2-oxo-4-phenylbutyl]-L-alanyl]-2-(2-hydroxyphenyl)-4(R)-thiazolidinecarboxylic acid, monohydrochloride.

In a similar manner, the processes of Examples 96, 97, 99 and 100 to 108 can be employed to prepare the compounds of Examples 1 to 95.

EXAMPLE 109

(±)-1-[N-[3-(Benzoylamino)-2-oxo-4-phenylbutyl]-L-alanyl]-L-proline, methyl ester, monohydrochloride (a) 1-[N-(2-Ethoxy-2-oxoethyl)-N-[(phenylmethoxy)-carbonyl]-L-alanyl]-L-proline, 1,1-dimethylethyl ester L-Alanyl-L-proline, 1,1-dimethylethyl ester (25.44 g., 105 mmole) is taken into tetrahydrofuran (400 ml.) with stirring. To this bromoethyl acetate (11.64 ml., 105 mmole) and diisopropylethylamine (18.3 ml., 105 mmole) are added. After 6 hours the reaction mixture is chilled in an ice bath and benzyl chloroformate (16.5 ml., 115.5 mmole) and diisopropylethylamine (20.1 ml., 115.5 mmole) are added. After one hour the ice-bath is removed and the reaction mixture is kept overnight at room temperature. It is then concentrated to dryness, taken into ethyl acetate, and washed neutral with 10% potassium bisulfate and saturated sodium bicarbonate. The crude product (52.3 g.) is purified on a silica gel column eluting with ethyl acetate:hexane (1:1) to yield 42.4 g. of 1-[N-(2-ethoxy-2-oxoethyl)-N-[(phenylmethoxy)carbonyl]-L-alanyl]-L-proline, 1,1-dimethylethyl ester.

(b) 1-[N-(Carboxymethyl)-N-[(phenylmethoxy)carbonyl]-L-alanyl]-L-proline, 1,1-dimethylethyl ester The ester product from part (a) (21 g., 45.4 mmole) is taken into methanol (150 ml.) and 1N sodium hydroxide (50 ml., 50 mmole) with stirring at room temperature. After 5.5 hours the methanol is removed in vacuo and the aqueous portion is extracted with ethyl acetate. The aqueous portion is acidified with concentrated hydrochloric acid and extracted into ethyl acetate to yield 16.95 g. of 1-[N-(carboxymethyl)-N-[(phenylmethoxy)carbonyl]-L-alanyl]-L-proline, 1,1-dimethylethyl ester.

(c) (±)-1-[N-[N-[3-(Benzoylamino)-2-oxo-4-phenylbutyl]-N-[(phenylmethoxy)carbonyl]-L-alanyl]-L-proline, 1,1-dimethylethyl ester The ester product from part (B) (10.0 g., 23 mmole) is taken into dry tetrahydrofuran (75 ml.) with stirring in an ice-bath. To this, oxalylchloride (2.4 ml., 27.6 mmole) is added dropwise followed by 15 drops of dimethylformamide. After 20 minutes the ice-bath is removed and the reaction mixture is kept at room temperature for one hour. The mixture is then concentrated to dryness in vacuo and taken into tetrahydrofuran (40 ml.) with stirring in an ice-bath. To this, 2-phenyl-4-(phenylmethyl)-5(4H)-oxazolone (6 g., 23.8 mmole) in tetrahydrofuran (35 ml.) is added dropwise followed by triethylamine (3.22 ml., 23 mmole). Additional triethylamine is added to maintain a basic atmosphere. After 20 minutes the ice-bath is removed and the reaction mixture is kept at room temperature overnight. The triethylamine hydrochloride is filtered off and the filtrate is concentrated to dryness in vacuo. The residue is taken into pyridine (25 ml.) and 4-dimethylamino pyridine (75 mg.) is added and the solution is stirred for 3 hours under an argon atmosphere. Acetic acid (25 ml.) is added and the reaction mixture is stirred for 45 minutes at 100° under a positive flow of argon. The reaction mixture is concentrated to dryness, taken into ethyl acetate, and washed neutral with saturated sodium bicarbonate and dilute hydrochloric acid. The crude product (12.8 g.) is chromatographed on silica gel eluting with ethyl acetate:hexane (1:1) to give 9.05 g. of (±)-1-[N-[3-(benzoylamino)-2-oxo-4-phenylbutyl]-N-[(phenylmethoxy)carbonyl]-L-alanyl]-L-proline, 1,1-dimethylethyl ester.

(d) (±)-1-[N-[3-(Benzoylamino)-2-oxo-4-phenylbutyl]-N-[(phenylmethoxy)carbonyl]-L-alanyl]-L-proline The ester product from part (c) (11.4 g., 17.7 mmole) is taken into trifluoroacetic acid (50 ml.) and kept at room temperature for 45 minutes. It is then concentrated to dryness and triturated with ether:hexane to yield 10.3 g. of crude product. This material is purified on a silica gel column in benzene/acetic acid (8:2) to give 9.7 g. of (±)-1-[N-[3-(benzoylamino)-2-oxo-4-phenylbutyl]-N-[(phenylmethoxy)carbonyl]-L-alanyl]-L-proline; m.p. 70°-91°; $[\alpha]_D^{23} = -53.0$ (c=1.22, methanol). $R_f$ 0.41 (silica gel, benzene/acetic acid; 8:2).

Anal. calc'd. for $C_{33}H_{35}N_3O_7$ C, 67.68; H, 6.02; N, 7.17. Found: C, 67.95; H, 6.02; N, 6.82.

(e) (±)-1-[N-[3-(Benzoylamino)-2-oxo-4-phenylbutyl]-N-[(phenylmethoxy)carbonyl]-L-alanyl]-L-proline, methyl ester The acid product from part (d) (3.5 g., 6 mmole) is taken into dimethylformamide (12 ml.) with stirring at room temperature. To this sodium bicarbonate (630 mg., 7.5 mmole) and methyl iodide (0.47 ml., 7.5 mmole) are added. After 18 hours, additional methyl iodide (7.4 mmole) and sodium bicarbonate (7.4 mmole) are added. After stirring for an additional 4 hours, the reaction mixture is concentrated to dryness in vacuo, taken into ethyl acetate and washed with saturated sodium bicarbonate. The crude product (3.7 g.) is purified on a silica gel column in ethyl acetate:hexane (2:1) to give 3.5 g. of (±)-1-[N-[3-(benzoylamino)-2-oxo-4-phenylbutyl]-N-[(phenylmethoxy)carbonyl]-L-alanyl]-L-proline, methyl ester.

(f) (±)-1-[N-[3-(benzoylamino)-2-oxo-4-phenylbutyl]-L-alanyl]-L-proline, methyl ester, monohydrochloride The ester product from (e) (900 mg., 1.5 mmole) is taken into ethanol (95%, 100 ml.) and 1N hydrochloric acid (1.8 ml.). Palladium on carbon catalyst (10%, 180 mg.) is added and the reaction mixture is stirred under hydrogen overnight. The reaction mixture is filtered to remove the catalyst, concentrated to dryness and lyophilized twice from water to give 700 mg. of (±)-1-[N-[3-(benzoylamino)-2-oxo-4-phenylbutyl]-L-alanyl]-L-proline, methyl ester, monohydrochloride; m.p. 110°-128° (90°); $[\alpha]_D^{23} = -69.9°$ (c=1.18, methanol). $R_f$ 0.63 (silica gel, chloroform/methanol/acetic acid; 9:1:1).

Anal. calc'd. for $C_{26}H_{31}N_3O_5 \cdot HCl \cdot 0.92H_2O$: C, 60.22; H, 6.58; N, 8.11; Cl, 6.84. Found: C, 60.22; H, 6.28; N, 8.10; Cl, 7.06.

EXAMPLE 110

(±)-1-[N-[3-(Benzoylamino)-2-oxo-4-phenylbutyl]-L-alanyl]-L-proline, methyl ester, monomethanesulfonate (±)-1-[N-[3-(Benzoylamino)-2-oxo-4-phenylbutyl]-N-[(phenylmethoxy)carbonyl]-L-alanyl]-L-proline, methyl ester (600 mg., 1 mmole), prepared as set forth in Example 109 (e), is taken into methanol (60 ml.) and methanesulfonic acid (0.066 ml., 1 mmole). Palladium on carbon catalyst (10%, 120 mg.) is added and the reaction mixture is stirred under hydrogen for 2.5 hours. The reaction mixture is filtered to remove the catalyst and then concentrated in vacuo. The crude product is triturated with ether and filtered. The precipitate is taken into water and lyophilized to yield 470 mg. of (±)-1-[N-[3-(benzoylamino)-2-oxo-4-phenylbutyl]-L-alanyl]-L-proline, methyl ester, monomethanesulfonate; m.p. 80°-140°; $[\alpha]_D^{23} = -61.4°$ (c=1.10, methanol). $R_f$ 0.63 (silica gel, chloroform/methanol/acetic acid; 9:1:1).

Anal. calc'd. for $C_{26}H_{31}N_3O_5 \cdot CH_4O_3S$ C, 56.98; H, 6.34; N, 7.30; S, 5.63. Found: C, 56.98; H, 6.32; N, 7.47; S, 5.63.

EXAMPLE 11

(±)-1-[N-[3-(Benzoylamino)-2-oxo-4-phenylbutyl]-L-alanyl]-L-proline, methyl ester, hemisulfate (±)-1-[N-[3-(Benzoylamino)-2-oxo-4-phenylbutyl]-N-[(phenylmethoxy)carbonyl]-L-alanyl]-L-proline, methyl ester (600 mg., 1 mmole), prepared as set forth in Example 109 (e), is taken into methanol (40 ml.) along with 1N sulfuric acid (0.9 ml.). Palladium on carbon catalyst (10%, 120 mg.) is added and the reaction mixture is stirred under hydrogen for 2 hours. The reaction mixture is filtered to remove the catalyst, concentrated to dryness, triturated with ether and filtered. The crude product (446 mg.) is taken into water, millipore filtered, and lyophilized to yield 405 mg. of (±)-1-[N-[3-(benzoylamino)-2-oxo-4-phenylbutyl]-L-alanyl]-L-proline, methyl ester, hemisulfate; m.p. 98°-112° (85°); $[\alpha]_D^{23} = -60.3°$ (c=1.16, methanol). $R_f$ 0.63 (trailing) (silica gel, chloroform/methanol/acetic acid; 9:1:1).

Anal. calc'd. for $C_{26}H_{31}N_3O_5 \cdot 0.5H_2SO_4 \cdot 0.91H_2O$: C, 58.81; H, 6.42; N, 7.92; S, 3.01. Found: C, 58.81; H, 6.11; N, 7.91; S, 3.09.

EXAMPLE 112

(±)-1-[N-[3-(Benzoylamino)-2-oxo-4-phenylbutyl]-L-alanyl]-L-proline, propyl ester, monomethanesulfonate (a) (±)-1-[N-[3-(Benzoylamino)-2-oxo-4-phenylbutyl]-N-[(phenylmethoxy)carbonyl]-L-alanyl]-L-proline, propyl ester (±)-1-[N-[3-(Benzoylamino)-2-oxo-4-phenylbutyl]-N-[(phenylmethoxy)carbonyl]-L-alanyl]-L-proline (1.17 g., 2 mmole), prepared as set forth in Example 109(d), is taken into tetrahydrofuran (2 ml.) with stirring in an ice-bath. To this is added n-propanol (3.0 ml., 40 mmole) followed by 4-dimethylamino pyridine (122 mg., 1 mmole) and dicyclohexylcarbodiimide (412 mg., 2 mmole). The reaction is allowed to warm to room temperature and to run overnight. The dicyclohexylurea is filtered off and the filtrate is concentrated to dryness in vacuo. The crude product (1.2 g.) is chromatographed on a silica gel column in benzene:acetic acid (9:1) to yield 1.0 g. of (±)-1-[N-[3-(benzoylamino)-2-oxo-4-phenylbutyl]-N-[(phenylmethoxy)carbonyl]-L-alanyl]-L-proline, propyl ester.

(b) (±)-1-[N-[3-(Benzoylamino)-2-oxo-4-phenylbutyl]-L-alanyl]-L-proline, propyl ester, monomethanesulfonate The ester product from part (a) (500 mg., 0.8 mmole) is taken into methanol (50 ml.). Methanesulfonic acid (0.72 ml. of 1N solution in methanol) and palladium on carbon catalyst (10%, 100 mg.) are added and the reaction mixture is stirred under hydrogen overnight. The reaction mixture is filtered to remove the catalyst, concentrated to dryness, triturated with ether and filtered to yield 406 mg. of crude product. This is taken into water, millipore filtered, and lyophilized to yield 390 mg. of (±)-1-[N-[3-(benzoylamino)-2-oxo-4-phenylbutyl]L-alanyl]-L-proline, propyl ester, monomethanesulfonate; m.p. 82°-94° (69°); $[\alpha]_D^{23} = -60.5°$ (c=0.95, methanol). $R_f$ 0.46 (silica gel, chloroform/methanol/acetic acid; 90:5:5).

Anal. calc'd. for $C_{28}H_{35}N_3O_5.CH_4O_3S.0.5H_2O$: C, 58.15; H, 6.73; N, 7.01; S, 5.34. Found: C, 58.15; H, 6.63; N, 7.05; S, 5.34.

EXAMPLE 113

(±)-1-[N-[3-(Benzoylamino)-2-oxo-4-phenylbutyl]-L-alanyl]-L-proline, ethyl ester, monomethanesulfate (a) (±)-1-[N-[3-(Benzoylamino)-2-oxo-4-phenylbutyl]-N-[(phenylmethoxy)carbonyl]-L-alanyl]-L-proline, ethyl ester (±)-1-[N-[3-(Benzoylamino)-2-oxo-4-phenylbutyl]-N-[(phenylmethoxy)carbonyl]-L-alanyl]-L-proline (1.17 g., 2 mmole), prepared as set forth in Example 109 (d), is taken into tetrahydrofuran (2 ml.) with stirring in an ice-bath. To this is added absolute ethanol (2.3 ml., 40 mmole) followed by 4-dimethylamino pyridine (122 mg., 1 mmole) and dicyclohexylcarbodiimide (412 mg., 2 mmole). The reaction is allowed to run overnight at room temperature. The dicyclohexylurea is filtered off, the filtrate is concentrated to dryness, the residue is taken into ethyl acetate and washed neutral with 10% potassium bisulfate and saturated sodium carbonate. The crude product (1.2 g.) is purified on silica gel column in benzene:acetic acid (8:2) to yield 1.0 g. of (±)-1-[N-[3-(benzoylamino)-2-oxo-4-phenylbutyl]-N-[(phenylmethoxy)carbonyl]-L-alanyl]-L-proline, ethyl ester.

(b) (±)-1-[N-[3-(Benzoylamino)-2-oxo-4-phenylbutyl]-L-alanyl]-L-proline, ethyl ester, monomethanesulfate The ester product form part (a) (500 mg., 0.8147 mmole) is taken into 50 ml. of methanol-methanolic methanesulfonic acid (1N, 0.733 ml.). Palladium on carbon catalyst (10%, 100 mg.) is added and the reaction mixture is stirred under positive hydrogen pressure for 3 hours. The reaction mixture is filtered to remove the catalyst, concentrated to dryness, triturated with ether and filtered. The precipitate (428 mg.) is taken into water, millipore filtered, and lyophilized to yield 360 mg. of (±)-1-[N-[3-(benzoylamino)-2-oxo-4-phenylbutyl]-L-alanyl]-L-proline, ethyl ester, monomethanesulfonate; m.p. 91°-96° (72°); $[\alpha]_D^{23} = -57.2°$ (c=1.04, methanol). $R_f$ 0.44 (silica gel, chloroform/methanol/acetic acid; 90:5:5).

Anal. calc'd. for $C_{27}H_{33}N_3O_5.CH_4SO_3.0.6H_2O$: C, 57.33; H, 6.56; N, 7.17; S, 5.47. Found: C, 57.33; H, 6.43; N, 7.12; S, 5.47.

EXAMPLE 114

(±)-1-[N-[3-(Benzoylamino)-2-oxo-4-phenylbutyl]-L-alanyl]-L-proline, 1-methylethyl ester, monomethanesulfonate (a) (±)-1-[N-[3-(Benzoylamino)-2-oxo-4-phenylbutyl]-N-[(phenylmethoxy)carbonyl]-L-alanyl]-L-proline, 1-methylethyl ester (±)-1-[N-[3-(Benzoylamino)-2-oxo-4-phenylbutyl]-N-[(phenylmethoxy)carbonyl]-L-alanyl]-L-proline (1.17 g., 2 mmole), prepared as set forth in Example 109 (d), and isopropanol (3.0 ml., 40 mmole) are taken into tetrahydrofuran (2 ml.) with stirring in an ice-bath. To this dicyclohexylcarbodiimide (412 mg., 2 mmole) is added. The reaction is allowed to run overnight at room temperature. It is then concentrated to dryness, taken into ethyl acetate and the dicyclohexylurea filtered off. The filtrate is washed neutral with 10% potassium bisulfate and saturated sodium bicarbonate. The crude product (1.2 g.) is purified on a silica gel column with benzene:acetic acid (8:2) to yield 1.0 g. of (±)-1-[N-[3-(benzoylamino)-2-oxo-4-phenylbutyl]-N-[(phenylmethoxy)carbonyl]-L-alanyl]-L-proline, 1-methylethyl ester.

(b) (±)-1-[N-[3-(Benzoylamino)-2-oxo-4-phenylbutyl]-L-alanyl]-L-proline, 1-methylethyl ester, monomethanesulfonate The ester product from part (a) (815 mg., 1.3 mmole) is taken into methanol (20 ml.) and methanolic methanesulfonic acid (1N, 1.17 ml.) and stirred under hydrogen in the pressence of palladium on carbon catalyst (10%, 160 mg.) for 3 hours. The reaction mixture is filtered to remove the catalyst and concentrated to dryness in vacuo. The residue is triturated with ether and the precipitate filtered to yield 704 mg. of crude product. This is taken into 35 ml. of water (2% solution), millipore filtered, and lyophilized to give 600 mg. of (±)-1-[N-[3-(benzoylamino)-2-oxo-4-phenylbutyl]-L-alanyl]-L-proline, 1-methylethyl ester, monomethanesulfonate; m.p. 88°-105°; $[\alpha]_D^{23} = -55.2°$ (c=1.05, methanol). $R_f$ 0.33 (silica gel, chloroform/methanol/acetic acid; 9:1:1).

Anal. calc'd. for $C_{28}H_{35}N_3O_5.CH_4O_3S.0.66H_2O$: C, 57.89; H, 6.75; N, 6.99; S, 5.33. Found: C, 57.89; H, 6.62; N, 6.62; S, 5.32.

EXAMPLES 115-123

Following the procedure of Examples 109, 112, 113 and 114, (±)-1-[N-[-3-(benzoylamino)-2-oxo-4-phenylbutyl]-N-[(phenylmethoxy)carbonyl]-L-alanyl]-L-proline is treated with the reagent shown below in Col. I. Removal of the alanyl protecting group yields the ester product shown below in Col. II.

Col. II

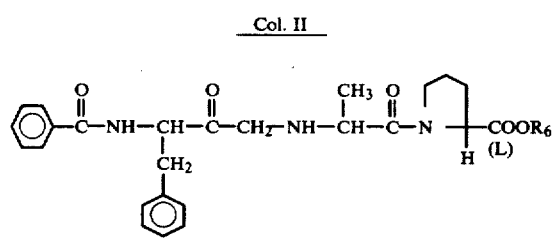

| Example | Col. I | R6 |
|---|---|---|
| 115 | Cl—CH—O—C(=O)—C2H5<br>(cyclohexyl) | —CH—O—C(=O)—C2H5<br>(cyclohexyl) |
| 116 | Cl—CH—O—C(=O)—C2H5<br>\|<br>CH(CH3)2 | —CH—O—C(=O)—C2H5<br>\|<br>CH(CH3)2 |
| 117 | Cl—CH2—O—C(=O)—C(CH3)3 | —CH2—O—C(=O)—C(CH3)3 |
| 118 | Br—CH2—O—C(=O)—CH3 | —CH2—O—C(=O)—CH3 |
| 119 | Cl—CH2—O—C(=O)—phenyl | —CH2—O—C(=O)—phenyl |
| 120 | I—CH2—C(=O)—O—C(CH3)3 | —CH2—C(=O)—O—C(CH3)3 |
| 121 | CH3<br>\|<br>I—C—C(=O)—O—CH3<br>\|<br>CH3 | CH3<br>\|<br>—C—C(=O)—O—CH3<br>\|<br>CH3 |
| 122 | CH—(CH2—O—CH2—phenyl)2<br>\|<br>OH | —CH(CH2—OH)2 |
| 123 | CH2—CH——CH2<br>\|   \|         \|<br>OH  O       O<br>     \|        \|<br>    H2C-phenyl  H2C-phenyl | —CH2—CH—CH2<br>      \|    \|<br>     OH  OH |

EXAMPLE 124

1-[N-[(S)-3-(Benzoylamino)-2-oxo-4-phenylbutyl]-L-alanyl]-L-proline, sodium salt 1-[N-[(S)-3-(Benzoylamino)-2-oxo-4-phenylbutyl]-L-alanyl]-L-proline, hydrochloride (424 mg., 1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm.×60 cm.) of Sephadex chromatography gel G-10 and eluted with water. Fractions containing the desired product are pooled and lyophilized to obtain 1-[N-[(S)-3-(benzoylamino)-2-oxo-4-phenylbutyl]-L-alanyl]-L-proline, sodium salt.

EXAMPLE 125

1000 tablets each containing the following ingredients:

| | |
|---|---|
| 1-[N—[(S)-3-(Benzoyl-amino)-2-oxo-4-phenyl-butyl]-L-alanyl]-L-proline, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. | are prepared from sufficient bulk quantities by mixing the 1-[N-[(S)-3-(benzoylamino)-2-oxo-4-phenylbutyl]-L-alanyl]-L-proline, sodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 123 can be prepared.

A similar procedure can be employed to form tablets containing 50 mg. of active ingredient.

EXAMPLE 126

Two piece #1 gelatin capsules each containing 50 mg. of 1-[N-[(S)-3-(benzoylamino)-2-oxo-4-phenylbutyl]-L-alanyl]-L-proline, sodium salt are filled with a mixture of the following ingredients:

| | |
|---|---|
| 1-[N—[(S)-3-(Benzoylamino)-2-oxo-4-phenylbutyl]-L-alanyl]-L-proline, sodium salt | 50 mg. |
| Magnesium stearate | 7 mg. |
| Lactose | 193 mg. |
| | 250 mg. |

In a similar manner capsules containing 50 mg. of the product of any of Examples 1 to 123 can be prepared.

EXAMPLE 127

An injectable solution is prepared as follows:

| | |
|---|---|
| 1-[N—[(S)-3-(Benzoyl-amino)-2-oxo-4-phenyl-butyl]-L-alanyl]-L-proline, sodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 123.

EXAMPLE 128

1000 tablets each containing the following ingredients:

| | |
|---|---|
| 1-[N—[(S)-3-(Benzoyl-amino)-2-oxo-4-phenyl-butyl]-L-alanyl]-L-proline, sodium salt | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[N-[(S)-3-(benzoylamino)-2-oxo-4-phenylbutyl]-L-alanyl]-L-proline, sodium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 123.

What is claimed is:

1. A compound of the formula

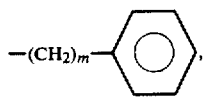

or a pharmaceutically acceptable salt thereof wherein X is

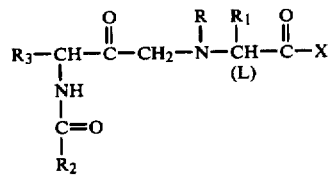

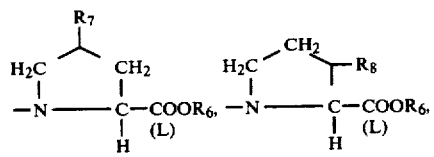

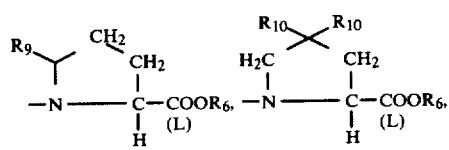

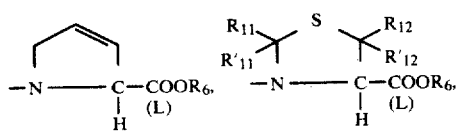

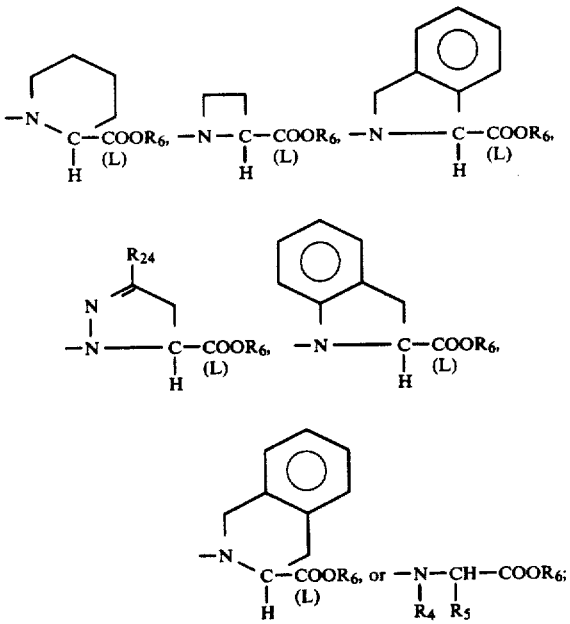

R is hydrogen, lower alkyl, cycloalkyl,

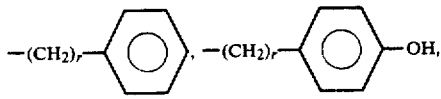

—(CH$_2$)$_2$—NH$_2$, —(CH$_2$)$_3$—NH$_2$, —(CH$_2$)$_4$—NH$_2$, —(CH$_2$)$_2$—OH, —(CH$_2$)$_3$—OH, —(CH$_2$)$_4$—OH, —(CH$_2$)$_2$—SH, —(CH$_2$)$_3$—SH, or —(CH$_2$)$_4$—SH;

R$_1$ is hydrogen, lower alkyl, halo substituted lower alkyl,

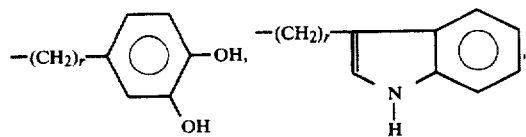

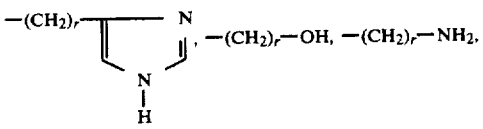

—(CH$_2$)$_r$—SH, —(CH$_2$)$_r$—S—lower alkyl,

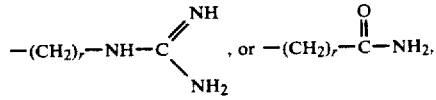

provided that R$_1$ is hydrogen only when R is other than hydrogen;

R$_2$ is

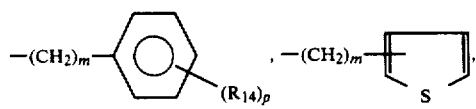
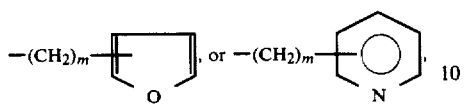
$R_3$ is hydrogen, lower alkyl,
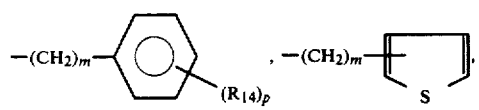
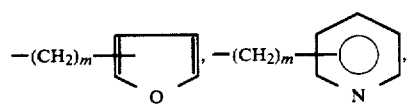
halo substituted lower alkyl, $-(CH_2)_m-$cycloalkyl,
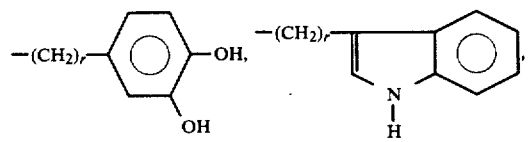
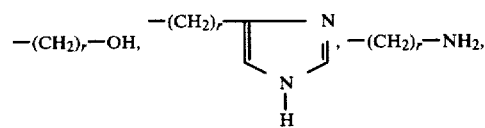
$-(CH_2)_r-SH$, $-(CH_2)_r-S-$lower alkyl,
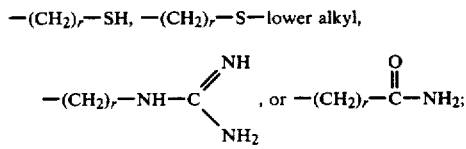
$R_4$ is hydrogen, lower alkyl,
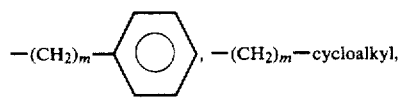
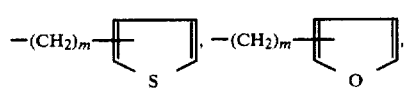
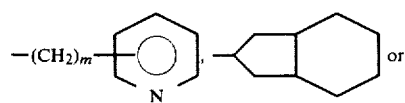
$R_5$ is hydrogen, lower alkyl,
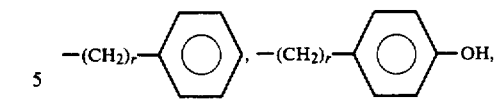
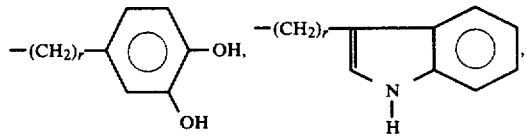
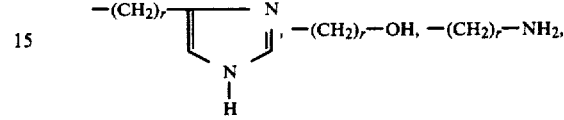
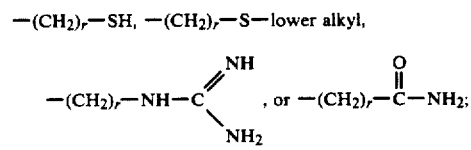
$-(CH_2)_r-SH$, $-(CH_2)_r-S-$lower alkyl,
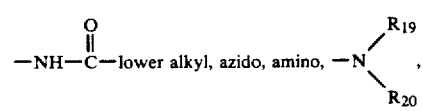
r is an integer from 1 to 4;
$R_7$ is hydrogen, lower alkyl, halogen, keto, hydroxy,
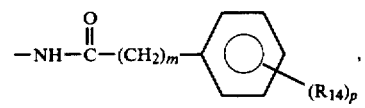
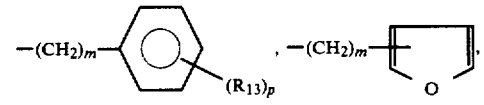
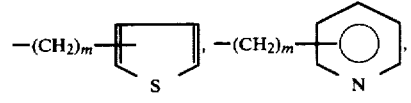
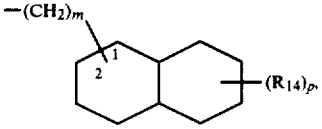
a 1- or 2-naphthyl of the formula
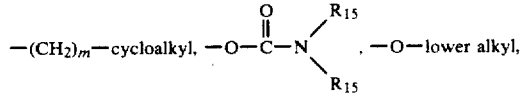
a 1- or 2-naphthyloxy of the formula
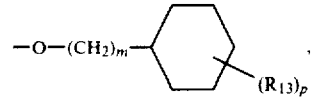

-continued

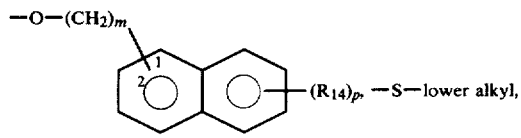

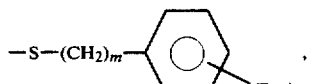

or a 1- or 2-naphthylthio of the formula

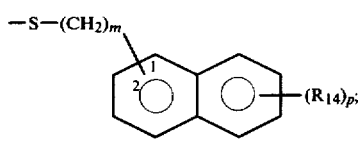

$R_8$ is keto, halogen,

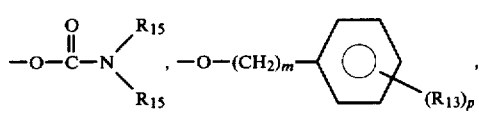

—O—lower alkyl, a 1- or 2-naphthyloxy of the formula

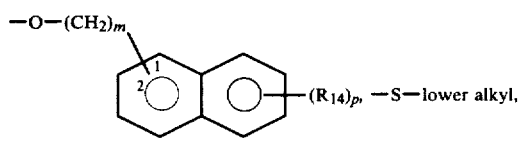

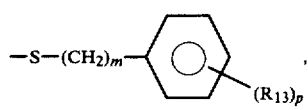

or a 1- or 2-naphthylthio of the formula

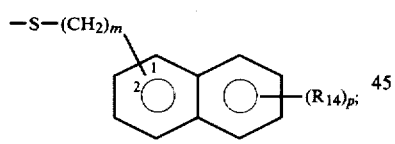

$R_9$ is keto or

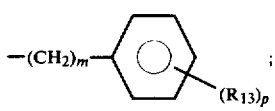

$R_{10}$ is halogen or —Y—$R_{16}$;
$R_{11}$, $R_{11}'$, $R_{12}$ and $R_{12}'$ are independently selected from hydrogen and lower alkyl or $R_{11}'$, $R_{12}$ and $R_{12}'$ are hydrogen and $R_{11}$ is

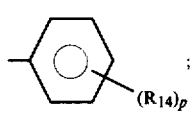

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two, three, or four;

p is one, two or three provided that p is more than one only if $R_{13}$ or $R_{14}$ is hydrogen, methyl, methoxy, chloro, or fluoro;

$R_{15}$ is hydrogen or lower alkyl of 1 to 4 carbons;

Y is oxygen or sulfur;

$R_{16}$ is lower alkyl of 1 to 4 carbons,

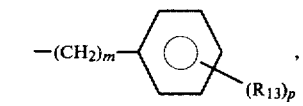

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;

$R_{19}$ is lower alkyl, benzyl, or phenethyl;
$R_{20}$ is hydrogen, lower alkyl, benzyl or phenethyl;
$R_6$ is hydrogen, lower alkyl, benzyl, benzhydryl,

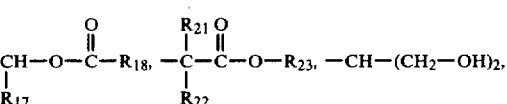

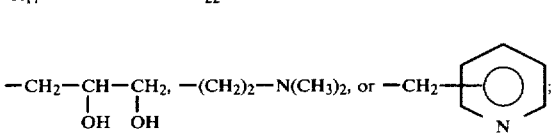

$R_{17}$ is hydrogen, lower alkyl, cycloalkyl or phenyl;
$R_{18}$ is hydrogen, lower alkyl, lower alkoxy, phenyl, or $R_{17}$ and $R_{18}$ taken together are —(CH$_2$)$_2$—, —(CH$_2$)$_3$—, —CH=CH, or

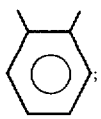

$R_{24}$ is hydrogen, lower alkyl,

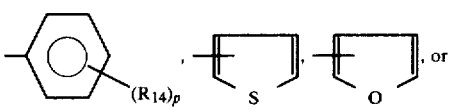

$R_{21}$ and $R_{22}$ are independently selected from the group consisting of hydrogen and lower alkyl; and
$R_{23}$ is lower alkyl.

2. A compound of claim 1 wherein:

R is hydrogen, straight or branched chain lower alkyl of 1 to 4 carbons, or phenyl;

$R_1$ is hydrogen, straight or branched chain lower alkyl of 1 to 4 carbons, $CF_3$, $-(CH_2)_r-NH_2$,

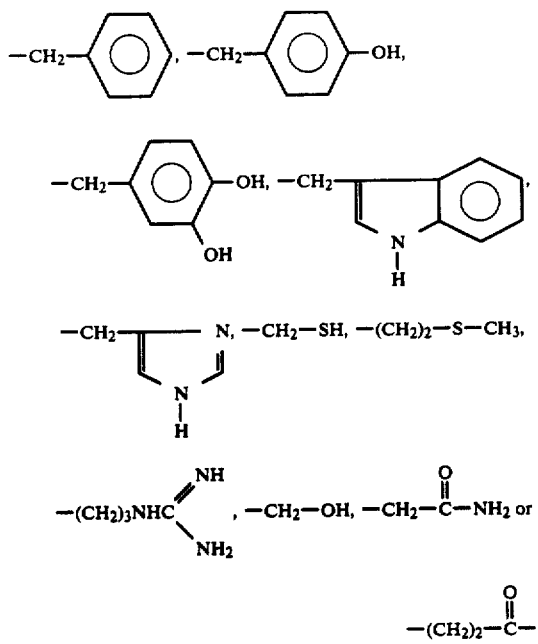

provided that $R_1$ is hydrogen only if R is other than hydrogen;

$R_4$ is hydrogen, cyclohexyl, or phenyl;

$R_5$ is hydrogen, straight or branched chain lower alkyl of 1 to 4 carbons,

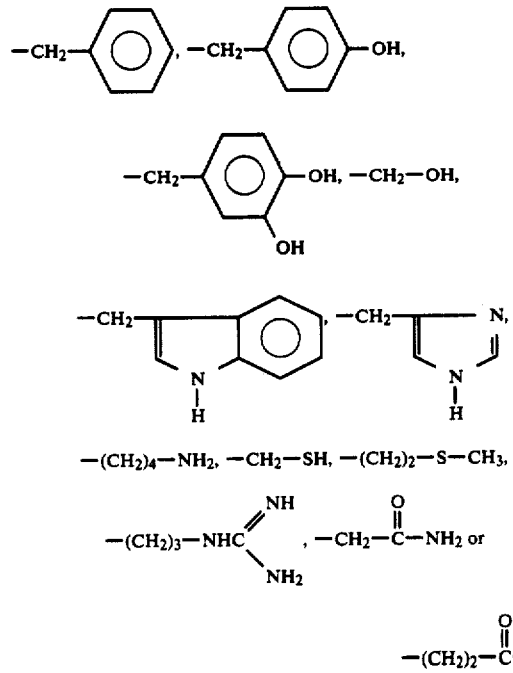

$R_6$ is hydrogen, straight or branched chain lower alkyl of 1 to 4 carbons, an alkali metal salt ion,

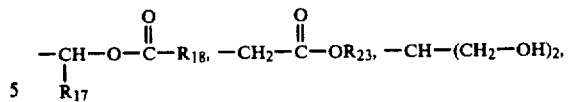

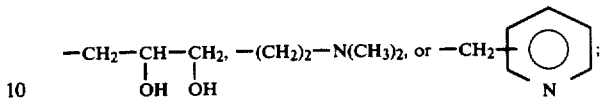

$R_{17}$ is hydrogen, straight or branched chain lower alkyl of 1 to 4 carbons, or cyclohexyl;

$R_{18}$ is straight or branched chain lower alkyl of 1 to 4 carbons or phenyl;

$R_{23}$ is straight or branched chain lower alkyl of 1 to 4 carbons;

$R_2$ is

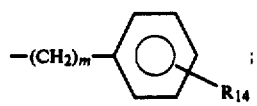

$R_3$ is straight or branched chain lower alkyl of 1 to 4 carbons, $-(CH_2)_r-NH_2$,

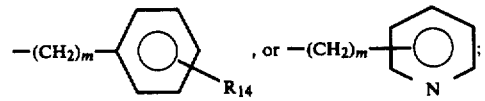

$R_7$ is hydrogen, hydroxy, straight or branched chain lower alkyl of 1 to 4 carbons, cyclohexyl, amino, —O—lower alkyl wherein lower alkyl is straight or branched chain of 1 to 4 carbons,

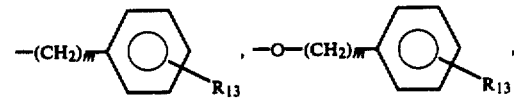

1-naphthyloxy, 2-naphthyloxy, —S—lower alkyl wherein lower alkyl is straight or branched chain of 1 to 4 carbons,

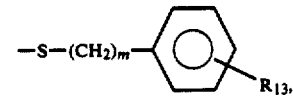

1naphthylthio, or 2-naphthylthio;

$R_8$ is —O—lower alkyl, —S—lower alkyl,

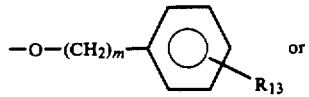

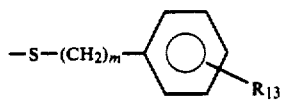

wherein lower alkyl is straight or branched chain of 1 to 4 carbons,

R9 is phenyl, 2-hydroxyphenyl or 4-hydroxyphenyl;
R10 are both fluoro, both chloro, or both —Y—R16;
Y is O or S;
R16 is straight or branched chain lower alkyl of 1 to 4 carbons or the R16 groups join to complete an unsubstituted 5- or 6-membered ring or said ring in which one or more of the available carbons has a methyl or dimethyl substituent;
R11, R11', R12 and R12' are all hydrogen or R11 is phenyl, 2-hydroxyphenyl, or 4-hydroxyphenyl and R11', R12 and R12' are all hydrogen;
r is an integer from 1 to 4;
m is zero, one, or two;
R13 is hydrogen, methyl, methoxy, methylthio, chloro, bromo, fluoro, or hydroxy;
R14 is hydrogen, methyl, methoxy, methylthio, chloro, bromo, fluoro, or hydroxy; and
R24 is phenyl.

3. A compound of claim 2 wherein:
X is

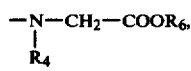

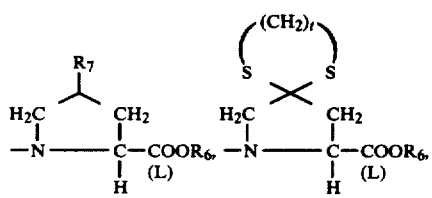

or

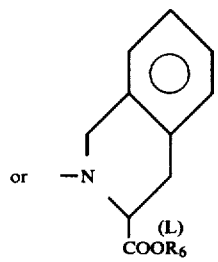

R is hydrogen or methyl;
R1 is hydrogen, methyl, or —(CH2)4—NH2 provided that R1 is hydrogen only if R is other than hydrogen;
R4 is cyclohexyl or phenyl;
R6 is hydrogen, straight or branched chain lower alkyl or 1 to 4 carbons, or an alkali metal salt ion;
R7 is hydrogen, cyclohexyl, lower alkoxy of 1 to 4 carbons,

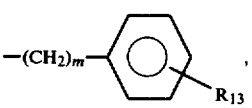

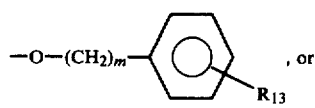, or

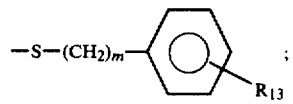

m is zero, one or two;
R13 is hydrogen, methyl, methoxy, methylthio, chloro, bromo, fluoro, or hydroxy; and
t is 2 or 3.

4. A compound of claim 3 wherein X is

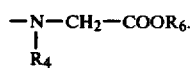

5. A compound of claim 4 wherein
R2 is phenyl; and
R3 is benzyl.

6. The compound of claim 5 wherein
R is hydrogen;
R1 is methyl;
R4 is cyclohexyl; and
R6 is hydrogen.

7. The compound of claim 5 wherein
R is hydrogen;
R1 is methyl;
R4 is phenyl; and
R6 is hydrogen.

8. The compound of claim 5 wherein
R is methyl;
R1 is hydrogen;
R4 is cyclohexyl; and
R6 is hydrogen.

9. A compound of claim 3 wherein:
X is

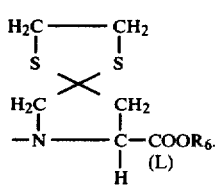

10. A compound of claim 9 wherein:
R2 is phenyl; and
R3 is benzyl.

11. The compound of claim 10 wherein:
R is methyl;
R1 is hydrogen; and
R6 is hydrogen.

12. The compound of claim 10 wherein:
R is methyl;
R1 is hydrogen; and
R6 is methyl.

13. The compound of claim 10 wherein:
R is hydrogen;
R1 is methyl; and
R6 is hydrogen.

14. A compound of claim 3 wherein
X is

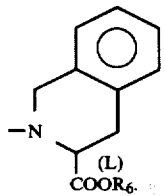

15. The compound of claim 14 wherein:
R₂ is phenyl; and
R₃ is benzyl.
16. The compound of claim 15 wherein:
R is methyl;
R₁ is hydrogen; and
R₆ is hydrogen.
17. The compound of claim 15 wherein
R is hydrogen;
R₁ is methyl; and
R₆ is hydrogen.
18. A compound of claim 3 wherein:
X is

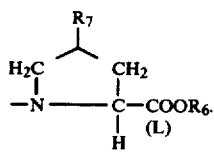

19. A compound of claim 18 wherein:
R₇ is hydrogen.
20. The compound of claim 19 wherein:
R₂ is phenyl;
R₃ is —(CH₂)₄—NH₂;
R is hydrogen;
R₁ is methyl; and
R₆ is hydrogen.
21. The compound of claim 19 wherein:
R₂ is phenyl;
R₃ is —(CH₂)₃—CH₃;
R is hydrogen;
R₁ is methyl; and
R₆ is hydrogen.
22. The compound of claim 19 wherein:
R₂ is phenyl;
R₃ is

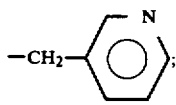

R is hydrogen;
R₁ is methyl; and
R₆ is hydrogen.
23. The compound of claim 19 wherein:
R₂ is phenyl;
R₃ is

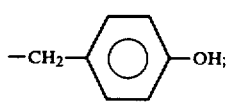

R is hydrogen;
R₁ is methyl; and
R₆ is hydrogen.
24. A compound of claim 19 wherein:
R₂ is phenyl; and
R₃ is benzyl.
25. The compound of claim 24 wherein:
R is hydrogen;
R₁ is methyl; and
R₆ is hydrogen.
26. The compound of claim 25, 1-[N-[(S)-3-(benzoylamino)-2-oxo-4-phenylbutyl]-L-alanyl]-L-proline, monohydrochloride.
27. The compound of claim 24 wherein:
R is hydrogen;
R₁ is methyl; and
R₆ is methyl.
28. The compound of claim 24 wherein:
R is hydrogen;
R₁ is methyl; and
R₆ is ethyl.
29. The compound of claim 24 wherein:
R is hydrogen;
R₁ is methyl; and
R₆ is n-propyl.
30. The compound of claim 24 wherein:
R is hydrogen;
R₁ is methyl; and
R₆ is isopropyl.
31. The compound of claim 24 wherein
R is methyl;
R₁ is hydrogen; and
R₆ is hydrogen.
32. The compound of claim 24 wherein:
R is hydrogen;
R₁ is —(CH₂)₄—NH₂; and
R₆ is hydrogen.
33. A compound of claim 18 wherein R₇ is

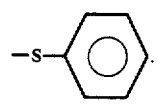

34. A compound of claim 33 wherein:
R₂ is phenyl; and
R₃ is benzyl.
35. The compound of claim 34 wherein:
R is methyl;
R₁ is hydrogen; and
R₆ is hydrogen.
36. A compound of claim 18 wherein R₇ is

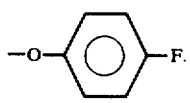

37. A compound of claim 36 wherein:
R₂ is phenyl; and
R₃ is benzyl.
38. The compound of claim 37 wherein:
R is methyl;
R₁ is hydrogen; and
R₆ is hydrogen.
39. The compound of claim 37 wherein:
R is methyl;

R₁ is hydrogen; and
R₆ is methyl.
40. The compound of claim 37 wherein:
R is hydrogen;
R₁ is methyl; and
R₆ is hydrogen.
41. A compound of claim 18 wherein R₇ is phenyl.
42. A compound of claim 41 wherein:
R₂ is phenyl; and
R₃ is benzyl.
43. The compound of claim 42 wherein:
R is hydrogen;
R₁ is methyl; and
R₆ is hydrogen.
44. A compound of claim 18 wherein R₇ is cyclohexyl.
45. A compound of claim 44 wherein:
R₂ is phenyl; and
R₃ is benzyl.
46. The compound of claim 45 wherein:
R is hydrogen;
R₁ is methyl; and
R₆ is hydrogen.
47. A compound of claim 1 wherein:
R is lower alkyl, cycloalkyl,

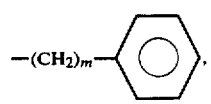

—(CH₂)₂—NH₂, —(CH₂)₃—NH₂, —(CH₂)₄—NH₂, —(CH₂)₂—OH, —(CH₂)₃—OH, —(CH₂)₄—OH, —(CH₂)₂—SH, —(CH₂)₃—SH, or —(CH₂)₄—SH; and
m is zero, one, two, three or four.
48. The compound of claim 47 wherein R is methyl.
49. A compound of the formula

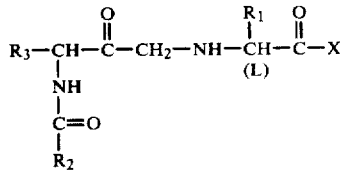

or a pharmaceutically acceptable salt thereof wherein
X is

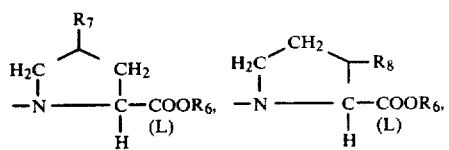

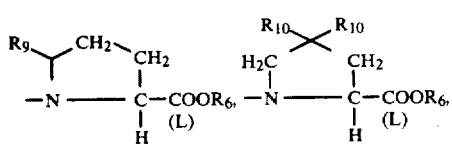

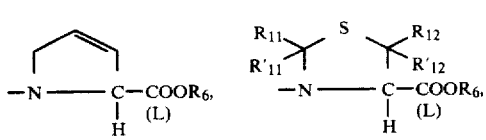

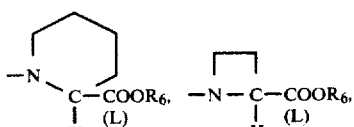

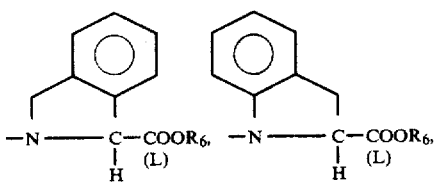

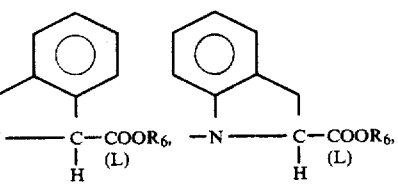

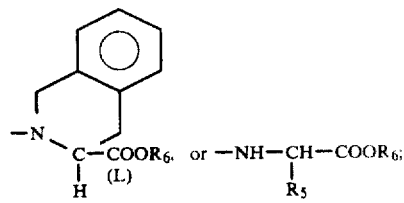

R₁ is lower alkyl, halo substituted lower alkyl,

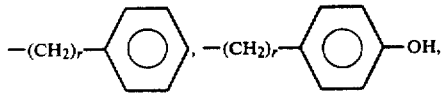

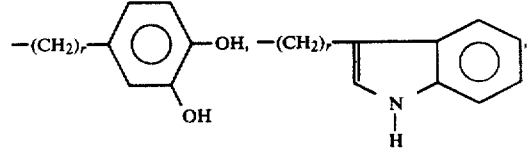

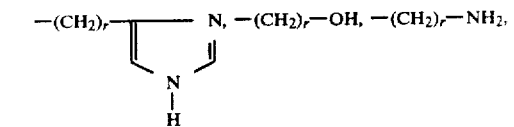

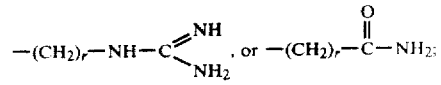

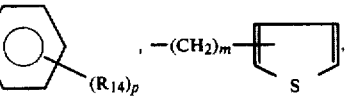

R₂ is

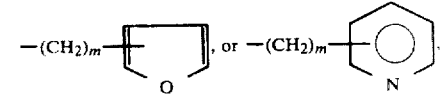

R₃ is hydrogen, lower alkyl,

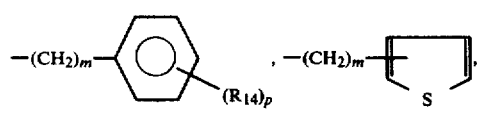

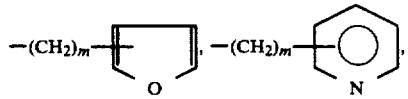

halo substituted lower alkyl, —(CH$_2$)$_m$—cycloalkyl,

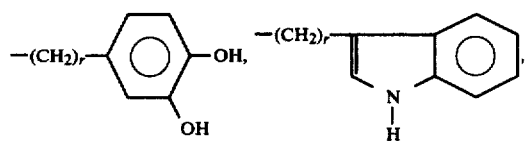

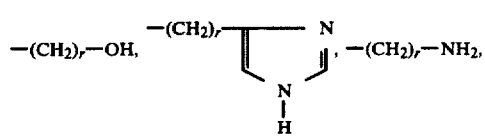

—(CH$_2$)$_r$—SH, —(CH$_2$)$_r$—S—lower alkyl,

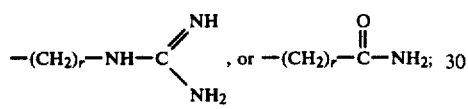

R$_5$ is hydrogen, lower alkyl,

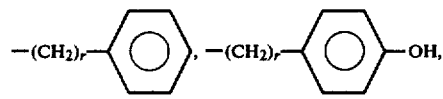

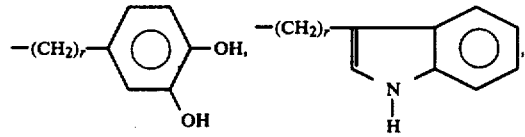

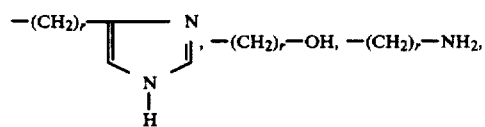

—(CH$_2$)$_r$—SH, —(CH$_2$)$_r$—S—lower alkyl,

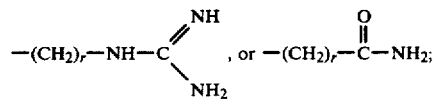

r is an integer from 1 to 4;
R$_7$ is hydrogen, lower alkyl, halogen, keto, hydroxy,

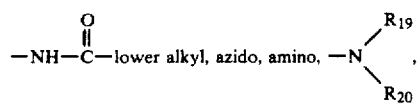

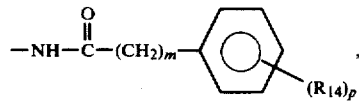

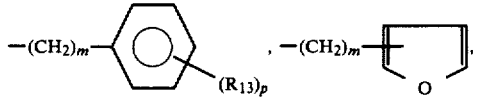

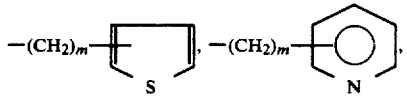

a 1- or 2-naphthyl of the formula

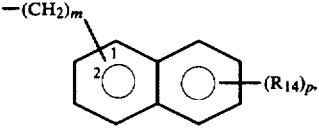

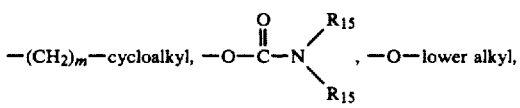

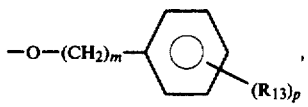

a 1- or 2-naphthyloxy of the formula

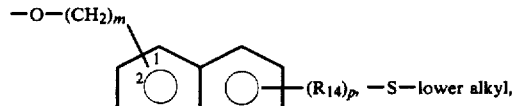

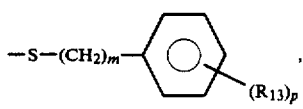

or a 1- or 2-naphthylthio of the formula

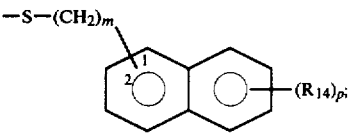

R$_8$ is keto, halogen,

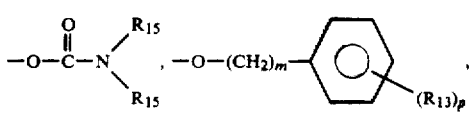

—O—lower alkyl, a 1- or 2-naphthyloxy of the formula

-continued

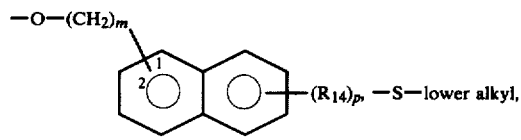

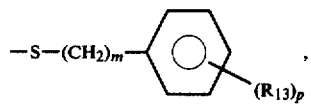

or a 1- or 2-naphthylthio of the formula

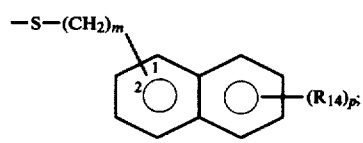

$R_9$ is keto or

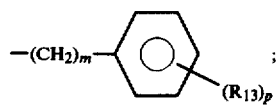

$R_{10}$ is halogen or $-Y-R_{16}$;
$R_{11}$, $R_{11}'$, $R_{12}$ and $R_{12}'$ are independently selected from hydrogen and lower alkyl or $R_{11}'$, $R_{12}$ and $R_{12}'$ are hydrogen and $R_{11}$ is

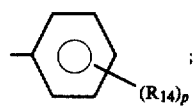

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;
m is zero, one, two, three, or four;
p is one, two or three provided that p is more than one only if $R_{13}$ or $R_{14}$ is hydrogen, methyl, methoxy, chloro, or fluoro;
$R_{15}$ is hydrogen or lower alkyl of 1 to 4 carbons;
Y is oxygen or sulfur;
$R_{16}$ is lower alkyl of 1 to 4 carbons,

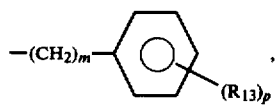

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.
$R_{19}$ is lower alkyl, benzyl, or phenethyl;
$R_{20}$ is hydrogen, lower alkyl, benzyl or phenethyl; and
$R_6$ is hydrogen, lower alkyl, benzyl, benzhydryl, or

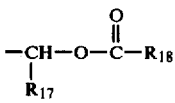

wherein $R_{17}$ is hydrogen, lower alkyl, cycloalkyl or phenyl, and $R_{18}$ is hydrogen, lower alkyl, lower alkoxy, phenyl, or $R_{17}$ and $R_{18}$ taken together are $-(CH_2)_2-$, $-(CH_2)_3-$, $-CH=CH$, or

50. A pharmaceutical composition useful for treating hypertension comprising a pharmaceutically acceptable carrier and a hypotensive compound of the formula

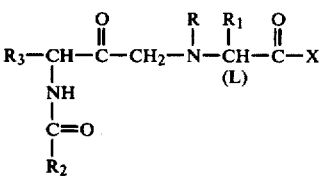

wherein R, $R_1$, $R_2$, $R_3$ and X are as defined in claim 1.
51. The method of treating hypertension in a mammalian host which comprises administering an effective amount of the composition of claim 50.
52. A pharmaceutical composition useful as an analgesic comprising a pharmaceutically acceptable carrier and an enkepalinase inhibiting compound of the formula

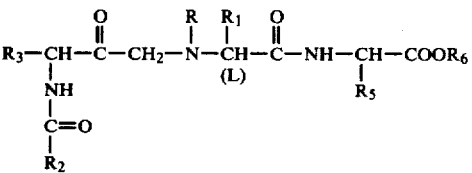

wherein R, $R_1$, $R_2$, $R_3$, $R_5$ and $R_6$ are as defined in claim 1.
53. The method of relieving pain in a mammalian host which comprises administering an effective amount of the composition of claim 52.

* * * * *